United States Patent
Beck et al.

(10) Patent No.: US 8,772,282 B2
(45) Date of Patent: Jul. 8, 2014

(54) TETRAHYDROPYRROLOTHIAZINE COMPOUNDS

(71) Applicant: Eli Lilly and Company, Indianapolis, IN (US)

(72) Inventors: James Peter Beck, Zionsville, IN (US); Steven James Green, Indianapolis, IN (US); Jose Eduardo Lopez, Fishers, IN (US); Brian Michael Mathes, Indianapolis, IN (US); Dustin James Mergott, Zionsville, IN (US); Warren Jaye Porter, Indianapolis, IN (US); Zoran Rankovic, Carmel, IN (US); Yuan Shi, Carmel, IN (US); Brian Morgan Watson, Carmel, IN (US); Leonard Larry Winneroski, Jr., Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/096,443

(22) Filed: Dec. 4, 2013

(65) Prior Publication Data
US 2014/0094454 A1 Apr. 3, 2014

Related U.S. Application Data

(63) Continuation of application No. 13/851,116, filed on Mar. 27, 2013, now Pat. No. 8,629,270.

(60) Provisional application No. 61/758,798, filed on Jan. 31, 2013, provisional application No. 61/700,960, filed on Sep. 14, 2012, provisional application No. 61/619,460, filed on Apr. 3, 2012.

(51) Int. Cl.
*A61K 31/542* (2006.01)

(52) U.S. Cl.
USPC .......................... 514/224.2; 544/48

(58) Field of Classification Search
USPC ....................................... 514/224.2
See application file for complete search history.

(56) References Cited

U.S. PATENT DOCUMENTS

| | | | |
|---|---|---|---|
| 7,868,000 B2 | 1/2011 | Zhu et al. | |
| 8,278,441 B2 | 10/2012 | Mergott et al. | |
| 2009/0209755 A1 | 8/2009 | Suzuki et al. | |
| 2010/0093999 A1 | 4/2010 | Motoki et al. | |
| 2010/0317850 A1 | 12/2010 | Suzuki et al. | |
| 2012/0245155 A1 | 9/2012 | Yoshida et al. | |
| 2013/0053373 A1 | 2/2013 | Brodney et al. | |

FOREIGN PATENT DOCUMENTS

| | | |
|---|---|---|
| EP | 2151435 A1 | 10/2010 |
| WO | 2009131974 A1 | 10/2009 |
| WO | 2009131975 A1 | 10/2009 |
| WO | 2012162334 A1 | 11/2012 |

OTHER PUBLICATIONS

Patrick C. May et al, Robust Central Reduction of Amyloid-Beta in Humans with an Orally Available, Non-Peptidic Beta-Secretase Inhibitor, The Journal of Neuroscience, Nov. 16, 2011, pp. 16507-16516. vol. 31(46).

*Primary Examiner* — Kahsay Habte
(74) *Attorney, Agent, or Firm* — Nelsen L. Lentz

(57) ABSTRACT

The present invention provides compounds of Formula I:

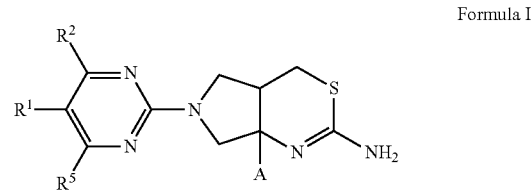

Formula I wherein A is selected from the group consisting of;

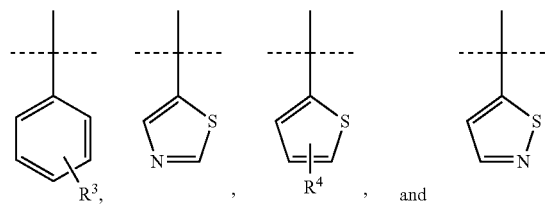

$R^1$ is H or F;
$R^2$ is H, —$CH_2OH$, C1-C3 alkyl,

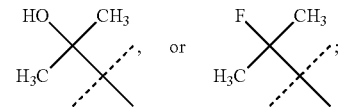

$R^3$ is H, F, or CN;
$R^4$ is H, F; or CN; and
$R^5$ is H, —$CH_3$, or —$OCH_3$;
or a pharmaceutically acceptable salt thereof.

12 Claims, No Drawings

TETRAHYDROPYRROLOTHIAZINE COMPOUNDS

The present invention relates to novel tetrahydropyrrolothiazine compounds, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Aβ) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Aβ in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Aβ peptide levels might result in a long-term significant reduction in plaque burden and synaptic deficits, thus providing significant therapeutic benefits, particularly in the treatment of Alzheimer's disease.

US 2009/0209755 discloses fused aminodihydrothiazine derivatives which possess BACE inhibitory activity and are further disclosed as useful therapeutic agents for a neurodegenerative disease caused by Aβ peptide, such as Alzheimer's type dementia. In addition, *J. Neuroscience*, 31(46), pages 16507-16516 (2011) discloses (S)-4-(2,4-difluoro-5-pyrimidin-5-yl-phenyl)-4-methyl-5,6-dihydro-4H-[1,3]thiazin-2-ylamine, an orally available CNS-active BACE inhibitor.

BACE inhibitors that are potent and efficacious with sufficient CNS penetration are desired to provide treatments for Aβ peptide-mediated disorders, such as Alzheimer's disease. The present invention provides certain novel compounds that are potent and efficacious inhibitors of BACE. In addition, the present invention provides certain novel compounds with CNS penetration and chemical stability.

Accordingly, the present invention provides compounds of Formula I:

Formula I

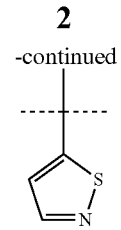

wherein A is selected from the group consisting of;

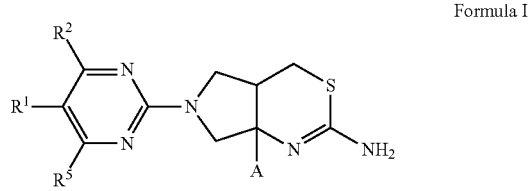

and

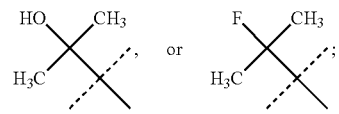

$R^1$ is H or F;
$R^2$ is H, —CH$_2$OH, C1-C3 alkyl,

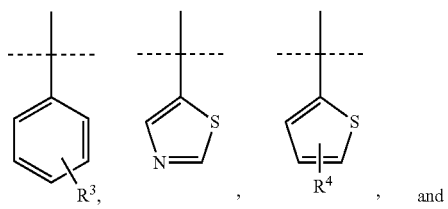

$R^3$ is H, F, or CN;
$R^4$ is H, F; or CN; and
$R^5$ is H, —CH$_3$, or —OCH$_3$;
or a pharmaceutically acceptable salt thereof.

The present invention also provides a method of treating Alzheimer's disease in a patient, comprising administering to a patient in need of such treatment an effective amount of a compound of Formula I, or a pharmaceutically acceptable salt thereof.

The present invention further provides a method of preventing the progression of mild cognitive impairment to Alzheimer's disease in a patient, comprising administering to a patient in need of such treatment an effective amount of a compound of Formula I, or a pharmaceutically acceptable salt thereof.

The present invention also provides a method of inhibiting BACE in a patient, comprising administering to a patient in need of such treatment an effective amount of a compound of Formula I, or a pharmaceutically acceptable salt thereof.

The present invention also provides a method for inhibiting BACE-mediated cleavage of amyloid precursor protein, comprising administering to a patient in need of such treatment an effective amount of a compound of Formula I, or a pharmaceutically acceptable salt thereof.

The invention further provides a method for the inhibition of production of Aβ peptide, comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy, in particular for the treatment of Alzheimer's disease or for the prevention of the progression of mild cognitive impairment to Alzheimer's disease. Even furthermore, this invention provides the use of a compound of Formula I, or a pharmaceutically acceptable salt thereof, for the manufacture of a medicament for the treatment of Alzheimer's disease. This invention also provides the use of a compound of Formula I, or a pharmaceutically acceptable salt thereof, for the manufacture of a medicament for the prevention of the progression of mild cognitive impairment to Alzheimer's disease. The invention also provides the use of a compound of Formula I, or a pharmaceutically acceptable salt thereof, for the manufacture of a medicament for the inhibition of BACE. The invention further provides the use of a compound of Formula I, or a pharmaceutically acceptable salt thereof, for the manufacture of a medicament for the inhibition of production of Aβ peptide.

The invention further provides a pharmaceutical composition, comprising a compound of Formula I, or a pharmaceutically acceptable salt thereof, in combination with one or more pharmaceutically acceptable carriers, diluents, or excipients. In a particular embodiment, the composition further comprises one or more other therapeutic agents. This invention also encompasses novel intermediates and processes for the synthesis of the compounds of Formula I.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

As used herein, the term "C1-C3 alkyl" refers to a C1-C3 alkyl group which includes, methyl, ethyl, propyl, isopropyl, and cyclopropyl. Preferred C1-C3 alkyl groups are ethyl, isopropyl, and cyclopropyl.

As used herein, the terms "treating" or "to treat" includes prohibiting, restraining, slowing, stopping, or reversing the progression or severity of an existing symptom or disorder.

As used herein, the term "patient" refers to a human.

The term "inhibition of production of Aβ peptide" is taken to mean decreasing of in vivo levels of Aβ peptide in a mammal.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formula I are particularly useful in the treatment methods of the invention, but certain groups, substituents, and configurations are preferred for compounds of Formula I. The following paragraphs describe such preferred groups, substituents, and configurations. It will be understood that these preferences are applicable both to the treatment methods and to the new compounds of the invention.

It is preferred that A is selected from the group consisting of:

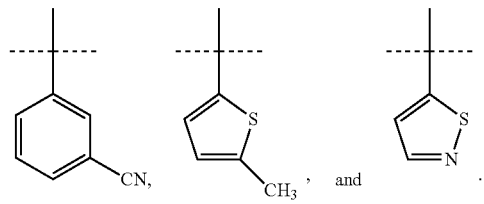

It is most preferred that A is selected from the group consisting of:

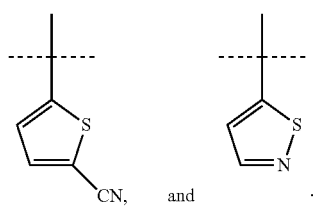

It is most especially preferred that A is:

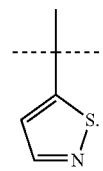

$R^1$ is preferably F.
$R^2$ is preferably H or

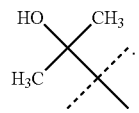

It is especially preferred that when $R^1$ is F, $R^2$ is H or

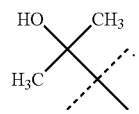

It is most especially preferred that when $R^1$ is F, $R^2$ is H.
It is especially preferred that when $R^1$ is F and $R^5$ is H, $R^2$ is H or

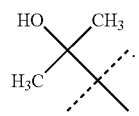

It is further especially preferred that when $R^1$ is F and $R^5$ is H, $R^2$ is H.

A preferred embodiment includes compounds of formula I that have improved CNS penetration.

Preferred compounds are:
(4aR,7aR)-6-(5-fluoropyrimidin-2-yl)-7a-isothiazol-5-yl-4,4a,5,7-tetrahydropyrrolo[3,4-d][1,3]thiazin-2-amine;
5-[(4aR,7aR)-2-amino-6-(5-fluoropyrimidin-2-yl)-4a,5,6,7-tetrahydropyrrolo[3,4-d][1,3]thiazin-7a(4H)-yl]thiophene-2-carbonitrile;
3-[(4aR,7aS)-2-amino-6-(5-fluoropyrimidin-2-yl)-4,4a,5,7-tetrahydropyrrolo[3,4-d][1,3]thiazin-7a-yl]benzonitrile;
2-[2-[(4aR,7aR)-2-amino-7a-isothiazol-5-yl-4,4a,5,7-tetrahydropyrrolo[3,4-d][1,3]thiazin-6-yl]-5-fluoro-pyrimidin-4-yl]propan-2-ol hydrochloride, isomer 2; and the pharmaceutically acceptable salts thereof.

Especially preferred compounds are:
(4aR,7aR)-6-(5-fluoropyrimidin-2-yl)-7a-isothiazol-5-yl-4,4a,5,7-tetrahydropyrrolo[3,4-d][1,3]thiazin-2-amine;
5-[(4aR,7aR)-2-amino-6-(5-fluoropyrimidin-2-yl)-4a,5,6,7-tetrahydropyrrolo[3,4-d][1,3]thiazin-7a(4H)-yl]thiophene-2-carbonitrile; and the pharmaceutically acceptable salts thereof.

A most especially preferred compound is:
(4aR,7aR)-6-(5-fluoropyrimidin-2-yl)-7a-isothiazol-5-yl-4,4a,5,7-tetrahydropyrrolo[3,4-d][1,3]thiazin-2-amine, and the pharmaceutically acceptable salts thereof.

One of ordinary skill in the art will appreciate that compounds of the invention can exist in tautomeric forms, as depicted in Scheme A. When any reference in this application to one of the specific tautomers of the compounds of the invention is given, it is understood to encompass both tautomeric forms and all mixtures thereof.

Scheme A

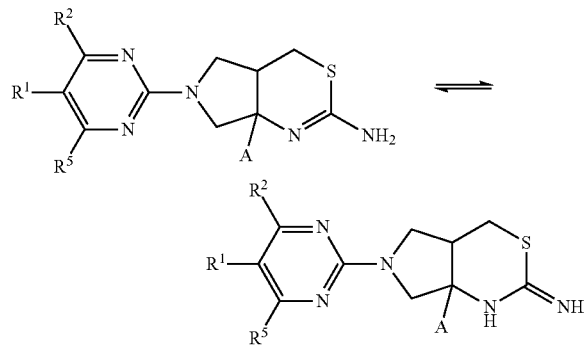

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I, or salts thereof. The products of each step in the schemes below can be recovered by conventional methods, including extraction, evaporation, precipitation, chromatography, filtration, trituration, and crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated or resolved by one of ordinary skill in the art at any convenient point in the synthesis of compounds of Formula I by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples. Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

One of ordinary skill in the art will appreciate that compounds of the invention are comprised of a core that contains at least two chiral centers:

Scheme B

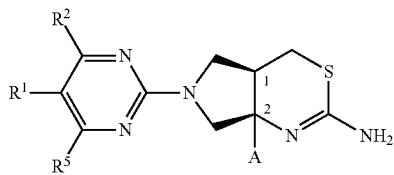

Although the present invention contemplates all individual enantiomers, as well as mixtures of the enantiomers of said compounds, including racemates, the compounds with the absolute configuration at the atoms labeled 1 and 2 as illustrated in Scheme B are preferred compounds of the invention.

Abbreviations used herein are defined according to *Aldrichimica Acta*, Vol. 17, No. 1, 1984. Other abbreviations are defined as follows: "APP" refers to amyloid precursor protein; "BOC" refers to tert-butyloxycarbonyl; "CSF" refers to cerebrospinal fluid; "DCC" refers to 1,3-dicyclohexylcarbodiimide; "DCM" refers to dichloromethane; "DIC" refers to diisopropylcarbodiimide; "DMEM" refers to Dulbecco's Modified Eagle's Medium; "DMSO" refers to dimethylsulfoxide; "EDCI" refers to 1-(3-dimethylaminopropyl)-3-ethylcarbodiimide hydrochloride; "ee" refers to enantiomeric excess; "EtOAc" refers to ethyl acetate; "Ex" refers to example; "F12" refers to Ham's F12 medium; "FBS" refers to Fetal Bovine Serum; "FRET" refers to fluorescence resonance energy transfer; "HEK" refers to human embryonic kidney; "HOAc" refers to acetic acid; "HOAt" refers to 1-hydroxy-7-azobenzotriazole; "HOBt" refers to 1-hydroxylbenzotriazole hydrate; "HPLC" refers to high-performance liquid chromatography; "hr refers to hour or hours; "IC$_{50}$" refers to the concentration of an agent that produces 50% of the maximal inhibitory response possible for that agent; "IPA" refers to isopropyl alcohol or isopropanol; "MeOH" refers to methyl alcohol or methanol; "min" refers to minute or minutes; "MTBE" refers to methyl tert-butyl ether; "PDAPP" refers to platelet derived amyloid precursor protein; "Prep" refers to preparation; "RFU" refers to relative fluorescence unit "R$_t$" refers to retention time; "RT" refers to room temperature; "SCX" refers to strong cation exchange; "THF" refers to tetrahydrofuran and "TLC" refers to thin layer chromatography.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

Alternatively, the carboxylic acid can be converted to the acid chloride and the Weinreb amide can be formed using an organic base and N,O-dimethylhydroxylamine hydrochloride.

Subsequent treatment of the Weinreb amide with an organometallic reagent such as a heterocyclic Grignard reagent or an organolithium reagent gives compound 3, Step 2. For example, a heterocyclic halide and alkyl Grignard or organolithium reagent can be used to form a ketone with the desired (A) group attached, (3, Step 2). The ketone (3) can then be used to form an oxime with hydroxylamine hydrochloride

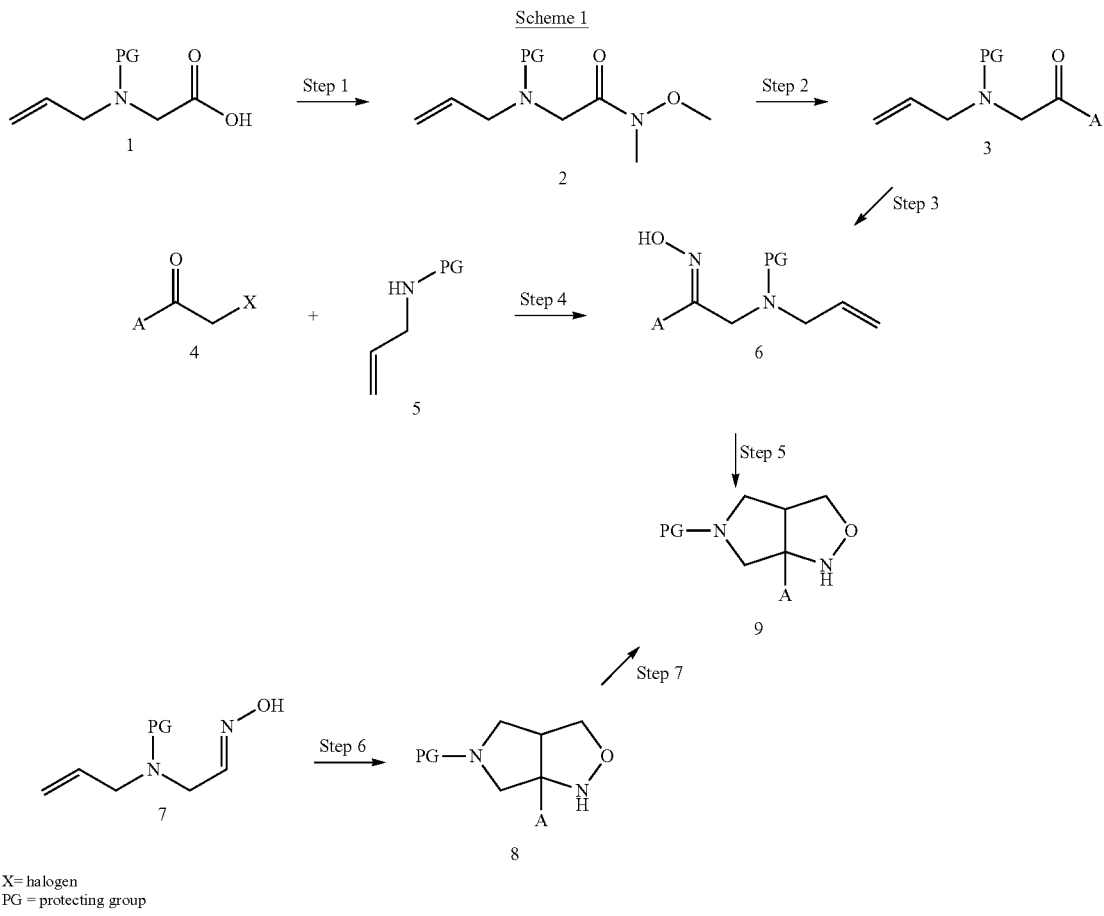

X= halogen
PG = protecting group

Scheme 1 depicts the formation of the Weinreb amide (2) used to form a ketone (3) that can then be transformed to an oxime. The oxime can be used to form the bicyclic isoxazole (9). The (A) group can be inserted at different points of the synthesis as shown in Scheme 1. "PG" is a protecting group developed for the amino group, such as carbamates and allyl. Such groups are well known and appreciated in the art.

A compound of formula (1) is converted to the Weinreb amide (Step 1, compound 2) with N,O-dimethylhydroxylamide hydrochloride using an organic base such as diisopropylethylamine or triethylamine and coupling reagents such as carbodiimides and HOBt or HOAt to improve the efficiency of amide coupling. One skilled in the art will recognize that there are a number of methods and reagents for amide formation resulting from the reaction of carboxylic acids and amines. For example, useful carbodiimides are DCC, DIC, EDCI.

and an inorganic base such as sodium acetate trihydrate or sodium acetate or an organic base such as pyridine in a polar protic solvent such as ethanol or water to give compound 6, Step 3. Alternatively, in a 2-step reaction, a ketone with a beta halogen can be alkylated with a protected allyl amine and then treated with hydroxylamine hydrochloride to give the oxime, (6, Step 4). The oxime, (6) can then be converted to the bicyclic isoxazole (9) in a 3+2 cyclization by several methods such as heating the oxime (6) in a non-polar solvent such as toluene or xylene to form compound 9, Step 5 or using an aqueous solution of sodium hypochlorite or titanium (IV) ethoxide in an non-polar solvent such as toluene or xylene with heating to give compound 9, Step 5 or compound 8, Step 6. Compound 8 can then be alkylated using an aromatic or heteroaromatic organolithium reagent or Grignard reagent to give compound 9, Step 7.

Scheme 2

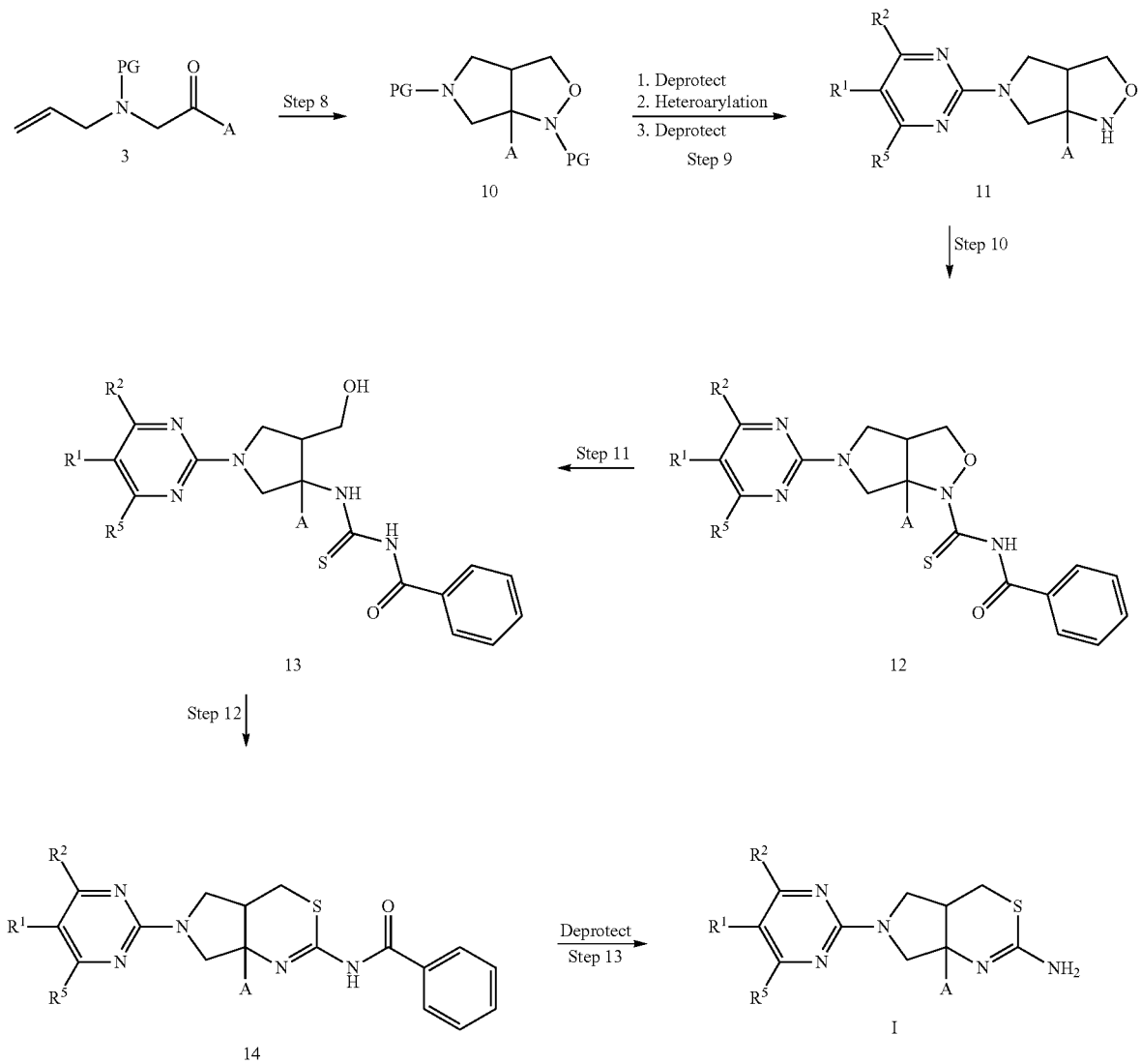

Scheme 2 illustrates the in situ formation of the oxime and subsequent conversion to form the bicyclic isoxazole to give compound (10), Step 8. N-[(4-methoxyphenylmethyl]hydroxylamine hydrochloride is treated with compound (3) in an organic base such as triethylamine to which titanium (IV) ethoxide is added and with heating gives compound 10. A BOC protected pyrrolidine of the bicyclic isoxazole is deprotected under acidic conditions well known in the art. An allyl protected pyrrolidine can be deprotected using an acid such as N,N-dimethylbarbituric acid with a catalyst such as tetrakis (triphenylphosphine)palladium. The carboxybenzyl protected pyrrolidine can be deprotected using iodotrimethylsilane. The deprotected pyrrolidine can then be reacted in a nucleophilic aromatic substitution reaction (SNAr) with a substituted or unsubstituted aromatic pyrimidine using an organic base such as diisopropylethylamine, triethylamine, or N,N,N',N'-tetramethylguanidine to give the desired substituted protected bicyclic isoxazole (Steps 1 and 2 of Step 9). The protecting group of the bicyclic isoxazole, 4-methoxyl benzyl (PMB), is subsequently deprotected under acidic conditions to give compound 11, (Step 3 of Step 9). Compound 11 is treated with benzoyl isothiocyanate in a polar aprotic solvent such as THF to give the thiourea (12, Step 10). The isoxazole ring can be opened with powdered zinc in HOAc or Raney Ni under hydrogenation conditions, (13, Step 11). The hydroxy compound (13) is then treated with 1-chloro-N,N,2-trimethylpropenylamine or 1,1' carbonyldiimidazole to form the fused pyrrolidine protected thiazine (14, Step 12). The thiazine amide can be deprotected with an organic base such as pyridine and methylhydroxylamine hydrochloride in a polar aprotic solvent such as ethanol or an inorganic base such as lithium hydroxide in methanol to give compounds of Formula I in Step 13.

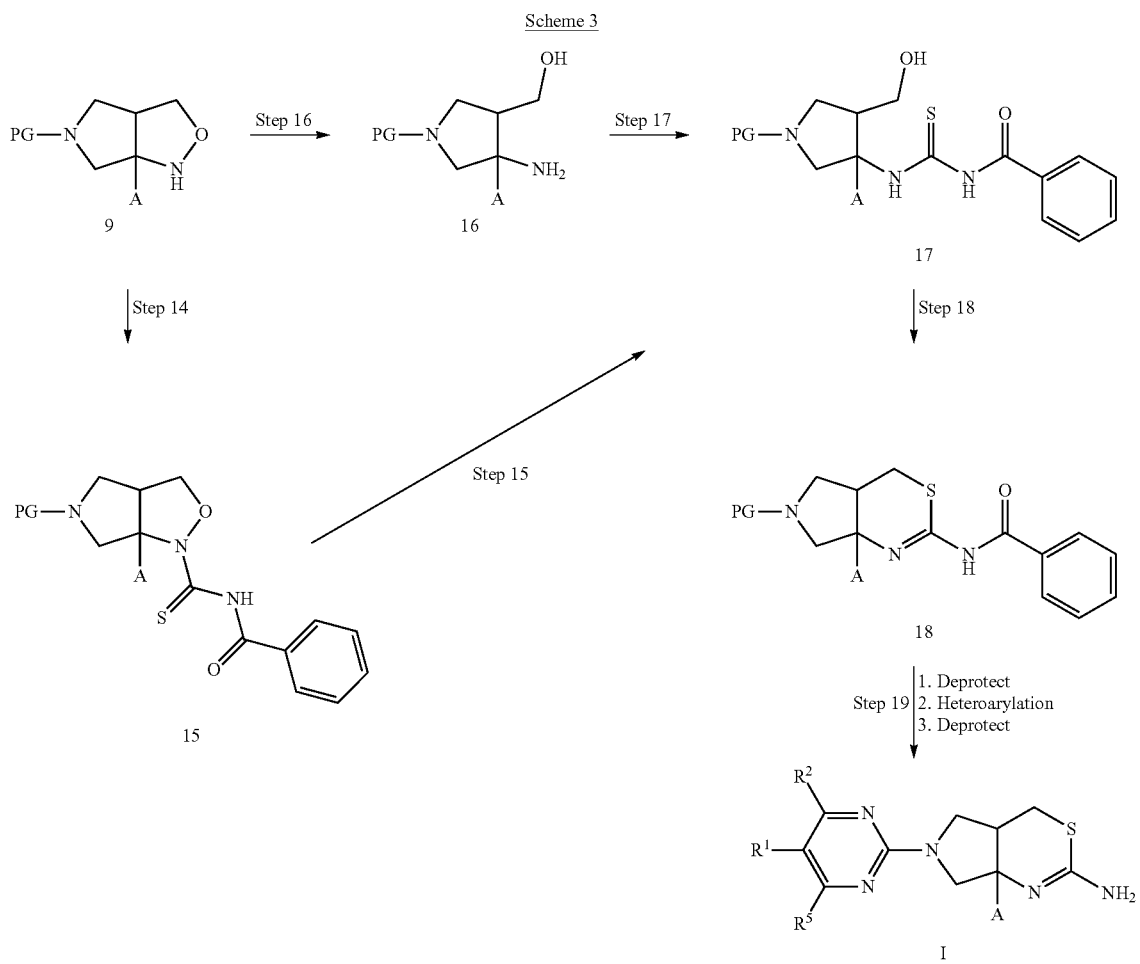

Scheme 3 depicts the protected bicyclic isoxazole (9) that can be treated with benzothioisocyanate to give compound (15, Step 14), treated with powdered zinc in HOAc to give compound (17, Step 15), and then the thiazine ring formed as described in Scheme 2, Step 12 to give compound 18, Step 18. In Step 19, the pyrrolidine (18) can be deprotected and heteroarylated as described in Scheme 2 (Steps 1 and 2 of Step 9) to give the fused pyrrolidine protected thiazine (Compound 14, Scheme 2). The thiazine amide can then be deprotected as described in Scheme 2 (Step 13) to give compounds of Formula I. Alternatively, the protected bicyclic isoxazole can first be treated with powdered Zn in HOAc or Raney Ni under hydrogenation conditions (16, Step 16,) followed by reaction with benzothioisocyanate to give compound 17, Step 17. Compounds of Formula I can then be prepared in Steps 18 and 19 as described above.

In an optional step, a pharmaceutically acceptable salt of a compound of Formula I can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that the compound of Formula 1 is readily converted to and may be isolated as a pharmaceutically acceptable salt, such as a hydrochloride salt.

PREPARATIONS AND EXAMPLES

The following preparations and examples further illustrate the invention. Unless noted to the contrary, the compounds illustrated herein are named and numbered using Symyx® Draw version 3.2 (Symyx Solutions, Inc.) or IUPACNAME ACDLAB S.

Preparation 1

2-Chloro-5-fluoro-4-isopropyl-pyrimidine

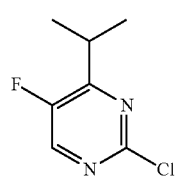

A solution of 5-fluoro-2-chloropyrimidine (5.00 g, 37.7 mmol) in 1,2-dimethoxyethane (25 mL) is treated with a solution of 2 M isopropyl magnesium chloride in tetrahydrofuran (28.3 mL, 56.6 mmol) while keeping the temperature below 15° C. The resulting solution is stirred for one hour under nitrogen and then cooled to 0° C. and treated drop wise with a solution of triethylamine (5.76 mL, 37.7 mmol) in tetrahydrofuran (5 mL). A solution of iodine (9.58 g, 37.7 mmol) in tetrahydrofuran (20 mL) is added. The reaction is quenched with water and saturated sodium bicarbonate and saturated sodium bisulfate are added. The mixture is extracted three times with ethyl acetate. The combined organic layers are dried over sodium sulfate and the solvent is removed under vacuum. The crude product is purified over silica gel with a 30 minute gradient, dichloromethane/hexanes (5 to 100%) to give the title compound (2.55 g, 39%). GC/MS (m/e): 174.

The following compound is prepared essentially by the method of Preparation 1 using ethylmagnesium bromide (3.0 M in diethyl ether).

TABLE 1

| Prep. No. | Chemical name | Structure | Physical data |
|---|---|---|---|
| 2 | 2-Chloro-4-ethyl-5-fluoro-pyrimidine | 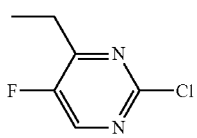 | $^1$H-NMR (CDCl$_3$): δ (ppm) 1.32 (t, 3H), 2.86 (m, 2H), 8.34 (d, 1H) |

Preparation 3

1-(2-Chloro-5-fluoro-pyrimidin-4-yl)ethanone

A solution of 5-fluoro-2,4-dichloro-pyrimidine (20 g, 119.8 mmol) and (1-ethoxyethenyl)trimethylstannane (43.26 g, 119.8 mmol) in dimethylformamide (200 mL) is purged at room temperature with nitrogen and bis(triphenylphosphine)palladium(II) chloride (1.70 g, 2.40 mmol) is then added. The resulting mixture is heated at 70° C. for 2 hours under nitrogen. The reaction is cooled to 50° C. and aqueous 5 N hydrogen chloride (100 mL) is added. The reaction is stirred at 50° C. for two more hours. The reaction is cooled, diluted with water (200 mL) and brine. This solution is extracted five times with diethyl ether. The combined organic layers are dried over sodium sulfate and concentrated under vacuum. The crude product is purified over silica gel with a 30 minute, 5% to 50% ethyl acetate in hexanes gradient, to give the title compound (19.2 g, 92%). GC/MS (m/e): ($^{35}$Cl/$^{37}$Cl) 174/176.

Preparation 4

2-(2-Chloro-5-fluoro-pyrimidin-4-yl)propan-2-ol

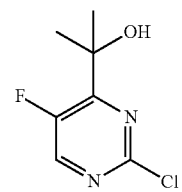

A stirred, −78° C. solution of 1-(2-chloro-5-fluoro-pyrimidin-4-yl)ethanone (10.06 g, 57.6 mmol) in tetrahydrofuran (100 mL) under nitrogen is reacted with a 3 M solution of methyl magnesium bromide in diethyl ether (124 mL, 72.04 mmol) and the resulting mixture is stirred at −78° C. for 20 minutes. The reaction is quenched with aqueous saturated ammonium chloride and the mixture is warmed to room temperature. The reaction mixture is extracted three times with ethyl acetate. The combined organic layers are dried over sodium sulfate and concentrated under vacuum. The crude product is purified over silica gel with a 30 minute, 5% to 100% ethyl acetate in hexanes gradient, to give the title compound (7.06 g, 64%). ES/MS (m/e): ($^{35}$Cl/$^{37}$Cl) 191/193 (M+H).

Preparation 5

2-(2-Chloro-5-fluoro-pyrimidin-4-yl)propan-2-ol

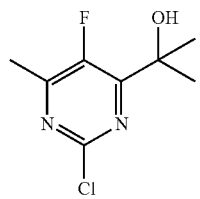

To a solution of methylmagnesium bromide (3.0 M in diethyl ether, 2.20 mL, 6.60 mmol) in THF (5.0 mL) at 0° C. is added a solution of 2-(2-chloro-5-fluoro-pyrimidin-4-yl)propan-2-ol (510 mg, 2.68 mmol) in 1,2-dimethoxyethane (4.0 mL) drop wise over 4 min. After 5 min, the ice bath is removed. After stirring at room temperature for 40 min, additional methylmagnesium bromide (3.0 M in diethyl ether, 1.10 mL, 3.30 mmol) is added, and the solution is cooled to 0° C. again for 30 minutes followed by the addition of triethylamine (400 μL, 2.87 mmol) and solution of iodine (700 mg, 2.74 mmol) in THF (2.7 mL). The solution is stirred at room temperature for 20 hrs, quenched with ½ saturated NaHCO$_3$ (40 mL) and extracted with CHCl$_3$ (2×20 mL). The combined organic layers are dried over magnesium sulfate, filtered, and concentrated to dryness. The residue is purified by silica gel flash chromatography, eluting with a gradient of ethyl acetate/dichloromethane (0% to 30%) to give the title compound (200 mg, 37%). $^{19}$F-NMR (CDCl$_3$): δ (ppm)-137.6. $^1$H-NMR (CDCl$_3$): δ (ppm) 4.39 (s, 1H), 2.55 (s, 3H), 1.59 (s, 6H).

Preparation 6

2-Chloro-5-fluoro-4-(1-fluoro-1-methyl-ethyl)pyrimidine

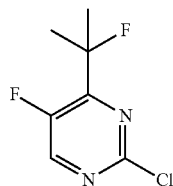

Diethylaminosulfur trifluoride (6.53 g, 40.5 mmol) is added drop wise to a −78° C. solution of 2-(2-chloro-5-fluoro-pyrimidin-4-yl)propan-2-ol (4.825 g, 25.31 mmol) in dichloromethane (70 mL) under nitrogen. The reaction is stirred at −78° C. for 30 minutes under nitrogen, is then quenched with aqueous saturated sodium bicarbonate and is warmed to room temperature. The reaction mixture is extracted three times with ethyl acetate. The combined organic layers are dried over sodium sulfate and concentrated under vacuum. The resulting crude product is purified over silica gel with a 40 minute, 5% to 100% ethyl acetate in hexanes gradient to give the title compound (4.23 g, 87%). ES/MS (m/e): ($^{35}$Cl/$^{37}$Cl) 193/195 (M+H).

Preparation 7

(2-Chloro-5-fluoro-pyrimidin-4-yl)methanol

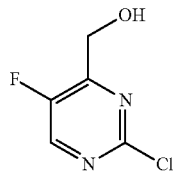

To a solution of 5-fluoro-2-chloropyrimidine (500 μL, 5.24 mmol) in methanol (50 mL) is added benzoyl peroxide (1.5 g, 6.0 mmol) and trifluoroacetic acid (450 μL, 5.95 mmol). The resulting colorless clear solution is degassed by bubbling nitrogen through for 5 minutes and it is then heated at 65° C. for 18.5 hours. The solution is then cooled and concentrated. The resulting residue is diluted with chloroform (50 mL) and washed with saturated aqueous sodium bicarbonate solution (50 mL) and the layers are separated. The aqueous layer is re-extracted with chloroform (50 mL). The combined organic layers are dried over magnesium sulfate, filtered and concentrated to dryness under reduced vacuum. The residue is purified by flash silica gel column chromatography, eluting with gradient of ethyl acetate/dichloromethane (0% to 30%) to give the title compound (210 mg, 25%). $^1$H-NMR (CDCl$_3$): δ (ppm) 8.42 (s, 1H), 4.85 (s, 2H), 3.57 (br, 1H).

Preparation 8

5-Fluoro-N-methoxy-N-methylthiophene-2-carboxamide

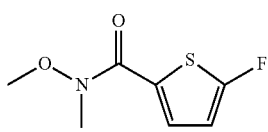

To a stirred solution of 5-fluorothiophene-2-carboxylic acid (33.95 g, 232.3 mmol) in tetrahydrofuran (465 mL) at 0° C. under nitrogen is added N,O-dimethylhydroxylamine hydrochloride (45.32 g, 464.6 mmol), 1-hydroxybenzotriazole monohydrate (53.36 g, 348.5 mmol), 1-(3-dimethylaminopropyl)-3-ethylcarbodiimide hydrochloride (89.1 g, 464.6 mmol), and diisopropylethylamine (162 mL, 929 mmol). The mixture is allowed to warm to room temperature over 18 hours. The mixture is diluted with water (500 mL) and extracted with ethyl acetate (500 mL). The aqueous phase is re-extracted twice with ethyl acetate (300 mL). The combined organic extracts are dried over sodium sulfate, filtered, and concentrated under reduced pressure. The liquid residue is purified by silica gel chromatography eluting with hexanes/ethyl acetate (3:1) to give the title compound (38.28 g, 87%) as a pale yellow liquid. ES/MS (m/e): 190 (M+H).

The following compound is prepared essentially by the method of preparation 8 using the appropriate thiazole carboxylic acid.

TABLE 2

| Prep. No. | Chemical name | Structure | $^1$H NMR (CDCl$_3$) δ |
|---|---|---|---|
| 9 | N-Methoxy-N-methyl-thiazole-5-carboxamide[a] | 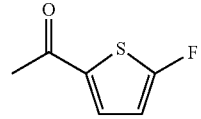 | 3.35 (s, 3H), 3.74 (s, 3H), 8.62 (s, 1H), 8.91 (s, 1H). |

[a]Dichloromethane used instead of THF at room temperature.

Preparation 10

1-(5-Fluorothiophen-2-yl)ethanone

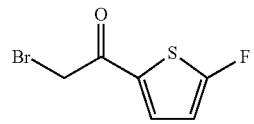

To a stirred solution of 5-fluoro-N-methoxy-N-methylthiophene-2-carboxamide (12.34 g, 65.2 mmol) in tetrahydrofuran (163 mL) at 0° C. under nitrogen is added methyl magnesium bromide (3 M solution in tetrahydrofuran, 32.6 mL, 97.8 mmol) over a period of 25 minutes, while maintaining the internal temperature below 10° C. The cooling bath is removed and the solution is allowed to warm to room temperature over 1 hour. A saturated solution of ammonium chloride (200 mL) is added and the mixture is stirred for 10 minutes. The mixture is diluted with diethyl ether (200 mL) and the phases are separated. The aqueous phase is re-extracted with diethyl ether (2×150 mL) and the combined organic extracts are dried over sodium sulfate, filtered, and concentrated under reduced pressure (keeping the water bath below 25° C.) to give the crude title compound (9.70 g, 103%) as a pale amber liquid. $^1$H NMR (CDCl$_3$) δ 2.47 (s, 3H), 6.53 (dd, J=1.2, 4.3 Hz, 1H), 7.38 (t, J=4.0 Hz, 1H).

Preparation 11

2-Bromo-1-(5-fluorothiophen-2-yl)ethanone

To a stirred clear amber solution of 1-(5-fluorothiophen-2-yl)ethanone (9.70 g, 67.3 mmol) in dichloromethane (224 mL) at 0° C. under nitrogen is added diisopropylethylamine (14.7 mL, 84.1 mmol) followed by the drop wise addition of trimethylsilyl trifluoromethanesulfonate (13.8 mL, 74.0 mmol) over 10 minutes while maintaining the internal temperature below 5° C. The resulting solution is stirred at 0° C. for 90 minutes. N-bromosuccinimide (13.17 g, 74.0 mmol) is added in one portion and the resulting orange solution is stirred at 0° C. for 1 hour. Dilute aqueous sodium bicarbonate (200 mL of a 1:1 water/saturated aqueous sodium bicarbonate solution) and dichloromethane (50 mL) are added. The phases are separated and the aqueous phase is re-extracted with dichloromethane (150 mL). The combined organic extracts are dried over sodium sulfate, filtered, and concentrated under reduced pressure to give a red oily/amorphous residue. The residue is diluted with hexanes (50 mL) and dichloromethane (5 mL) and filtered to remove solids. The solids are washed with a solution of hexanes/dichloromethane (~50 mL, 7:3). The combined filtrates are concentrated under reduced pressure and the residue is purified by silica gel chromatography eluting with hexanes/dichloromethane (two-step gradient from 70:30 to 60:40 to 50:50) to give the title compound (13.33 g, 89%). $^1$H NMR (CDCl$_3$) δ 4.27 (s, 2H), 6.58 (dd, J=1.3, 4.4 Hz, 1H), 7.52 (dd, J=1.5, 4.2 Hz, 1H).

Preparation 12

1-(4-Bromo-2-thienyl)-2-(diallylamino)ethanone

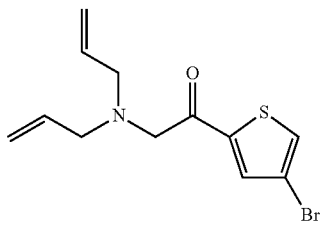 [SMILES: C=CCN(CC=C)CC(=O)c1cc(Br)cs1]

To 1-(4-bromothiophen-2-yl)ethanone (10 g, 48.8 mmol) in methanol (98 mL) and dichloromethane (163 mL) is added tetra-n-butylammonium tribromide (28.8 g, 58.5 mmol). The reaction mixture is concentrated under reduced pressure at 50° C. to give a residue which is purified by silica gel chromatography, eluting with dichloromethane to give crude 2-bromo-1-(4-bromo-2-thienyl)ethanone. To a solution of the crude 2-bromo-1-(4-bromo-2-thienyl)ethanone in acetonitrile (200 ml) is added potassium carbonate (20.2 g, 146 mmol) and diallylamine (9.48 g, 97.5 mmol). The reaction is stirred at room temperature for 2 hours. Water is added and the solution is extracted with ethyl acetate. The organic phases are combined, dried over sodium sulfate, filtered, and concentrated under reduced pressure to give the crude title compound. ES/MS (m/e): ($^{79}$Br/$^{81}$Br) 300/302 (M+H).

Preparation 13

2-(Diallylamino)-1-(5-fluoro-2-thienyl)ethanone

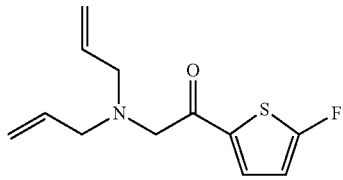 [SMILES: C=CCN(CC=C)CC(=O)c1ccc(F)s1]

To a stirred solution of 2-bromo-1-(5-fluorothiophen-2-yl)ethanone (13.28 g, 59.53 mmol) in acetonitrile (298 mL) at 0° C. under nitrogen is added potassium carbonate (10.70 g, 77.39 mmol) and diallylamine (9.54 mL, 77.39 mmol). The mixture is allowed to slowly warm to room temperature with stirring over 16 hours then diluted with ethyl acetate (500 mL) and water (200 mL). The phases are separated and the aqueous phase extracted twice with ethyl acetate (100 mL). The combined organic extracts are dried over sodium sulfate, filtered, and concentrated under reduced pressure. The residue is purified by silica gel chromatography eluting with hexanes/ethyl acetate (9:1) to give the title compound (12.45 g, 87%) as a yellow oil. ES/MS (m/e): 240 (M+H).

The following compound is prepared essentially by the method of Preparation 13 using the appropriate ethanone and no potassium carbonate is used.

TABLE 3

| Prep. No. | Chemical name | Structure | Physical data |
|---|---|---|---|
| 14 | 2-(Diallylamino)-1-thiazol-5-yl-ethanone | 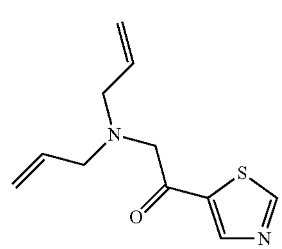 | $^1$HNMR (CDCl$_3$). δ (ppm) 3.15 (d, J = 6.4, 4H), 3.72 (s, 2H), 5.10 (m, 4H), 5.81 (m, 2H), 8.67 (s, 1H), 9.30 (s, 1H). |

Preparation 15

2-(Diallylamino)-1-(4-fluorophenyl)ethanone

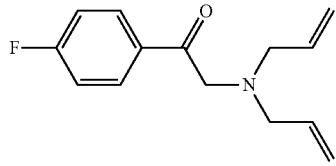 [SMILES: C=CCN(CC=C)CC(=O)c1ccc(F)cc1]

2-Chloro-1-(4-fluorophenyl)ethanone (10 g, 57.4 mmol) is dissolved in acetonitrile (400 mL). The solution is cooled to 0° C. and diallylamine (15.6 mL, 126.2 mmol) is added. After 1 hour, the mixture is poured into water (500 mL) and extracted twice with ethyl acetate (400 mL). The organic extracts are combined, washed with brine (1×200 mL), dried over sodium sulfate, filtered, and concentrated to give the crude title compound (15.84 g, 118%). ES/MS (m/e): 234 (M+H).

Preparation 16

2-(Diallylamino)-1-(4-fluorophenyl)ethanone oxime

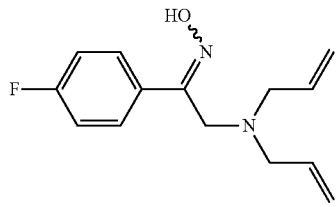 [SMILES: C=CCN(CC=C)CC(=NO)c1ccc(F)cc1]

2-(Diallylamino)-1-(4-fluorophenyl)ethanone (13.38 g, 57.36 mmol) is dissolved in ethanol (250 mL) and sodium acetate (5.7 g) is added followed by hydroxylamine hydrochloride (5.23 g, 74.6 mmol). The reaction is warmed to 70° C. for 2.5 hours then stirred at room temperature for 16 hours. The mixture is concentrated and the resulting residue is purified by silica gel flash chromatography eluting with ethyl acetate/hexanes (gradient 0-100%). The isolated material is repurified a second time to give the title compound (7.76 g, 54.5%). ES/MS (m/e): 249 (M+H).

Preparation 17

2-(Allyl(tert-butoxycarbonyl)amino)acetic acid

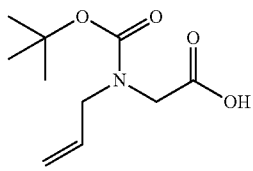

To an Erlenmeyer flask containing potassium carbonate (100 g, 724 mmol), sodium iodide (110 g, 727 mmol), dimethylformamide (300 mL), triethylamine (200 mL, 1.44 mole) and 2-propen-1-amine (24 g, 426 mmol) at 0° C. is added drop wise a solution of ethyl 2-bromoacetate (60.2 g, 360 mmol) in dimethylformamide (40 mL). The reaction is warmed to ambient temperature and stirred overnight. The mixture is filtered, washed with diethyl ether (200 mL), and concentrated. Brine (1 L) is added to the filtrate and the layers are separated. The aqueous layer is extracted with diethyl ether (3×500 mL). The organic phases are combined, dried over magnesium sulfate, filtered, and the solvent removed under reduced pressure to give a residue. To a solution at 0° C. of crude residue in ethanol (500 ml) and triethylamine (40 g, 395 mmol) is added di-t-butyldicarbonate (105 g, 467 mmol) in one portion. The reaction is warmed to room temperature and stirred overnight. The reaction is concentrated under reduced pressure, diluted with water (200 mL) and saturated sodium bicarbonate (200 mL), and extracted with ethyl acetate (2×200 mL) and dichloromethane (200 mL). The organic phases are combined, dried over magnesium sulfate, filtered, and concentrated under reduced pressure to give a crude residue. The crude residue is taken up in methanol (200 mL) and 2 N sodium hydroxide (500 mL) is added and the mixture is stirred for approximately 3 hours at room temperature. The solution is concentrated under reduced pressure and the resulting aqueous solution acidified to pH 4 with 12 N hydrochloric acid. The resulting precipitate is collected by filtration, washed with water, and dried to give the title compound (50 g, 65%). $^1$H NMR (CDCl$_3$) mixture of two rotamers (50:50) δ 1.43, 1.45 (s, 9H), 3.86-3.99 (m, 4H), 5.10-5.20 (m, 2H), 5.71-5.83 (m, 1H).

Preparation 18 tert-Butyl N-allyl-N-[2-(methoxy(methyl)amino)-2-oxo-ethyl]carbamate

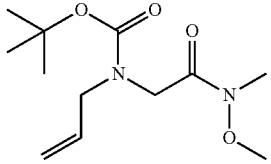 [SMILES: C=CCN(CC(=O)N(C)OC)C(=O)OC(C)(C)C]

2-(Allyl(tert-butoxycarbonyl)amino)acetic acid (49.6 g, 156 mmol), tetrahydrofuran (600 mL), and triethylamine (36.3 g, 359 mmol) is added to an Erlenmeyer flask and the mixture is cooled to 0° C. Pivaloyl chloride (31 g, 253 mmol) is added drop wise and the reaction is stirred at room temperature for 3 hours and then cooled to 0° C. N,O-dimethylhydroxylamine hydrochloride (28 g, 283 mmol), triethylamine (33 mL, 237 mmol) and tetrahydrofuran (400 mL) are then added. The ice bath is removed and the reaction is stirred at room temperature for 3 hours. The mixture is concentrated under reduced pressure. The resulting residue is dissolved in water (300 mL) and extracted with ethyl acetate (2×300 mL). The organic phases are combined, dried over magnesium sulfate, filtered, and concentrated under reduced pressure to give a residue. The residue is purified by silica gel flash chromatography, eluting with hexane/acetone (1:0) to hexane/acetone (1:1) to give the title compound (32 g, 54%). $^1$H NMR (CDCl$_3$) mixture of two rotamers (60:40) δ 1.42, 1.44 (s, 9H), 3.16, 3.17 (s, 3H), 3.66, 3.69 (s, 3H), 3.88-3.98 (m, 2H), 4.01, 4.11 (s, 2H), 5.10-5.18 (m, 2H), 5.73-5.85 (m, 1H).

Preparation 19 tert-Butyl N-allyl-N-phenacyl-carbamate

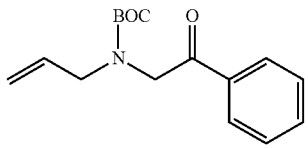 [SMILES: C=CCN(CC(=O)c1ccccc1)C(=O)OC(C)(C)C]

To a solution of tert-butyl N-allyl-N-[2-(methoxy(methyl)amino)-2-oxo-ethyl]carbamate (4.0 g, 15.5 mmol) in THF (54 mL) cooled to −20° C. is added drop wise phenyl magnesium bromide (10.3 ml, 3 M in diethyl ether). The reaction is monitored by TLC, carefully quenched with saturated ammonium chloride in water (20 mL), diluted with water (100 mL) and extracted with dichloromethane. The organic layers are combined, dried over sodium sulfate, filtered, and concentrated under reduced pressure to give a residue. The residue is purified by silica gel flash chromatography, eluting with hexane/ethyl acetate (1:0) to hexane/ethyl acetate (5:1) to give the title compound (3.2 g, 75%). $^1$H NMR (CDCl$_3$) Mixture of two rotamers (51:49) δ 1.47, 1.35 (s, 9H), 3.91, 3.99 (d, 2H), 4.52, 4.65 (s, 2H), 5.07-5.16 (m, 2H), 5.72-5.87 (m, 1H), 7.41-7.50 (m, 2H), 7.52-7.60 (m, 1H), 7.88-7.95 (m, 2H).

Preparation 20 tert-Butyl N-allyl-N-(2-isothiazol-5-yl-2-oxo-ethyl)carbamate

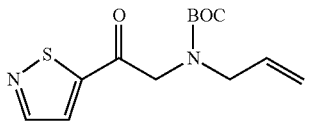 [SMILES: C=CCN(CC(=O)c1ccns1)C(=O)OC(C)(C)C]

To a −78° C. solution of diisopropylamine (9.01 mL, 64.01 mmol) in tetrahydrofuran (80 mL) is added n-butyl lithium (30.78 mL, 49.24 mmol, 1.6 M in hexanes) drop wise under nitrogen. The resulting solution is stirred at −78° C. for 20 minutes and then a solution of isothiazole (4.19 g, 49.24 mmol) in tetrahydrofuran (10 mL) is added drop wise. The resultant white slurry is stirred for 30 minutes at −78° C. A solution of tert-butyl N-allyl-N-[2-(methoxy(methyl)amino)-2-oxo-ethyl]carbamate (6.36 g, 24.62 mmol) in tetrahydrofuran (50 mL) is then added to the slurry over a 15 minutes period. The reaction is then stirred for 30 minutes at −78° C., warmed to ambient temperature and is stirred for 30 minutes. Saturated ammonium chloride (200 mL) is then added. The resulting solution is extracted three times with ethyl acetate. The combined organic layers are dried over sodium sulfate, filtered, and concentrated under vacuum. The crude product is purified over silica gel with a 35 minute, 5% to 100% ethyl acetate in hexanes gradient, to give the title compound (6.00 g, 21.25 mmol, 86%). ES/MS (m/e): 283.0 (M+H).

Alternate Preparation 20

Diisopropylamine (852.89 mL, 6.06 mol) is dissolved in tetrahydrofuran (6.02 L) and the solution is cooled to −40° C. Butyl lithium (2.5 M in hexanes, 1.86 L, 4.66 mol) is added drop wise to the mixture over 60 minutes. The yellow clear solution is stirred at −40° C. for 45 minutes under nitrogen. A solution of isothiazole (396.78 g, 4.66 mol) in tetrahydrofuran (1.20 L) is added drop wise, over 30 minutes. The resulting brown slurry is stirred at −40° C. for 45 minutes. The slurry is treated with a solution of tert-butyl N-allyl-N-[2-[methoxy(methyl)amino]-2-oxo-ethyl]carbamate (602 g, 2.33 mol) in tetrahydrofuran (2.41 L) over 40 minutes at −40° C. The reaction is warmed to 0° C. over 40 minutes and stirred at this temperature for 40 minutes. The reaction is quenched with saturated NH$_4$Cl (4.0 L) and the mixture is stirred overnight. Ethyl acetate (3.0 L) is added and the mixture is separated. The aqueous phase is extracted with ethyl acetate (3×1.5 L), and the combined organic layers are washed with water (2×3 L), brine, dried over sodium sulfate, filtered, and the solvent is removed under reduced pressure to give the crude product, a dark brown oil. The crude material is purified by silica gel (3 Kg), eluting with 0% to 10% ethyl acetate in DCM. The product is isolated as an amber oil (610.1 g, 92.7%). ES/MS (m/e): 283 (M+H).

Preparation 21 tert-Butyl N-allyl-N-[2-oxo-2-(2-thienyl)ethyl]carbamate

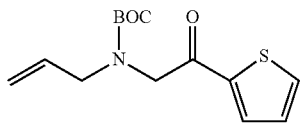 [SMILES: C=CCN(CC(=O)c1cccs1)C(=O)OC(C)(C)C]

To a solution of tert-butyl N-allyl-N-[2-(methoxy(methyl)amino)-2-oxo-ethyl]carbamate (25 g, 96.8 mmol) in tetrahydrofuran (339 mL) at −78° C. is added drop wise 2-thienyllithium (145 ml, 1 M in tetrahydrofuran) over 20 min. The reaction is carefully quenched with aqueous ammonium chloride (20 mL), diluted with water (100 mL), and extracted with dichloromethane. The organic layers are combined, dried over sodium sulfate, filtered, and concentrated to give a residue. The residue is purified by silica gel flash chromatography, eluting with hexane/ethyl acetate (1:0) to hexane/ethyl acetate (5:1) to give the title compound (15.2 g, 56%). ES/MS (m/e): 182 (M+H-100).

Preparation 22

Benzyl N-(2,2-dimethoxyethyl)carbamate

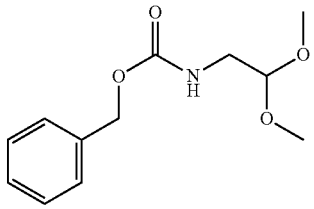 [SMILES: COC(CNC(=O)OCc1ccccc1)OC]

A solution of aminoacetaldehyde dimethyl acetal (25 mL, 229 mmol) in toluene (120 mL) is treated at 0° C. with a 4.85 M sodium hydroxide solution (70.8 mL, 343.5 mmol). The mixture is stirred at 0° C. for 10 minutes and benzyl chloroformate (33.8 mL, 229 mmol) is added keeping the internal temperature below 20° C. during the addition. The mixture is warmed to room temperature over 4 hours. The organic layer is separated, washed with brine, dried over sodium sulfate, and concentrated to dryness to give the title compound (54 g, 98%). ES/MS (m/e): 240 (M+H).

Preparation 23

Benzyl N-allyl-N-(2,2-dimethoxyethyl)carbamate

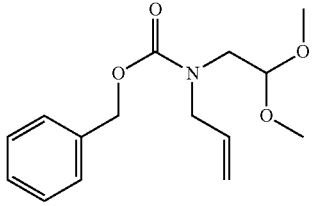 [SMILES: C=CCN(CC(OC)OC)C(=O)OCc1ccccc1]

A solution of benzyl N-(2,2-dimethoxyethyl)carbamate (50 g, 208.9 mmol) in toluene (180 mL) is treated with solid potassium hydroxide (51.6 g, 919.69 mmol) under nitrogen. After 10 minutes, benzyltriethylammonium chloride (0.8 g, 3.1 mmol) is added. After another 10 minutes a solution of allyl bromide (33 g, 272.8 mmol) in toluene (50 mL) is added drop wise over 10 minutes. The resultant mixture is stirred at 50° C. for 48 hours. The mixture is cooled to room temperature and quenched with water. The organic layer is separated, washed with brine, dried over magnesium sulfate, and concentrated to dryness to give the title compound (44 g, 75%). ES/MS (m/e): 280 (M+H).

Preparation 24

Benzyl N-allyl-N-(2-oxoethyl)carbamate

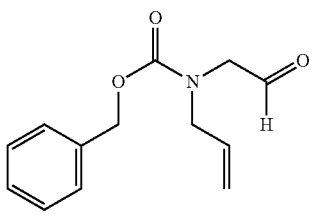 [SMILES: C=CCN(CC=O)C(=O)OCc1ccccc1]

A solution of benzyl N-allyl-N-(2,2-dimethoxyethyl)carbamate (30 g, 107 mmol) in formic acid (36.8 mL, 860 mmol) and water (4.84 mL) is stirred at room temperature overnight. The mixture is concentrated and diluted with hexanes/ethyl acetate (1:2) and water. The organic layer is separated, washed with brine solution until pH=6, and dried over sodium sulfate. The solvent is evaporated to give the title compound (25 g, 99%). ES/MS (m/e): 234 (M+H).

Preparation 25

Benzyl N-allyl-N-[2-hydroxyiminoethyl]carbamate

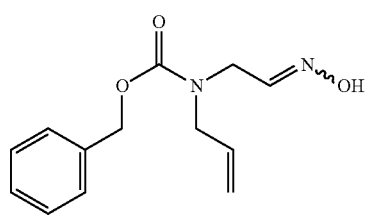 [SMILES: C=CCN(CC=NO)C(=O)OCc1ccccc1]

A solution of benzyl N-allyl-N-(2-oxoethyl)carbamate (25 g, 107 mmol) in acetonitrile (150 mL) is treated with hydroxylamine hydrochloride (9.68 g, 139 mmol) and a solution of sodium acetate trihydrate (16 g, 117.9 mmol) in water (75 mL). The mixture is stirred at room temperature overnight. The acetonitrile is evaporated and the aqueous solution is extracted with ethyl acetate. The organic layer is separated, dried over magnesium sulfate, and concentrated under vacuum to give the title compound (24 g, 90%). ES/MS (m/e): 249 (M+H).

Preparation 26

Benzyl 3,3a,4,6-tetrahydropyrrolo[3,4-c]isoxazole-5-carboxylate

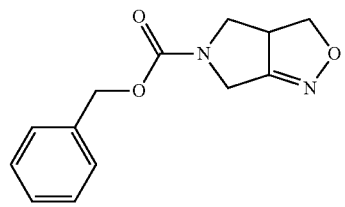 [SMILES: O=C(OCc1ccccc1)N1CC2=NOCC2C1]

A solution of benzyl N-allyl-N-[(2E)-2-hydroxyiminoethyl]carbamate (24 g, 96.6 mmol) in dichloromethane (338 mL) is treated drop wise over 10 minutes with a 5% w/w aqueous solution of sodium hypochlorite (106.08 mmol, 143.06 mL). The resultant mixture is stirred at room temperature overnight. The reaction is quenched with a 40% aqueous solution of sodium bisulfite (7 g). The organic layer is separated, dried over magnesium sulfate, and concentrated under vacuum. The crude product is purified over silica gel eluting with 5% ethyl acetate in hexanes to give the title compound (18 g, 75%). ES/MS (m/e): 247 (M+H).

Preparation 27

5-Allyl-6a-phenyl-3,3a,4,6-tetrahydro-1H-pyrrolo[3,4-c]isoxazole

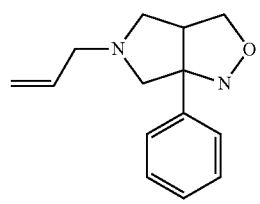

Alpha-bromoacetophenone (77.5 g, 389.36 mmol) is added to a rapidly stirring solution of acetonitrile (1 L) at 0° C. To this solution is added in a drop wise fashion, diallylamine (98.40 mL, 798.18 mmol) over 10 min. The mixture is warmed to room temperature and stirred for 96 h. The solvent is removed under reduced pressure and the residue is dissolved in ethanol (778.71 mL). Pyridine (110.20 mL, 1.36 mmol) is added to the solution followed by hydroxylamine hydrochloride (67.64 g, 973.39 mmol). The reaction is heated to 70° C. for 4 h and then stirred overnight at RT. The solvent is removed under reduced pressure and the residue is dissolved in toluene (1 L). The reaction is heated to 120° C. and stirred overnight. The solvent is removed under reduced pressure. The product is purified via silica gel chromatography eluting with 0-100% ethyl acetate/hexanes to give the title compound as a light red oil (71.2 g, 79.4%) that is used without further purification. El/MS (m/e): 231.0 (M+H).

Preparation 28

5-Allyl-6a-(2-fluorophenyl)-3,3a,4,6-tetrahydro-1H-pyrrolo[3,4-c]isoxazole

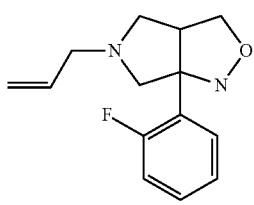 [SMILES: C=CCN1CC2CONC2(c2ccccc2F)C1]

To a solution of 2-bromo-1-(2-fluorophenyl)ethanone (10.0 g, 46.1 mmol) in ethanol (460.8 mL) is added drop wise diallyamine (9.4 g, 96.8 mmol) in ethanol (460.8 mL). The reaction is stirred for 2 hr. Pyridine is then added to the reaction (11.2 mL, 138.2 mmol) followed by the addition of hydroxylamine hydrochloride (4.8 g, 69.1 mmol). The reaction is refluxed for 4 hr and then concentrated to dryness. The residue is dissolved in toluene (230.4 mL) and is refluxed for 8 hr. The mixture is cooled to room temperature and extracted with saturated sodium bicarbonate solution. The aqueous phase is then extracted with DCM. The organic phase is concentrated and the mixture purified by silica gel chromatography eluting with hexane to 1:1 hexane/ethyl acetate to give the title compound (6.6 g, 58%). ES/MS (m/e): 248 (M+H).

Preparation 29

Benzyl 6a-phenyl-3,3a,4,6-tetrahydro-1H-pyrrolo[3,4-c]isoxazole-5-carboxylate

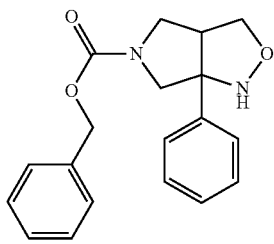 [SMILES: O=C(OCc1ccccc1)N1CC2CONC2(c2ccccc2)C1]

Boron trifluoride (30.8 mL, 244 mmol) is added to a −50° C. solution of benzyl 3,3a,4,6-tetrahydropyrrolo[3,4-c]isoxazole-5-carboxylate (40 g, 162 mmol) in tetrahydrofuran (200 mL). The mixture is stirred for 10 minutes and the solution is added to phenyl magnesium bromide (325 mL, 325 mmol, 1 M in tetrahydrofuran) at −50° C., warmed to 0° C., and stirred for 4 hours. The reaction is quenched with saturated ammonium chloride (200 mL) and the aqueous layer is separated. The organic layer is dried over magnesium sulfate and the solvent is removed under vacuum. The crude product is purified over silica gel using a 5 to 50% ethyl acetate/hexanes gradient to give the title compound (31 g, 59%). ES/MS (m/e): 325 (M+H).

Preparation 30

Benzyl 6a-(2-thienyl)-3,3a,4,6-tetrahydro-1H-pyrrolo[3,4-c]isoxazole-5-carboxylate

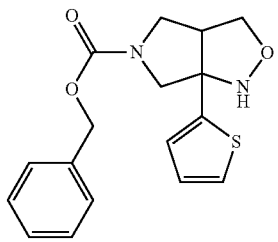 [SMILES: O=C(OCc1ccccc1)N1CC2CONC2(c2cccs2)C1]

A −78° C. solution of thiophene (17 g, 203 mmol) in tetrahydrofuran (250 mL) under nitrogen is treated drop wise with a solution of n-butyl lithium (81 mL, 203 mmol, 1.6 M in hexanes) and the reaction is stirred at −78° C. for 10 minutes. In a separate flask, a −78° C. solution of benzyl 3,3a,4,6-tetrahydropyrrolo[3,4-c]isoxazole-5-carboxylate (25 g, 101 mmol) in tetrahydrofuran (500 mL) under nitrogen is treated with boron trifluoride ether complex (19 mL, 152 mmol) and the mixture is stirred for 10 minutes. The solution is added by cannula to the organolithium solution generated above at −78° C. and the resulting mixture is stirred for 1 hour at −78° C. The reaction is quenched with saturated ammonium chloride and warmed to room temperature. The aqueous layer is separated, the organic layer is dried over magnesium sulfate and the solvent is removed under vacuum. The crude product is purified over silica gel using a 5 to 50% gradient of ethyl acetate/hexanes gradient to give the title compound (22 g, 65%). ES/MS (m/e): 331 (M+H).

The following compound is prepared essentially by the method of Preparation 30 with the appropriate substituted phenyl in place of thiophene.

TABLE 4

| Prep No. | Chemical name | Structure | ES/MS (m/e) |
|---|---|---|---|
| 31 | Benzyl 6a-(3-bromophenyl)-3,3a,4,6-tetrahydro-1H-pyrrolo[3,4-c]isoxazole-5-carboxylate | 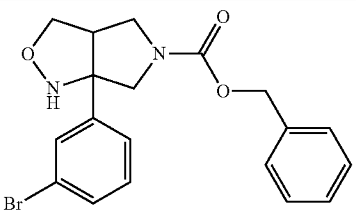 [SMILES: O=C(OCc1ccccc1)N1CC2CONC2(c2cccc(Br)c2)C1] | 403, 405 (M + H) |

Preparation 32

Benzyl 6a-(2-trimethylsilylthiazol-5-yl)-3,3a,4,6-tetrahydro-1H-pyrrolo[3,4-c]isoxazole-5-carboxylate

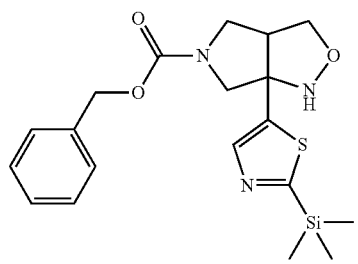 [SMILES: C[Si](C)(C)c1ncc(C23CN(C(=O)OCc4ccccc4)CC2CON3)s1]

A −78° C. solution of 2-trimethylsilylthiazole (383 mg, 2.44 mmol) in tetrahydrofuran (3 mL) is treated drop wise with a solution of n-butyl lithium (1.52 mL, 2.44 mmol, 1.6 M hexanes) and the reaction is stirred at −78° C. for 10 minutes to give a thick orange slurry. The slurry is treated with boron trifluoride etherate (205 µL, 1.62 mmol) to give a red mixture and then a solution of benzyl (3aR)-3,3a,4,6-tetrahydropyrrolo[3,4-c]isoxazole-5-carboxylate (200 mg, 812 µmol) is added immediately in toluene (2 mL) to this mixture. The resultant mixture is stirred at −78° C. for 20 minutes under nitrogen. The reaction is quenched with saturated ammonium chloride and warmed to room temperature. Water and saturated sodium bicarbonate is added and the mixture is extracted with ethyl acetate (3×). The combined organic layers are dried over sodium sulfate and the solvent is removed under vacuum. The crude product is purified over silica gel eluting with 5% to 100% ethyl acetate in hexanes gradient, to give the title compound (245 mg, 75%). ES/MS (m/e): 404 (M+H).

Preparation 33 tert-Butyl N-allyl-N-[-2-hydroxyimino-2-phenyl-ethyl]carbamate

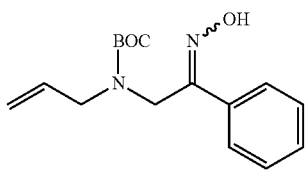 [SMILES: C=CCN(CC(=NO)c1ccccc1)C(=O)OC(C)(C)C]

A mixture of tert-butyl N-allyl-N-phenacyl-carbamate (3.2 g, 11.6 mmol), hydroxylamine hydrochloride (1.2 g, 17.4 mmol) and sodium acetate (1.4 g, 17.4 mmol) in ethanol (46 mL) is stirred at 70° C. for 18 hours. The reaction is cooled, diluted with water and extracted with dichloromethane. The organic layers are combined, dried over sodium sulfate, filtered, and concentrated under reduced pressure to give the title compound as a mixture of E and Z isomers which is used without further purification (3.16 g, 94%). ES/MS (m/e): 191 (M+H-100).

Preparation 34

N-[2-(5-Fluorothiophen-2-yl)-2-(hydroxyimino)ethyl]-N-(prop-2-en-1-yl)prop-2-en-1-amine

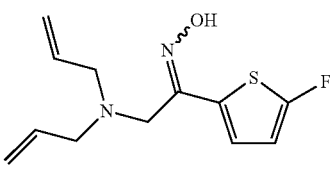 [SMILES: C=CCN(CC=C)CC(=NO)c1ccc(F)s1]

To a stirred solution of 2-(diallylamino)-1-(5-fluoro-2-thienyl)ethanone (4.051 g, 16.93 mmol) in ethanol (34 mL) under nitrogen is added pyridine (4.8 mL, 59.2 mmol) and hydroxylamine hydrochloride (2.94 g, 42.3 mmol). The mixture is heated to 70° C. for 4 hours. The mixture is allowed to cool and then concentrated under reduced pressure. The residue is diluted with ethyl acetate (100 mL) and water (50 mL). The phases are separated and the aqueous phase extracted with ethyl acetate (50 mL). The combined organic extracts are dried over sodium sulfate, filtered, and concentrated to give the title compound (4.25 g, 99%) (approximately a 1.4:1 mixture of oxime isomers by $^1$H-NMR (CDCl$_3$). ES/MS (m/e): 255 (M+H).

The following compound is prepared as essentially by the method of Preparation 34 using 2-bromo-1-thiazol-5-yl-ethanone as the starting material.

TABLE 5

| Prep No. | Chemical name | Structure | ES/MS (m/e) |
|---|---|---|---|
| 35 | 2-(Diallylamino)-1-thiazol-5-yl-ethanone oxime | 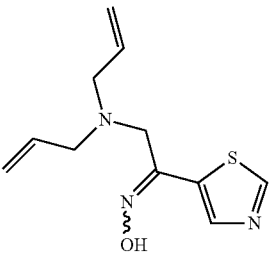 [SMILES: C=CCN(CC=C)CC(=NO)c1cncs1] | 238 (M + H) |

Preparation 36 tert-Butyl N-allyl-N-[2-hydroxyimino-2-isothiazol-5-yl-ethyl]carbamate

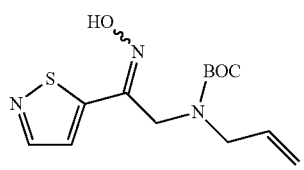 [SMILES: C=CCN(CC(=NO)c1ccns1)C(=O)OC(C)(C)C]

To a room temperature solution of tert-butyl N-allyl-N-(2-isothiazol-5-yl-2-oxo-ethyl)carbamate (5.93 g, 21.00 mmol) in ethanol (70 mL) is added pyridine (5.94 mL, 73.50 mmol) and hydroxylamine hydrochloride (3.65 g, 52.50 mmol). The mixture is heated to reflux for 4 hours. The mixture is allowed to cool to room temperature and is then concentrated under reduced pressure. The resulting crude product is diluted with ethyl acetate (200 mL) and washed with saturated sodium bicarbonate (150 mL). The aqueous layer is re-extracted with ethyl acetate (2×100 mL). The combined organic layers are dried over sodium sulfate, filtered, and the solvent is removed under vacuum. The crude product is purified by silica gel column chromatography using a 15 minute, 0% to 20% ethyl acetate in dichloromethane gradient, to give the title compound as a mixture of E and Z isomers (5.62 g, 18.90 mmol, 90%). ES/MS (m/e): 298 (M+H).

Preparation 37 tert-Butyl N-allyl-N-[2-hydroxyimino-2-(2-thienyl) ethyl]carbamate

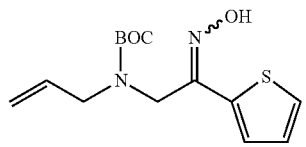 [SMILES: C=CCN(CC(=NO)c1cccs1)C(=O)OC(C)(C)C]

A mixture of tert-butyl N-allyl-N-[2-oxo-2-(2-thienyl) ethyl]carbamate (15.2 g, 54.0 mmol), hydroxylamine hydrochloride (5.63 g, 81.0 mmol) and sodium acetate (6.65 g 81.0 mmol) in ethanol (216 mL) is stirred at 70° C. for 18 hours. The reaction is cooled and the solvent removed under reduced pressure. The residue is diluted water (100 mL) and extracted with dichloromethane. The organic layers are combined dried over sodium sulfate, filtered and concentrated under reduced pressure to give the crude title compound as a mixture of E and Z isomers, which is used without further purification (16 g, >98%): ES/MS (m/e): 197 (M+H-100).

The following compound is prepared as essentially by the method of Preparation 37 using 1-(4-bromo-2-thienyl)-2-(diallylamino)ethanone as the starting material.

TABLE 6

| Prep No. | Chemical name | Structure | Physical data |
|---|---|---|---|
| 38 | 1-(4-Bromo-2-thienyl)-2-(diallyl-amino)etha-none oxime | 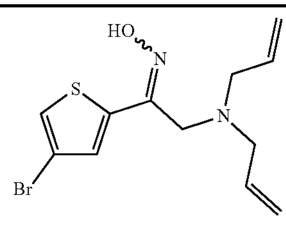 | $^1$H NMR (CDCl$_3$) δ 3.15-3.25 (m, 4H), 3.60, 3.75 (s, 2H), 5.19-5.23 (m, 4H), 5.82-5.95 (m, 2H), 7.12, 7.15 (d, 1H), 7.40, 7.70 (d, 1H) |

Preparation 39

6a-Phenyl-1,3,3a,4,5,6-hexahydropyrrolo[3,4-c]isoxazole

5-Allyl-6a-phenyl-3,3a,4,6-tetrahydro-1H-pyrrolo[3,4-c]isoxazole (3.89 g, 16.89 mmol) is dissolved in chloroform (168 mL) and the solution is degassed with dry nitrogen for 10 minutes. N,N-Dimethylbarbituric acid (13.19 g, 84.45 mmol) is added to the solution and the solution is degassed with nitrogen for another 5 min Tetrakis(triphenylphosphine) palladium (1.95 g, 1.69 mmol) is added and the reaction is stirred for 18 hours. 1 N Hydrochloric acid (50 mL) is added and the mixture is stirred for 20 minutes. The solution is extracted with aqueous hydrochloric acid (3×75 mL) and the combined HCl solution is washed with dichloromethane. The pH is adjusted to approximately 13 with 5 N sodium hydroxide solution. The mixture is extracted with dichloromethane (3×75 mL), dried over sodium sulfate, filtered, and concentrated to give the title compound (3.21 g, 92%). EI/MS (m/e): 191.3 (M+H).

The following compounds are prepared essentially as described in preparation 39.

TABLE 7

| Prep No. | Chemical name | Structure | ES/MS (m/e) |
|---|---|---|---|
| 40 | 6a-(2-Fluorophenyl)-1,3,3a,4,5,6-hexahydropyrrolo[3,4-c]isoxazole | 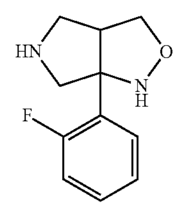 | 309 (M + H). |
| 41 | 6a-(4-Bromo-2-thienyl)-1,3,3a,4,5,6-hexahydropyrrolo[3,4-c]isoxazole | 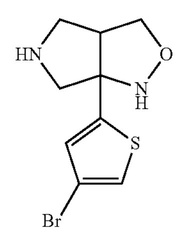 | ($^{79}$Br/$^{81}$Br) 275/277 (M + H) |

Preparation 42 tert-Butyl-6a-phenyl-3,3a,4,6-tetrahydro-1H-pyrrolo[3,4-c]isoxazole-5-carboxylate

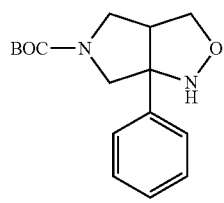

A solution of tert-butyl N-allyl-N-[-2-hydroxyimino-2-phenyl-ethyl]carbamate as a mixture of E and Z isomers (3.2 g, 10.9 mmol) in xylene (100 mL) is stirred at 100° C. for 2 hours, 130° C. for 6 hours, 100° C. for 12 hours and 130° C. for 2 hours. The cooled reaction is concentrated under reduced pressure to give a residue. The residue is purified by silica gel flash chromatography, eluting with hexane/ethyl acetate (1:0) to hexane/ethyl acetate (0:1) to give the title compound (1.5 g, 48%). ES/MS (m/e): 291 (M+H).

Preparation 42, Alternate Procedure tert-Butyl-6a-phenyl-3,3a,4,6-tetrahydro-1H-pyrrolo[3,4-c]isoxazole-5-carboxylate

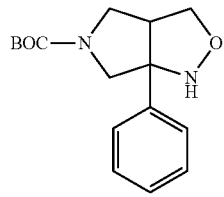

Dichloromethane (5.26 mL) is added to 6a-phenyl-1,3,3a,4,5,6-hexahydropyrrolo[3,4-c]isoxazole (100 mg, 525.64 mmol). Di-t-butyldicarbonate (108.98 mg, 499.36 mmol) is added to the mixture followed by triethylamine (0.146 mL, 1.05 mmol) and the mixture is stirred for 2 hr. The solvent is removed under reduced pressure. The product is purified via silica gel chromatography eluting with 0-100% ethyl acetate/hexanes to give the title compound as a clear oil (143 mg, 94%). EI/MS (m/e): 291.0 (M+H).

The following compound is prepared essentially as described by preparation 42, alternate procedure.

TABLE 8

| Prep No. | Chemical name | Structure | ES/MS (m/e) |
|---|---|---|---|
| 43 | tert-Butyl 6a-(2-fluorophenyl)-3,3a,4,6-tetrahydro-1H-pyrrolo[3,4-c]isoxazole-5-carboxylate | 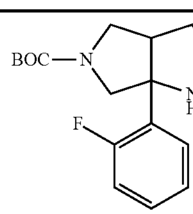 | 309 (M + H) |
| 44 | tert-Butyl 6a-(4-bromo-2-thienyl)-3,3a,4,6-tetrahydro-1H-pyrrolo[3,4-c]isoxazole-5-carboxylate | | ($^{79}$Br/$^{81}$Br) 372/374 (M + H) |

Preparation 45 tert-Butyl 6a-(2-thienyl)-3,3a,4,6-tetrahydro-1H-pyrrolo[3,4-c]isoxazole-5-carboxylate

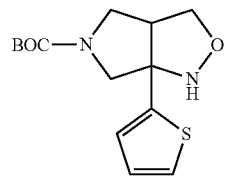

A solution of tert-butyl N-allyl-N-[(2-hydroxyimino-2-(2-thienyl)ethyl]carbamate as a mixture of E and Z isomers (16 g, 54.0 mmol) in xylene (500 mL) is stirred at 130° C. for 10 hours. The reaction is cooled and concentrated under reduced pressure to give a residue. The residue is purified by silica gel flash chromatography, eluting with hexane/ethyl acetate (1:0) to hexane/ethyl acetate (0:1) to give the title compound (7.26 g, 45%). ES/MS (m/e): 297.2 (M+H).

The following compound is prepared essentially by the method described for preparation 45 using the appropriate oxime.

| Prep No. | Chemical name | Structure | ES/MS (m/e) |
|---|---|---|---|
| 46 | tert-Butyl 6a-isothiazol-5-yl-3,3a,4,6-tetrahydro-1H-pyrrolo[3,4-c]isoxazole-5-carboxylate | 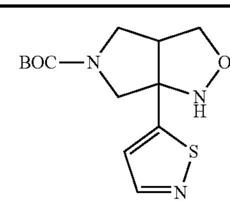 | 298 |

Preparation 47

5-Allyl-6a-(5-fluoro-2-thienyl)-3,3a,4,6-tetrahydro-1H-pyrrolo[3,4-c]isoxazole

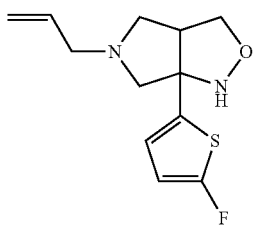 [SMILES: C=CCN1CC2CONC2(c2ccc(F)s2)C1]

To N-[2-(5-fluorothiophen-2-yl)-2-(hydroxyimino)ethyl]-N-(prop-2-en-1-amine (4.23 g, 16.6 mmol) under nitrogen is added toluene (208 mL) and the solution is heated to reflux for 22.5 hours. The solution is allowed to cool and concentrated under reduced pressure to a residue. The residue is purified by HPLC (silica gel) eluting with hexanes/ethyl acetate (one-step gradient from 80:20 to 70:30) to give the title compound (1.949 g, 46%). ES/MS (m/e): 255 (M+H).

The following compounds are prepared essentially by the method described for preparation 47 using the appropriate oxime.

TABLE 9

| Prep. No. | Chemical name | Structure | ES/MS (m/e) (M + H) |
|---|---|---|---|
| 48 | 5-Allyl-6a-(4-fluorophenyl)-3,3a,4,6-tetrahydro-1H-pyrrolo[3,4-c]isoxazole | 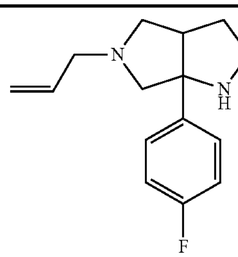 | 249 |
| 49 | 5-Allyl-6a-(4-bromo-2-thienyl)-3,3a,4,6-tetrahydro-1H-pyrrolo[3,4-c]isoxazole | 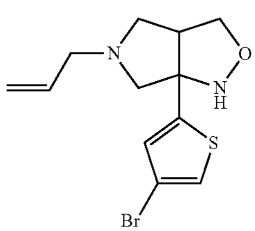 [SMILES: C=CCN1CC2CONC2(c2cc(Br)cs2)C1] | (⁷⁹Br/⁸¹Br) 315/317 |

TABLE 9-continued

| Prep. No. | Chemical name | Structure | ES/MS (m/e) (M + H) |
|---|---|---|---|
| 50 | 5-Allyl-6a-thiazol-5-yl-3,3a,4,6-tetrahydro-1H-pyrrolo[3,4-c]isoxazole | 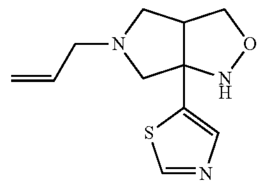 [SMILES: C=CCN1CC2CONC2(c2cncs2)C1] | 238 |

Preparation 51

Benzyl 1-(benzoylcarbamothioyl)-6a-(2-trimethylsilylthiazol-5-yl)-3,3a,4,6-tetrahydropyrrolo[3,4-c]isoxazole-5-carboxylate

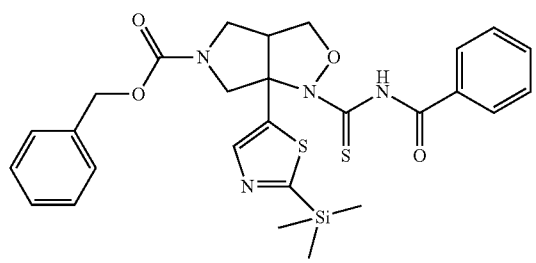 [SMILES: C[Si](C)(C)c1ncc(C23CN(C(=O)OCc4ccccc4)CC2CON3C(=S)NC(=O)c2ccccc2)s1]

To a mixture of benzyl (3aS)-6a-(2-trimethylsilylthiazol-5-yl)-3,3a,4,6-tetrahydro-1H-pyrrolo[3,4-c]isoxazole-5-carboxylate (0.218 g, 0.54 mmol) in THF (3.60 mL) is added benzoyl isothiocyanate (0.088 g, 0.54 mmol). The mixture is stirred for 1 hour at room temperature and more benzoyl isothiocyanate (0.044 g, 0.27 mmol) is added. The reaction is stirred for 3 hours at room temperature, concentrated under reduced pressure, and purified by silica gel chromatography eluting with a gradient of 5% to 100% ethyl acetate in hexanes to give title compound (0.204 g, 67%). ES/MS (m/e): 404 (M+H).

The following compound is prepared essentially by the method of Preparation 51 using the appropriate benzyl carboxylate.

TABLE 10

| Prep No. | Chemical name | Structure | ES/MS (m/e) |
|---|---|---|---|
| 52 | Benzyl 1-(benzoylcarbamothioyl)-6a-(3-bromophenyl)-3,3a,4,6-tetrahydropyrrolo[3,4-c]isoxazole-5-carboxylate | 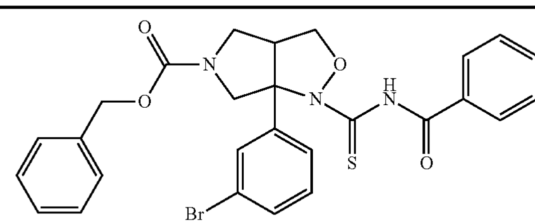 | 494 (M + H) |

Preparation 53 tert-Butyl 3-amino-4-(hydroxymethyl)-3-phenyl-pyrrolidine-1-carboxylate

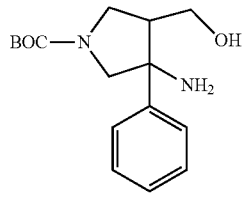 [SMILES: CC(C)(C)OC(=O)N1CC(CO)C(N)(c2ccccc2)C1]

tert-Butyl 6a-phenyl-3,3a,4,6-tetrahydro-1H-pyrrolo[3,4-c]isoxazole-5-carboxylate (142 mg, 489.04 mmol) is dissolved in methanol (10 mL). The solution is put through a flow hydrogenator with the Raney/Ni catalyst bed at 1 atmosphere $H_2$ pressure and at 20° C., with a flow rate of 1 mL/min. Wash the bed with 10 mL more of MeOH after all the original solution has passed through. Remove the solvent under reduced pressure to obtain the title compound as a clear oil (168 mg, 117%) EI/MS (m/e): 293.3 (M+H).

Preparation 54

Benzyl 3-amino-4-(hydroxymethyl)-3-phenyl-pyrrolidine-1-carboxylate

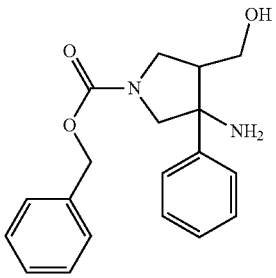 [SMILES: NC1(c2ccccc2)CN(C(=O)OCc2ccccc2)CC1CO]

Powdered zinc (43.7 g, 669 mmol) is added to a solution of benzyl 6a-phenyl-3,3a,4,6-tetrahydro-1H-pyrrolo[3,4-c]isoxazole-5-carboxylate (31 g, 96 mmol) in acetic acid (310 mL) and the mixture is stirred for 30 minutes. Ethyl acetate (500 mL) is added and the mixture is filtered through diatomaceous earth. The solvent is removed under vacuum and the crude product is re-dissolved in ethyl acetate. Water is added to the solution and the pH is adjusted to 10 with 2 M NaOH. The solution is filtered through diatomaceous earth, the layers are separated, and the organic layer is dried over magnesium sulfate, and concentrated to give the title compound (31 g, 99%). ES/MS (m/e): 327 (M+H).

Preparation 55 tert-Butyl 3-amino-3-(2-fluorophenyl)-4-(hydroxymethyl)pyrrolidine-1-carboxylate

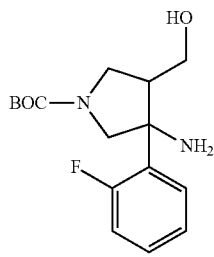 [SMILES: CC(C)(C)OC(=O)N1CC(CO)C(N)(c2ccccc2F)C1]

A mixture of tert-butyl 6a-(2-fluorophenyl)-3,3a,4,6-tetrahydro-1H-pyrrolo[3,4-c]isoxazole-5-carboxylate (5 g, 16.2 mmol) and zinc dust (10.6 g 0.16 mol) is treated with acetic acid (65 mL) in one portion under nitrogen at room temperature. The resulting mixture is stirred for 0.5 hour, diluted with ethyl acetate, and filtered through diatomaceous earth. The filtrate is added drop-wise to a mixture of saturated sodium bicarbonate in water containing an excess of solid sodium bicarbonate (84 g, 1 mol). The mixture is extracted with ethyl acetate, the organic phase is dried over magnesium sulfate, and the solvent removed under vacuum. The residue is purified by silica gel chromatography eluting with ethyl acetate to give the title compound (4.4 g, 87%). ES/MS (m/e): 311(M+H).

The following compound is prepared essentially by the method of Preparation 55

TABLE 11

| Prep No. | Chemical name | Structure | ES/MS (m/e) |
|---|---|---|---|
| 56 | tert-Butyl 3-amino-3-(4-bromo-2-thienyl)-4-(hydroxymethyl)pyrrolidine-1-carboxylate | 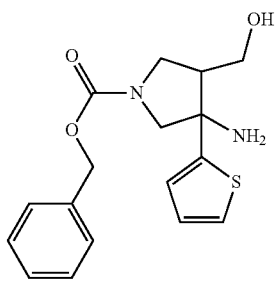 [SMILES: NC1(c2cccs2)CN(C(=O)OCc2ccccc2)CC1CO] | ($^{79}$Br/$^{81}$Br) 302/304 (M + H) |

Preparation 57

Benzyl 3-amino-4-(hydroxymethyl)-3-(2-thienyl)pyrrolidine-1-carboxylate

Zinc (398.33 g, 6.092 mol) is added in portions over about 30 minutes to a vigorously stirred solution of acetic acid (2.56 L) and temperature is maintained at 30° C. or below. A solution of benzyl 6a-(2-thienyl)-3,3a,4,6-tetrahydro-1H-pyrrolo[3,4-c]isoxazole-5-carboxylate (366 g, 1.107 mol) in acetic acid (915 mL) is slowly added to the reaction mixture keeping internal temperature at 45° C. The mixture is stirred at 45° C. for 1 hour. The reaction is cooled to room temperature, diluted with MTBE (3.63 L) and filtered through diatomaceous earth. The filtrate is evaporated and the residue dried under vacuum to constant weight. Toluene (4×742 mL) is added to the residue and the mixture is concentrated again to remove as much acetic acid at possible to give an orange oily residue (476.8 g). The residue is diluted with water, (2.928 L), MTBE (2.928 L)

followed by HCl (5 M, 664.63 mL) and stirred for 10 minutes. The mixture is transferred to a separator and the aqueous layer is separated. The organic layer is re-extracted with HCl (1 M, 3×742.36 mL). The aqueous phases are combined, cooled in ice water with stirring, and the pH is adjusted to 10 with aqueous NaOH solution. MTBE (2.969 L) is added and mixture stirred. A white solid precipitates and is removed by filtration diatomaceous earth. The mixture is transferred to a separator and the organic layer is separated. The aqueous layer is washed with MTBE (2×500 mL) and the organics are combined, dried over sodium sulfate, and filtered. The filtrates are concentrated under vacuum to obtain the title compound as light brown oil (240 g, 65%). ES/MS (m/e): 333 (M+H).

Alternate Preparation 57

A solution of benzyl 6a-(2-thienyl)-3,3a,4,6-tetrahydro-1H-pyrrolo[3,4-c]isoxazole-5-carboxylate (22 g, 66.6 mmol) in acetic acid (220 mL) under nitrogen is treated with zinc dust (34.8 g 0.53 mol) at room temperature. The resulting mixture is stirred for 2 hours and then diluted with ethyl acetate and filtered through diatomaceous earth. The solvent is evaporated and the residue is dissolved in ethyl acetate and water, and the pH is adjusted to 10 with 2 M sodium hydroxide solution. The organic layer is separated, dried over magnesium sulfate and the solvent removed under vacuum to give the title compound (21 g, 94%). ES/MS (m/e): 333 (M+H).

The following compounds are prepared essentially by the Alternate method of Preparation 57.

TABLE 12

| Prep No. | Chemical name | Structure | ES/MS (m/e) |
|---|---|---|---|
| 58 | Benzyl 3-(benzoylcarbamothioyl-amino)-4-(hydroxymethyl)-3-(2-trimethylsilylthiazol-5-yl)pyrrolidine-1-carboxylate[a] | 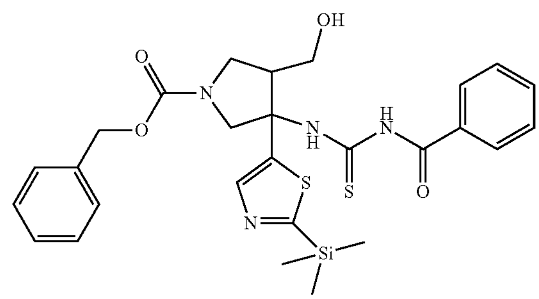 [SMILES: C[Si](C)(C)c1ncc(C2(NC(=S)NC(=O)c3ccccc3)CN(C(=O)OCc3ccccc3)CC2CO)s1] | 569 (M + H) |
| 59 | [1-Allyl-4-amino-4-(4-bromo-2-thienyl)pyrrolidin-3-yl]methanol[b] | 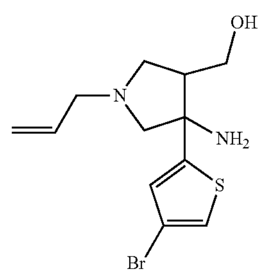 [SMILES: C=CCN1CC(CO)C(N)(c2cc(Br)cs2)C1] | ($^{79}$Br/$^{81}$Br) 317/319 (M + H) |
| 60 | [1-Allyl-4-amino-4-(4-fluorophenyl)pyrrolidin-3-yl]methanol[c] | 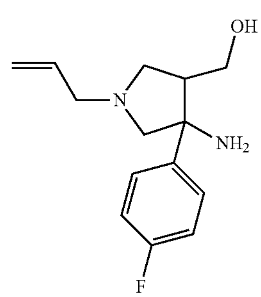 [SMILES: C=CCN1CC(CO)C(N)(c2ccc(F)cc2)C1] | 251 (M + H) |

[a]Reaction is heated for 1 hr at 50° C.
[b]Reaction is heated at 40° C. for 4 hr.
[c]Reaction is heated at 50° C. for 20 hr.

Preparation 61

Benzyl 3-(benzoylcarbamothioylamino)-4-(hydroxymethyl)-3-(2-thienyl)pyrrolidine-1-carboxylate

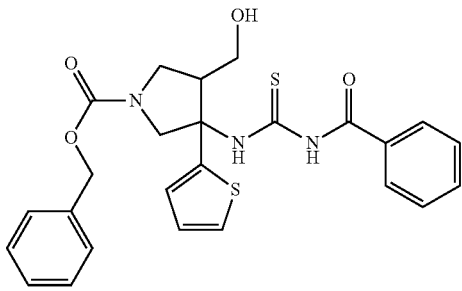 [SMILES: O=C(NC(=S)NC1(c2cccs2)CN(C(=O)OCc2ccccc2)CC1CO)c1ccccc1]

A solution of benzyl 3-amino-4-(hydroxymethyl)-3-(2-thienyl)pyrrolidine-1-carboxylate (21 g, 63 mmol) in tetrahydrofuran (210 mL) at 0° C. is treated with benzoyl isothiocyanate (8.95 mL, 66.3 mmol. The resulting solution is stirred for 2 hours at 0° C. and quenched by adding an aqueous solution of sodium chloride and methyl-t-butyl ether. The organic layer is separated, dried over magnesium sulfate, and the solvent evaporated to give the title compound (30 g, 95%). ES/MS (m/e): 496 (M+H).

Preparation 62 tert-Butyl 3-(benzoylcarbamothioylamino)-3-(2-fluorophenyl)-4-(hydroxymethyl)pyrrolidine-1-carboxylate

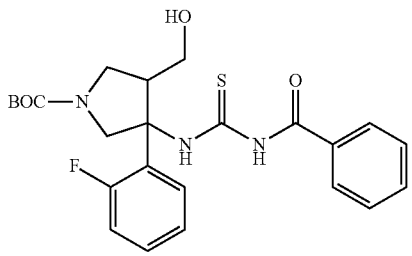 [SMILES: CC(C)(C)OC(=O)N1CC(CO)C(NC(=S)NC(=O)c2ccccc2)(c2ccccc2F)C1]

To three separate reaction vessels, each containing racemic tert-butyl 3-amino-3-(2-fluorophenyl)-4-(hydroxymethyl) pyrrolidine-1-carboxylate (0.142 g, 4.58 mmol) and tetrahydrofuran (18 mL), is added benzoyl isothiocyanate (0.784 g, 4.80 mmol). The solutions are stirred at 22° C., and stirred for 15 hours. The solvent is removed under a stream of nitrogen, the residues combined, and concentrated to provide the crude title compound, which is used without further purification. ES/MS (m/e): 474 (M+H).

Preparation 63 tert-Butyl 3-(benzoylcarbamothioylamino)-3-(4-bromo-2-thienyl)-4-(hydroxymethyl)pyrrolidine-1-carboxylate

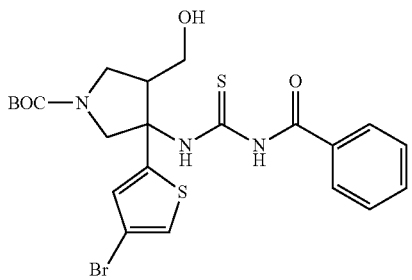 [SMILES: CC(C)(C)OC(=O)N1CC(CO)C(NC(=S)NC(=O)c2ccccc2)(c2cc(Br)cs2)C1]

To a solution of tert-butyl 3-amino-3-(4-bromo-2-thienyl)-4-(hydroxymethyl)pyrrolidine-1-carboxylate (8.5 g, 22.5 mmol) in tetrahydrofuran (100 mL) at 0° C. is added benzoyl isothiocyanate (3.24 mL, 24 mmol). The resulting solution is warmed to room temperature, and stirred under nitrogen at room temperature for 2 hours. The solution is concentrated and the residue is purified by silica gel flash chromatography eluting with hexanes/ethyl acetate (gradient from 100:0 to 0:100 over 30 min) to give the title compound. ES/MS (m/e): ($^{79}$Br/$^{81}$Br) 538/540 (M+H).

Preparation 64

Benzyl 3-(benzoylcarbamothioylamino)-4-(hydroxymethyl)-3-phenyl-pyrrolidine-1-carboxylate

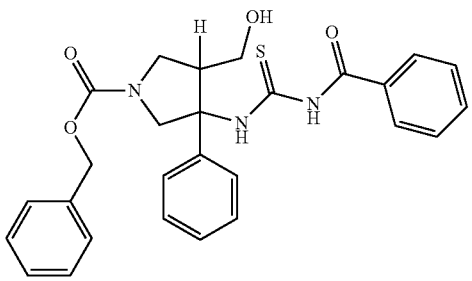 [SMILES: O=C(NC(=S)NC1(c2ccccc2)CN(C(=O)OCc2ccccc2)CC1CO)c1ccccc1]

Benzoyl isothiocyanate (15 mL, 112 mmol) is added to a 0° C. solution of benzyl 3-amino-4-(hydroxymethyl)-3-phenyl-pyrrolidine-1-carboxylate (34.7 g, 106 mmol) in tetrahydrofuran (347 mL). The mixture is warmed to room temperature and stirred for 1 hour. Brine (300 mL) is added, the aqueous layer is separated, the organic layer is dried over magnesium sulfate, and concentrated to give the title compound (51 g, 98%). ES/MS (m/e): 390 (M+H).

Preparation 65

N-[[1-Allyl-3-(4-bromo-2-thienyl)-4-(hydroxymethyl)pyrrolidin-3-yl]carbamoyl]benzamide

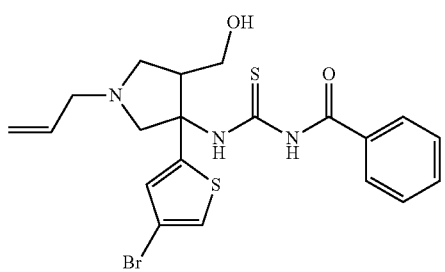 [SMILES: C=CCN1CC(CO)C(NC(=S)NC(=O)c2ccccc2)(c2cc(Br)cs2)C1]

To a solution of [1-allyl-4-amino-4-(4-bromo-2-thienyl) pyrrolidin-3-yl]methanol 4 g, 12.6 mmol) in tetrahydrofuran (180 mL) is added bis(trimethylsilyl) trifluoroacetamide (3.2 g, 12.6 mmol) and the reaction is stirred at room temperature for 1 hr. Benzoyl isothiocyanate (2.5 g, 15.1 mmol) is added in one portion, stirred for 1 hour at room temperature, and then quenched with 1 N hydrochloric acid (20 mL). After stirring for 1 hour the pH of the reaction is adjusted to >8 using saturated sodium bicarbonate and extracted with dichloromethane. The organic phases are combined, concentrated under reduced pressure, and triturated with hexane/ethyl acetate (4:1) to give the title compound (5.9 g, >95%). ES/MS (m/e) ($^{79}$Br/$^{81}$Br) 480/482 (M+H).

Preparation 66

N-[5-Allyl-6a-(5-fluoro-2-thienyl)-3,3a,4,6-tetrahydropyrrolo[3,4-c]isoxazole-1-carbothioyl]benzamide

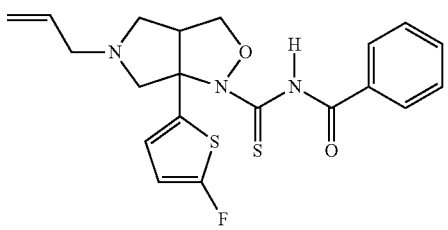 [SMILES: C=CCN1CC2CON(C(=S)NC(=O)c3ccccc3)C2(c2ccc(F)s2)C1]

To a stirred solution of 5-allyl-6a-(5-fluoro-2-thienyl)-3,3a,4,6-tetrahydro-1H-pyrrolo[3,4-c]isoxazole (4.22 g, 16.59 mmol) in tetrahydrofuran (83 mL) is added benzoyl isothiocyanate (2.7 mL, 19.9 mmol). The resulting solution is stirred under nitrogen at room temperature for 19 hours. The solution is concentrated and the residue is purified by silica gel flash chromatography eluting with hexanes/ethyl acetate (two-step gradient from 80:20 to 70:30 to 60:40) to give the title compound (6.92 g, 100%). ES/MS (m/e): 418 (M+H).

The following compound is prepared essentially by the method of Preparation 66 using the appropriate isoxazole.

TABLE 13

| Prep. No. | Chemical name | Structure | ES/MS (m/e) |
|---|---|---|---|
| 67 | N-(5-Allyl-6a-thiazol-5-yl-3,3a,4,6-tetrahydropyrrolo[3,4-c]isoxazole-1-carbothioyl)benzamide | 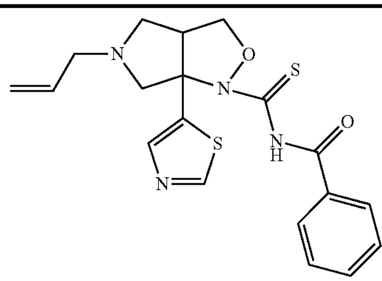 | 401 (M + H) |

Preparation 68

N-[[1-Allyl-3-(4-fluorophenyl)-4-hydroxymethyl)pyrrolidin-3-yl]carbamothioyl]benzamide

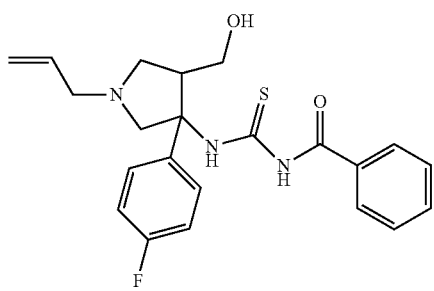 [SMILES: C=CCN1CC(CO)C(NC(=S)NC(=O)c2ccccc2)(c2ccc(F)cc2)C1]

To a solution of [1-allyl-4-amino-4-(4-fluorophenyl)pyrrolidin-3-yl]methanol (4.03 g, 16.11 mmol) in tetrahydrofuran (107.4 mL) is added benzoyl isothiocyanate (2.63 g, 16.11 mmol) and the reaction is stirred under nitrogen for 2 hours and then at −20° C. for 2.5 days. The reaction is concentrated and purified by silica gel chromatography eluting with a 0-100% gradient of ethyl acetate in hexanes to give the title compound (2 g, 30%). EI/MS: 414 (M+H).

Preparation 69

N-[[1-Allyl-3-(5-fluoro-2-thienyl)-4-(hydroxymethyl)pyrrolidin-3-yl]carbamothioyl]benzamide

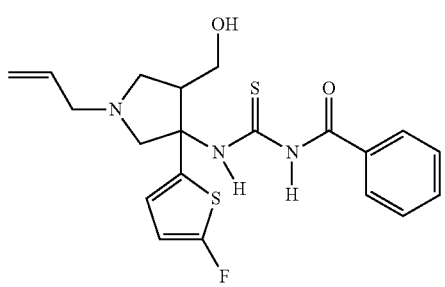 [SMILES: C=CCN1CC(CO)C(NC(=S)NC(=O)c2ccccc2)(c2ccc(F)s2)C1]

To N-[5-allyl-6a-(5-fluoro-2-thienyl)-3,3a,4,6-tetrahydropyrrolo[3,4-c]isoxazole-1-carbothioyl]benzamide (6.91 g, 16.5 mmol) is added acetic acid (110 mL) followed by powdered zinc (10.8 g). The resulting gray mixture is rapidly stirred at room temperature for 40 minutes. The mixture is filtered through diatomaceous earth while rinsing with methanol (approximately 250 mL). The filtrate is concentrated under reduced pressure, diluted with methanol (200 mL), and concentrated under reduced pressure. The residue is dissolved in dichloromethane (300 mL) and treated with 1 M potassium carbonate solution (200 mL). The resulting emulsion is filtered through diatomaceous earth while rinsing with water (approximately 40 mL) and dichloromethane (200 mL). The phases are separated and the aqueous phase is further extracted with dichloromethane (100 mL). The combined dichloromethane extracts are dried over sodium sulfate, filtered, and concentrated under reduced pressure to give the title compound (6.65 g, 96%). ES/MS (m/e): 420 (M+H).

The following compound is prepared essentially by the method of Preparation 69 using the appropriate benzamide.

TABLE 14

| Prep. No. | Chemical name | Structure | ES/MS (m/e) |
|---|---|---|---|
| 70 | N-[[1-Allyl-4-(hydroxymethyl)-3-thiazol-5-yl-pyrrolidin-3-yl]carbamothioyl]benzamide | 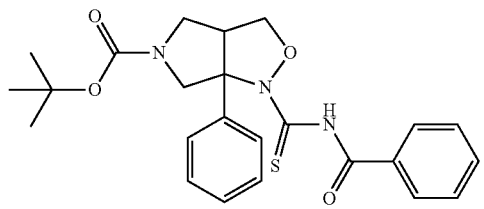 | 403 (M + H) |

Preparation 71 tert-Butyl-1-(benzoylcarbamothioyl)-6a-phenyl-3,3a,4,6-tetrahydropyrrolo[3,4-c]isoxazole-5-carboxylate To a mixture of tert-butyl-6a-phenyl-3,3a,4,6-tetrahydro-1H-pyrrolo[3,4-c]isoxazole-5-carboxylate (1.5 g, 5.2 mmol) in tetrahydrofuran (34 mL) is added benzoyl isothiocyanate (0.84 g, 5.17 mmol). The reaction is stirred for 1 hour at room temperature, concentrated under reduced pressure, and triturated with hexane/ethyl acetate (1:1) to give title compound (1.84 g). The collected solute is purified by silica gel flash chromatography, eluting with hexane/ethyl acetate (1:0) to hexane/ethyl acetate (0:1) to give the title compound, which is combined with the triturated material (2.12 g, 90%). ES/MS (m/e): 454 (M+H).

Preparation 72 tert-Butyl 1-(benzoylcarbamothioyl)-6a-(2-thienyl)-3,3a,4,6-tetrahydropyrrolo[3,4-c]isoxazole-5-carboxylate

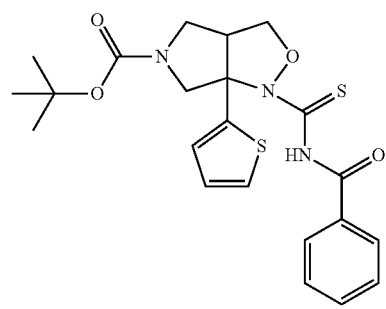 [SMILES: CC(C)(C)OC(=O)N1CC2CON(C(=S)NC(=O)c3ccccc3)C2(c2cccs2)C1]

To a mixture of tert-butyl 6a-(2-thienyl)-3,3a,4,6-tetrahydro-1H-pyrrolo[3,4-c]isoxazole-5-carboxylate (7.16 g, 24.2 mmol) in THF (161 mL) is added benzoyl isothiocyanate (3.94 g, 24.2 mmol). The reaction is stirred for 1 hour at room temperature, concentrated under reduced pressure, and triturated with hexane/ethyl acetate (1:1) to give the title compound. ES/MS (m/e): 459 (M+H).

The following compound is prepared essentially by the method of Preparation 72 and the reaction is stirred for 3 days at room temperature.

TABLE 15

| Prep. No. | Chemical name | Structure | ES/MS (m/e) |
|---|---|---|---|
| 73 | tert-Butyl (3aR,6aR)-1-(benzoylcarbamothioyl)-6a-isothiazol-5-yl-3,3a,4,6-tetrahydropyrrolo[3,4-c]isoxazole-5-carboxylate | BOC-[structure] | 459 (M − 1) |

Preparation 73a tert-Butyl 6a-isothiazol-5-yl-1-[(4-methoxyphenyl)methyl]-3,3a,4,6-tetrahydropyrrolo[3,4-c]isoxazole-5-carboxylate

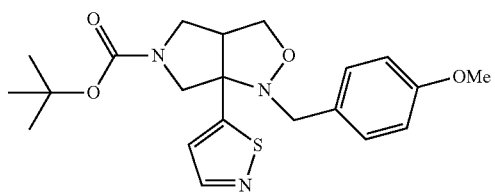 [SMILES: COc1ccc(CN2OCC3CN(C(=O)OC(C)(C)C)CC32c2ccns2)cc1]

tert-Butyl N-allyl-N-(2-isothiazol-5-yl-2-oxo-ethyl)carbamate (610.1 g, 2.16 mol) is dissolved in toluene (6.10 L) under an atmosphere of nitrogen. N-[(4-methoxyphenyl)methyl]hydroxylamine (532.68 g, 2.81 mol) is added followed by diisopropylethylamine (489.86 mL, 2.81 mol). Ti(OEt)$_4$ (640.78 g, 2.81 mol) is added and the yellow reaction solution is heated to 100° C. with stirring for 2 hours. The reaction is cooled to room temperature and diluted with ethyl acetate (3.05 L). A solution of citric acid 50% w/w in water (5.49 L) is added. A solid precipitates which then re-dissolves on stirring. The biphasic mixture is separated and the aqueous layer is extracted with ethyl acetate (2×1 L). The combined organic layers are washed with water (2×2 L), brine, dried over Na$_2$SO$_4$, filtered, and concentrated to dryness. The residue is dissolved in ethyl acetate (3 L) and concentrated under reduced pressure again. The crude product is triturated in ethyl acetate (1.2 L) and isohexane (4.8 L) for 40 minutes. The suspension is filtered and washed with hexane (4 L). The solid is dried under vacuum for 3 hours and in a vacuum oven at 40° C. for 16 hours to give the title product (741.51 g, 82.2%). ES/MS (m/e): 418 (M+H). The mother liquor from the trituration is concentrated under reduced pressure to give a brown solid, which is re-crystallized from methanol (150 mL) to obtain a second crop of product as a off-white solid, (26.02 g, 62.32 mmol, 2.9% yield).

Preparation 73b tert-Butyl 6a-isothiazol-5-yl-3,3a,4,6-tetrahydro-1H-pyrrolo[3,4-c]isoxazole-5-carboxylate

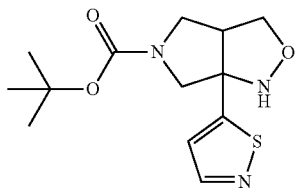 [SMILES: CC(C)(C)OC(=O)N1CC2CONC2(c2ccns2)C1]

Isopropyl alcohol (5.66 L) is cooled to 5° C. and acetyl chloride (941.23 mL, 13.23 mol) is added drop wise (exothermic). The mixture is heated to 45° C., and tert-butyl 6a-isothiazol-5-yl-1-[(4-methoxyphenyl)methyl]-3,3a,4,6-tetrahydropyrrolo[3,4-c]isoxazole-5-carboxylate (460.17 g, 1.10 mol) is added to the reactor in portions. The resulting white suspension is stirred at 45° C. for 1 hour. Most of the solvent is evaporated to give a wet, off-white solid, which is dissolved in trifluoroacetic acid (2.76 L, 36.52 mol). The resulting dark solution is heated to 70° C. and stirred at this temperature for 1 hour. The reaction mixture is cooled to room temperature and concentrated under reduced pressure. The residue is azeotroped with toluene (2×2.5 L) to give a light brown solid. The residue is dissolved in 2 M aq. HCl solution (4.6 L) and DCM (4.6 L) and stirred vigorously at 40° C. for 30 minutes until full dissolution. The mixture is cooled to room temperature and separated. The aqueous layer is washed with DCM (2×500 mL). The acidic aqueous layer is cooled to 5° C. and the pH is adjusted to 10.5 by the addition of 50% wt/wt aq. NaOH solution. The mixture is cooled to 10° C. and a solution of BOC$_2$O (252.57 g, 1.16 mol) in tetrahydrofuran (2.30 L) is added slowly. The mixture is stirred for 5 minutes and warmed to 25° C. and then stirred 1 hour longer. MTBE (2 L) is added and the resulting phases are separated. The aqueous layer is extracted with MTBE (2×1 L) and the combined organic layers are washed with brine solution (2 L), dried over MgSO$_4$, filtered, and evaporated under reduced pressure to give the crude product as an off-white solid (347.2 g). The crude solid is dissolved in boiling 7:3 v/v isohexane/ethyl acetate (2.8 L) and the resulting clear solution is allowed to slowly cool to room temperature and then cooled in an ice-bath. The resulting white suspension is filtered and washed with cold 7:3 isohexane:ethyl acetate. The white solid is dried under vacuum and nitrogen for 2 days to give the title compound as a white solid (291.30 g, 88.9%). ES/MS (m/e): 298 (M+H).

Preparation 73c tert-Butyl 3-amino-4-(hydroxymethyl)-3-isothiazol-5-yl-pyrrolidine-1-carboxylate

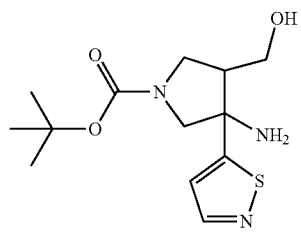 [SMILES: CC(C)(C)OC(=O)N1CC(CO)C(N)(c2ccns2)C1]

tert-Butyl 6a-isothiazol-5-yl-3,3a,4,6-tetrahydro-1H-pyrrolo[3,4-c]isoxazole-5-carboxylate (400.0 g, 1.35 mol), acetic acid (4.00 L) and zinc (439.78 g, 6.73 mol) are added together. The reaction mixture is heated to 40° C. and stirred at 40° C. for 8 hours and then cooled to room temperature. The reaction mixture is diluted with ethyl acetate (4 L), filtered through diatomaceous earth, washed with ethyl acetate, and evaporated under reduced pressure. The yellow oily residue is dissolved in toluene (2 L) and concentrated. The dissolution process with toluene is repeated 3 times. The foamy oil residue is suspended in 10% w/w aq. citric acid (3.2 L), MTBE (4 L) is added and the mixture is stirred for 15 minutes at room temperature. The biphasic mixture is filtered through diatomaceous earth (slow filtration) to remove the gel-like solids. The layers are separated and the aqueous layer is washed with MTBE (4×600 mL). The aqueous layer (pH 4.0) is added to ethyl acetate (3.0 L), and the mixture is neutralized with NaOH 50% w/w to adjust the pH=9.0-9.5 and the mixture is vigorously stirred. The organic layer is separated and the aqueous layer is extracted with ethyl acetate (3×1 L). The organic layers are combined, dried over sodium sulfate, filtered, and evaporated under reduced pressure to give the title compound as a white solid, (262.00 g, 65.1%). ES/MS (m/e): 300 (M+H).

Preparation 73d (2R,3R)-2,3-Bis[(4-methylbenzoyl)oxy]butanedioic acid; tert-butyl (3R,4R)-3-amino-4-(hydroxymethyl)-3-isothiazol-5-yl-pyrrolidine-1-carboxylate

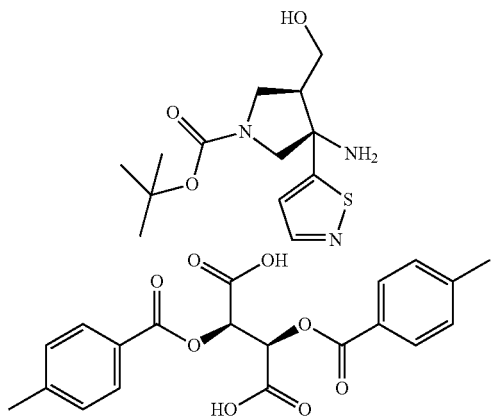

tert-Butyl 3-amino-4-(hydroxymethyl)-3-isothiazol-5-yl-pyrrolidine-1-carboxylate (262.00 g, 875.10 mmol) and isopropyl alcohol (1.83 L) are added together and the solution is heated to 70° C. Di-p-toluoyl-L-tartaric acid (338.10 g, 875.10 mmol) is added and the solid addition funnel is rinsed with additional isopropyl alcohol (262.00 mL). Complete dissolution is observed after the addition. A white solid crystallizes after 10-15 minutes. The mixture is stirred at 70° C. for 30 minutes and then cooled to room temperature overnight. The yellow suspension is filtered and the solid is washed with isopropyl alcohol (524.0 mL). The white product is dried under vacuum to a constant weight, then in a vacuum oven at 45° C. for 18 hours to give the title compound as a white crystalline solid (304.47 g, 46.7%). ES/MS (m/e): 300 (M+H of amine), ee=98.6%.

Preparation 73e tert-Butyl (3R,4R)-3-amino-4-(hydroxymethyl)-3-isothiazol-5-yl-pyrrolidine-1-carboxylate

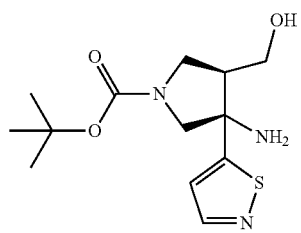 [SMILES: CC(C)(C)OC(=O)N1C[C@@H](CO)[C@](N)(c2ccns2)C1]

(2R,3R)-2,3-Bis[(4-methylbenzoyl)oxy]butanedioic acid; tert-butyl (3R,4R)-3-amino-4-(hydroxymethyl)-3-isothiazol-5-yl-pyrrolidine-1-carboxylate (389.5 g, 522.55 mmol), water (1.56 L), ethyl acetate (1.56 L) and aq. 2 M hydrogen chloride (261.28 mL, 522.55 mmol) are added together and the reaction mixture is stirred (measured at pH=2.0) for 15 minutes at room temperature. The mixture is transferred to a 5 L separator funnel, the aqueous layer is separated and washed with ethyl acetate (2×350 mL). The pH of the aq. layer is adjusted to 10 with 50% w/w aq. NaOH and then extracted with ethyl acetate (4×584 mL), each time adding more aq. 2 M NaOH in the aqueous layer to maintain the pH at 10. The organic layers are combined, dried with sodium sulfate, filtered, evaporated under reduced pressure, and dried under vacuum to give a white solid as the title compound (171.2 g, 109.43%). ES/MS (m/e): 300 (M+H). ee=97.8%.

Preparation 74 tert-Butyl (3S,4R)-3-(benzoylcarbamothioylamino)-4-(hydroxymethyl)-3-phenyl-pyrrolidine-1-carboxylate

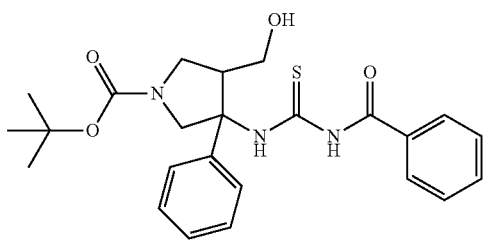 [SMILES: CC(C)(C)OC(=O)N1CC(CO)C(NC(=S)NC(=O)c2ccccc2)(c2ccccc2)C1]

A mixture of tert-butyl-1-(benzoylcarbamothioyl)-6a-phenyl-3,3a,4,6-tetrahydropyrrolo[3,4-c]isoxazole-5-carboxylate (2.3 g, 5.1 mmol), acetic acid (20 mL), and powdered zinc (3.3 g, 50 mmol) is vigorously stirred at 40° C. for 1 hour, followed by an additional hour at 45-50° C. The reaction is concentrated under reduced pressure. To the residue is added diatomaceous earth and water, followed by a saturated solution of sodium bicarbonate. The mixture is filtered and washed with ethyl acetate. The filtrate is extracted with ethyl acetate. The organic layers are combined, dried over sodium sulfate, filtered, and concentrated under reduced pressure to give a residue. The residue is purified by silica gel flash chromatography, eluting with hexane/ethyl acetate (1:0) to hexane/ethyl acetate (0:1) to give the title compound (1.6 g, 70%). ES/MS (m/e): 456 (M+H).

Preparation 74

Alternate Preparation tert-Butyl 3-(benzoylcarbamothioylamino)-4-(hydroxymethyl)-3-phenyl-pyrrolidine-1-carboxylate

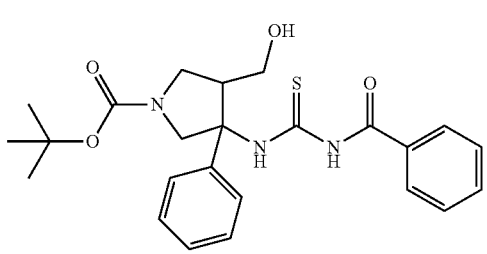 [SMILES: CC(C)(C)OC(=O)N1CC(CO)C(NC(=S)NC(=O)c2ccccc2)(c2ccccc2)C1]

Benzoyl isothiocyanate (81.37 µL, 603.33 mmol) is added to a 0° C. solution of tert-butyl 3-amino-4-(hydroxymethyl)-3-phenyl-pyrrolidine-1-carboxylate (0.168 g, 574.60 mmol) in tetrahydrofuran (2.3 mL). The mixture is warmed to room temperature and stirred overnight. Benzoyl isothiocyanate (15.50 µL, 114.92 mmol) is added and the mixture is stirred for 2 hr. Sodium bicarbonate solution and dichloromethane are added and the aqueous layer is separated, the aqueous mixture is extracted with dichloromethane (3×25 mL), dried over sodium sulfate, filtered, and concentrated to dryness. The crude product is purified via silica gel chromatography eluting with 0-100% ethyl acetate/hexanes to give the title compound (0.178 g, 68%). ES/MS (m/e): 454.3 (M−1).

Preparation 75 tert-Butyl 3-(benzoylcarbamothioylamino)-4-(hydroxymethyl)-3-(2-thienyl)pyrrolidine-1-carboxylate

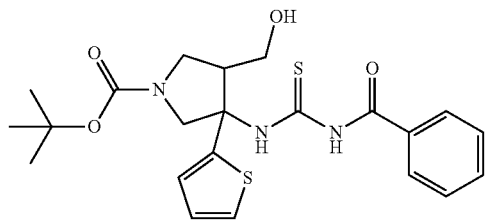 [SMILES: CC(C)(C)OC(=O)N1CC(CO)C(NC(=S)NC(=O)c2ccccc2)(c2cccs2)C1]

Acetic acid (104 mL) is added to tert-butyl-1-(benzoylcarbamothioyl)-6a-(2-thienyl)-3,3a,4,6-tetrahydropyrrolo[3,4-c]isoxazole-5-carboxylate followed by powdered zinc (17.1 g, 261 mmol) and the resulting suspension is vigorously stirred at 40° C. for 7 hours followed by an additional hour at 45-50° C. The reaction is concentrated under reduced pressure. To the crude reaction mixture is added diatomaceous earth and water, followed by a saturated solution of sodium bicarbonate. The mixture is filtered and washed with ethyl acetate. The filtrate is extracted with ethyl acetate. The organic layers are combined, dried over sodium sulfate, filtered, and concentrated under reduced pressure to give a residue. The residue is purified by silica gel flash chromatography, eluting with hexane/ethyl acetate (1:0) to hexane/ethyl acetate (0:1) to give the title compound (3.8 g, 32%). ES/MS (m/e): 460 (M−1).
The following compound is prepared essentially by the method of Preparation 75 and the reaction is stirred for 1 hour 5 minutes at room temperature.

Preparation 77

Racemic Benzyl 2-benzamido-7a-(3-bromophenyl)-4,4a,5,7-tetrahydropyrrolo[3,4-d][1,3]thiazine-6-carboxylate

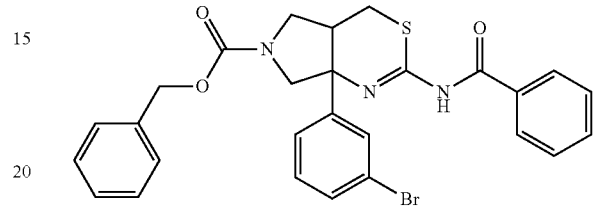

To a solution of benzyl 1-(benzoylcarbamothioyl)-6a-(3-bromophenyl)-3,3a,4,6-tetrahydropyrrolo[3,4-c]isoxazole-5-carboxylate (1.9 g, 3.3 mmol) in acetic acid (30 mL) is added powered zinc (2.0 g, 30 mmol). The resultant suspension is sonicated for 2 hours before being filtered through a pad of diatomaceous earth. The diatomaceous earth pad is washed with ethyl acetate. The combined filtrates are concentrated to dryness then diluted with ethyl acetate (100 mL) and washed with saturated sodium bicarbonate (100 mL). The aqueous layer is re-extracted with ethyl acetate (50 mL) and chloroform (50 mL). The combined organic layers are dried over magnesium sulfate, filtered, and concentrated. The residue is then dissolved in dichloromethane (30 mL) and treated with 1-chloro-N,N,2-trimethylpropenylamine (1.0 mL, 7.6 mmol). The resultant solution is stirred at ambient temperature for 3.3 hours and concentrated to dryness. The residue is purified by silica gel flash chromatography, eluting with gradient of ethyl acetate/dichloromethane (0 to 40%) to give the title compound (1.86 g, 100%). ES/MS (m/e): ($^{79}$Br/$^{81}$Br) 550/552 (M+H).

TABLE 16

| Prep. No. | Chemical name | Structure | ES/MS (m/e) |
|---|---|---|---|
| 76 | tert-Butyl (3R,4R)-3-(benzoylcarbamothioylamino)-4-(hydroxymethyl)-3-isothiazol-5-yl-pyrrolidine-1-carboxylate | 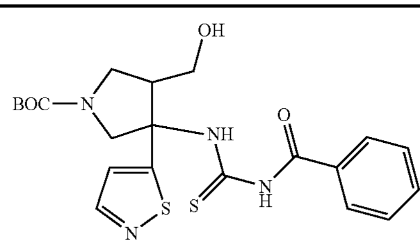 | 463 (M + H) |

Preparation 78

Racemic N-[7a-(2-Fluorophenyl)-4a,5,6,7-tetrahydro-4H-pyrrolo[3,4-d][1,3]thiazin-2-yl]benzamide

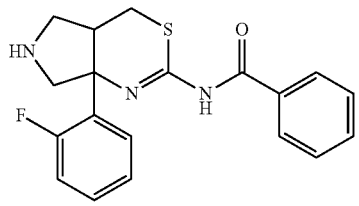 [SMILES: O=C(NC1=NC2(c3ccccc3F)CNCC2CS1)c1ccccc1]

Racemic tert-butyl 3-(benzoylcarbamothioylamino)-3-(2-fluorophenyl)-4-(hydroxymethyl)pyrrolidine-1-carboxylate (2.1 g, 4.39 mmol) is dissolved in dichloromethane (75 mL) and partitioned in equal portions between three reaction vessels. The reaction vessels are cooled to 0° C., and to each vessel is added drop wise 1-chloro-N,N,2-trimethylpropenylamine (2.0 mL, 15 mmol). The reactions are warmed to 22° C., and stirred for 4 hours. The contents of each vessel are passed through a 10 g silica gel plug, washed with methanol (30 ml), and the solvent removed under reduced pressure. The residues are purified by reverse phase HPLC eluting with a gradient of 5 to 100% acetonitrile in 10 mM ammonium bicarbonate solution w/5% methanol (pH 10.0) to give the title compound (3.1 g). ES/MS (m/e): 356 (M+H).

Preparation 79

Racemic tert-Butyl-2-benzamido-7a-phenyl-4,4a,5,7-tetrahydropyrrolo[3,4-d][1,3]thiazine-6-carboxylate

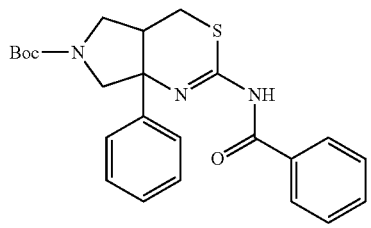 [SMILES: CC(C)(C)OC(=O)N1CC2CSC(NC(=O)c3ccccc3)=NC2(c2ccccc2)C1]

A solution of tert-butyl-3-(benzoylcarbamothioylamino)-4-(hydroxymethyl)-3-phenyl-pyrrolidine-1-carboxylate (1.6 g, 3.5 mmol) in dichloromethane (87 mL) at 0° C. is treated with 1-chloro-N,N,2-trimethylpropenylamine (0.94 mg, 7.0 mmol). The mixture is allowed to warm to room temperature and stirred for 4 hours under nitrogen. Saturated sodium bicarbonate is added and the solution extracted with dichloromethane. The combined organic layers are dried over sodium sulfate, filtered, and concentrated to give a residue. The residue is purified by silica gel flash chromatography, eluting with hexane/ethyl acetate (1:0) to hexane/ethyl acetate (0:1) to give the title compound, which is used without further purification (1.6 g, 104%). ES/MS (m/e): 438 (M+H). The following compounds are prepared essentially by the method of Preparation 79.

TABLE 17

| Prep. No. | Chemical name | Structure | ES/MS (m/e) |
|---|---|---|---|
| 80[a] | Racemic tert-Butyl 2-benzamido-7a-isothiazol-5-yl-4,4a,5,7-tetrahydropyrrolo[3,4-d][1,3]thiazine-6-carboxylate | 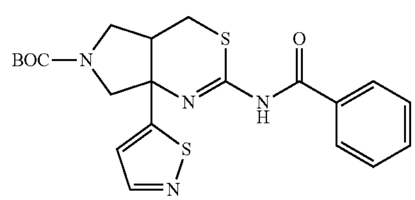 [SMILES: CC(C)(C)OC(=O)N1CC2CSC(NC(=O)c3ccccc3)=NC2(c2ccns2)C1] | 445 (M + H) |
| 81 | Racemic tert-Butyl 2-benzamido-7a-(4-bromo-2-thienyl)-4,4a,5,7-tetrahydropyrrolo[3,4-d][1,3]thiazine-6-carboxylate | 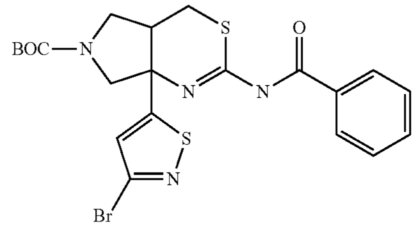 [SMILES: CC(C)(C)OC(=O)N1CC2CSC(NC(=O)c3ccccc3)=NC2(c2cc(Br)ns2)C1] | ($^{79}$Br/$^{81}$Br) 522/524 (M + H) |

[a]Preparation 80 is stirred for 18 hours.

Preparation 82 tert-Butyl (4aR,7aR)-2-benzamido-7a-isothiazol-5-yl-4,4a,5,7-tetrahydropyrrolo[3,4-d][1,3]thiazine-6-carboxylate

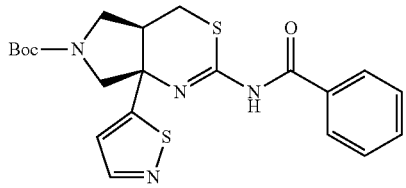 [SMILES: CC(C)(C)OC(=O)N1C[C@H]2CSC(NC(=O)c3ccccc3)=N[C@@]2(c2ccns2)C1]

Racemic tert-Butyl-2-benzamido-7a-isothiazol-5-yl-4,4a,5,7-tetrahydropyrrolo[3,4-d][1,3]thiazine-6-carboxylate is separated into its constituent enantiomers by chiral SFC (Column: Chiralpak IC 50×150 mm; eluent: 40% methanol:60% $CO_2$; flow: 300 mL/min at UV 240 nm). Analysis of the second eluting isomer (Column: Chiralpack IC 4×150 mm; eluent: 40% methanol:60% $CO_2$; flow: 5.000 mL/min at UV 240 nm) confirms the enantiomerically enriched (>98.8% ee) enantiomer with $R_t$=3.60 minutes, (652.5 mg, 34%).

Preparation 82a tert-Butyl (4aR,7aR)-2-benzamido-7a-isothiazol-5-yl-4,4a,5,7-tetrahydropyrrolo[3,4-d][1,3]thiazine-6-carboxylate

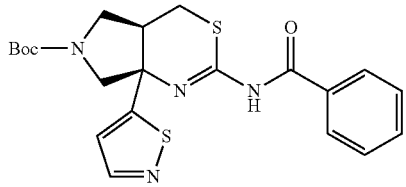 [SMILES: CC(C)(C)OC(=O)N1C[C@H]2CSC(NC(=O)c3ccccc3)=N[C@@]2(c2ccns2)C1]

tert-Butyl (3R,4R)-3-amino-4-(hydroxymethyl)-3-isothiazol-5-yl-pyrrolidine-1-carboxylate (148.10 g, 494.67 mmol) and tetrahydrofuran (1.48 L) are added together and the solution is cooled to 0° C. Benzoyl isothiocyanate (82.34 g, 504.56 mmol) is added over 5 minutes and the reaction mixture is stirred for 30 minutes at 0° C. and then warmed to room temperature over 1 hour. 1,1'-Carbonyldiimidazole (92.24 g, 568.87 mmol) is added and the reaction mixture is stirred at room temperature for 2 h. The mixture is heated to 65° C. and stirred for a further 12 hours. The reaction mixture is concentrated under reduced pressure and the oily residue is partitioned between water (1.5 L) and ethyl acetate (1.5 L). The pH is adjusted with citric acid 50% w/w aq. solution to 4.0 and the organic layer is separated. The aqueous layer is extracted with MTBE (2×500 mL), the organics are combined, dried over sodium sulfate, filtered, and evaporated under reduced pressure. The crude product is slurried in MTBE (740.50 mL) at 60° C. then at room temperature for 45 minutes. The solid is collected, washed with MTBE (4×150 mL), and dried under vacuum overnight to give the title compound as an off white solid (162.68 g, 74.0%). ES/MS (m/e): 445 (M+H), ee=99.5%.

Preparation 83 tert-Butyl (4aR,7aS)-2-(benzolyamino)-7a-phenyl-4a,5,7,7a-tetrahydropyrrolo[3,4-d][1,3]thiazine-6 (4H)-carboxylate

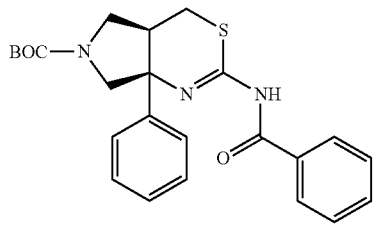 [SMILES: CC(C)(C)OC(=O)N1C[C@H]2CSC(NC(=O)c3ccccc3)=N[C@@]2(c2ccccc2)C1]

Racemic tert-butyl-2-benzamido-7a-phenyl-4,4a,5,7-tetrahydropyrrolo[3,4-d][1,3]thiazine-6-carboxylate (1.6 g, 3.66 mmol) is dissolved in ethanol/chloroform (30 ml/14 ml) and is separated into its constituent enantiomers by chiral SFC (Supercritical Fluid Chromatography) (Chiralpak AD 8×40.5 cm (20 μm); eluent: 100% ethanol in $CO_2$; flow: 350 mL/min at UV 280 nm; 0.4 g/injection). The first eluting isomer is the title compound (593 mg, 37%). Chiral analysis of this isomer: (Chiralpak AD-H 4.6×150 mm; eluent: 100% ethanol with 0.2% isopropyl amine) in $CO_2$; flow 1 mL/min at UV 225 nm) $R_t$=3.03 to (>98% ee). ES/MS (m/e): 438 (M+H).

Alternate Preparation 83

Racemic tert-butyl-2-benzamido-7a-phenyl-4,4a,5,7-tetrahydropyrrolo[3,4-d][1,3]thiazine-6-carboxylate (5.23 g, 11.9 mmol) is chirally purified by SFC: (Column: Chiralpak IC 2.1×25 cm; eluent: 40% methanol $CO_2$; flow: 300 mL/min at UV 284 nm). The second eluting isomer is the title compound (1.7, 34%, >98% ee). Chiral analysis of the isolated isomer 2: Chiralpak IC 0.46×10 cm, 5 um; eluent: 40% methanol in $CO_2$; flow: 5 mL/min at UV 215 nm. $R_t$=1.48 minutes. $[\alpha]_D^{20}$=−88 (C=1.0, methanol), ES/MS (m/e): 438.3 (M+H).

Preparation 84 tert-Butyl (4aR,7aR)-2-benzamido-7a-(2-thienyl)-4,4a,5,7-tetrahydropyrrolo[3,4-d][1,3]thiazine-6-carboxylate

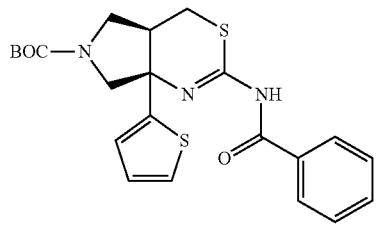 [SMILES: CC(C)(C)OC(=O)N1C[C@H]2CSC(NC(=O)c3ccccc3)=N[C@@]2(c2cccs2)C1]

To a solution of racemic tert-butyl 3-(benzoylcarbamothioylamino)-4-(hydroxymethyl)-3-(2-thienyl)pyrrolidine-1-carboxylate (3.8 g, 8.23 mmol) in dichloromethane (206 mL) cooled to 0° C. is added drop wise 1-chloro-N,N,2-trimethylpropenylamine (2.18 mL, 16.46 mmol). The reaction is warmed to room temperature and is stirred for 2 hours. To the reaction mixture is added a saturated solution of sodium bicarbonate and dichloromethane. The mixture is extracted with dichloromethane. The organic layers are combined, dried over sodium sulfate, filtered, and concentrated to give a residue. The residue is purified by silica gel flash chromatography, eluting with hexane/ethyl acetate (1:0) to hexane/ethyl acetate (0:1) to give the title compound (3.30 g, 90%). ES/MS (m/e): 444 (M+H). The racemic tert-butyl-3-(benzoylcarbamothioylamino)-4-(hydroxymethyl)-3-phenyl-pyrrolidine-1-carboxylate (3.2 g, 7.4 mmol) is dissolved in methanol/chloroform (36 ml/25 ml) and is separated into its constituent enantiomers by chiral SFC (Chiralpak OJ-H 50×250 mm; eluent: 25% methanol in 75% $CO_2$; flow 300 g/min at UV 240 nm; column temperature −40° C.; 0.64 g/injection). Analysis of isolated enantiomer (Chiralpak OJ-H 4.6×150 mm; eluent: 25% methanol in 75% $CO_2$; flow 5 mL/min at UV 240 nm, column temperature −35° C.) gave the title compound with $R_t$=1.5 min, isomer 1, (1.27 g, 39%, >99% ee).

Preparation 85

Racemic N-[6-Allyl-7a-(5-fluoro-2-thienyl)-4,4a,5,7-tetrahydropyrrolo[3,4-d][1,3]thiazin-2-yl]benzamide

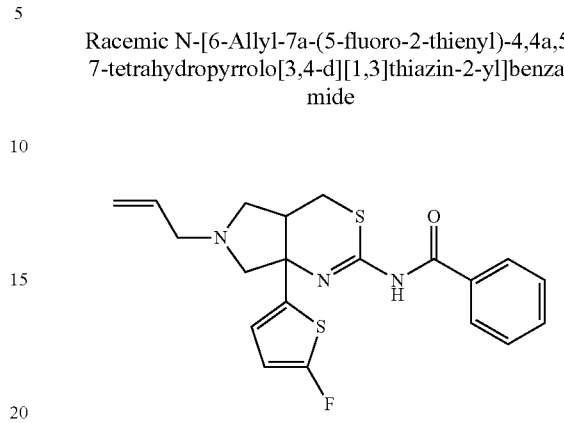

To a stirred solution of racemic N-[[1-allyl-3-(5-fluoro-2-thienyl)-4-(hydroxymethyl)pyrrolidin-3-yl]carbamothioyl]benzamide (320 mg, 0.763 mmol) in dichloromethane (7.6 mL) at 0° C. under nitrogen is added 1-chloro-N,N,2-trimethylpropenylamine (0.2 mL, 1.53 mmol). The solution is stirred while slowly warming to 10° C. over 2 hours. The ice bath is removed and the reaction is warmed to room temperature over another 2 hours. The solution is diluted with dichloromethane (approximately 40 mL) and washed with dilute sodium bicarbonate (40 mL prepared from water (20 mL) and saturated sodium bicarbonate (20 mL)). The aqueous phase is re-extracted with dichloromethane (40 mL). The combined organic extracts are dried over sodium sulfate, filtered, and concentrated. The residue is purified by silica gel chromatography eluting with hexanes/ethyl acetate, two-step gradient from 60:40 to 50:50, to give the title compound (186 mg, 61%). ES/MS (m/e): 402 (M+H).

The following compounds are prepared essentially by the method of Preparation 85 using the appropriate benzamide.

TABLE 18

| Prep No. | Chemical name | Structure | ES/MS (m/e) |
|---|---|---|---|
| 86 | Racemic N-[6-Allyl-7a-(4-bromo-2-thienyl)-4,4a,5,7-tetrahydropyrrolo[3,4-d][1,3]thiazin-2-yl]benzamide | 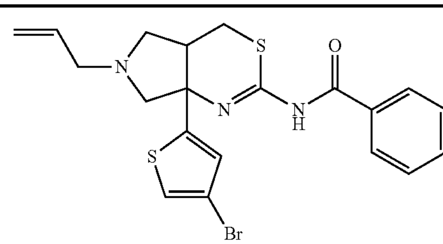 | ($^{79}$Br/$^{81}$Br) 462/464 (M + H) |
| 87 | Racemic N-[6-Allyl-7a-(4-fluorophenyl)-4,4a,5,7-tetrahydropyrrolo[3,4-d][1,3]thiazin-2-yl]benzamide | 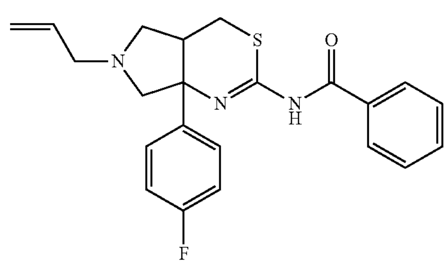 [SMILES: C=CCN1CC2CSC(NC(=O)c3ccccc3)=NC2(c2ccc(F)cc2)C1] | 396 (M + H) |

Preparation 88

N-[(4aR,7aR)-6-Allyl-7a-(4-bromo-2-thienyl)-4,4a,5,7-tetrahydropyrrolo[3,4-d][1,3]thiazin-2-yl]benzamide, isomer 2

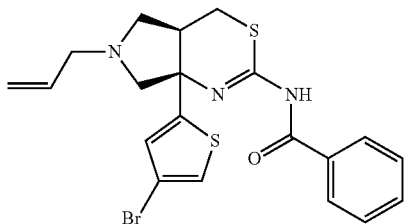 [SMILES: C=CCN1C[C@H]2CSC(NC(=O)c3ccccc3)=N[C@@]2(c2cc(Br)cs2)C1]

Racemic N-[6-Allyl-7a-(4-bromo-2-thienyl)-4,4a,5,7-tetrahydropyrrolo[3,4-d][1,3]thiazin-2-yl]benzamide (2.24 g, 4.84 mmol) is purified by chiral HPLC: (Chiralpak AD 8×40.5 cm; eluent: 100% ethanol with 0.2% dimethylethyl amine); flow: 400 mL/min at UV 270 nm). Analysis conditions: Chiralpak AD-H 0.46×15 cm; eluent: 100% ethanol (0.2% isopropyl amine); flow: 0.6 mL/min at UV 320 nm; $R_t$=3.03 minutes. The second eluting isomer is isolated to give the title compound (1.08 g, 48%, >99% ee). ES/MS (m/e) ($^{79}$Br/$^{81}$Br) 462/464 (M+H).

Preparation 89

N-[(4aR,7aR)-7a-(5-Fluorothiophen-2-yl)-6-(prop-2-en-1-yl)-4,4a,5,6,7,7a-hexahydropyrrolo[3,4-d][1,3]thiazin-2-yl]benzamide

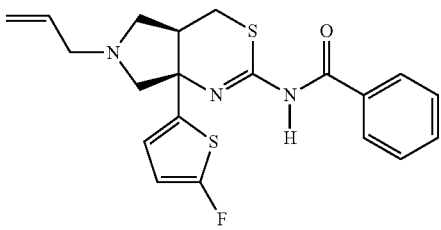 [SMILES: C=CCN1C[C@H]2CSC(NC(=O)c3ccccc3)=N[C@@]2(c2ccc(F)s2)C1]

Racemic N-[6-allyl-7a-(5-fluoro-2-thienyl)-4,4a,5,7-tetrahydropyrrolo[3,4-d][1,3]thiazin-2-yl]benzamide (4.71 g, 11.73 mmol) is dissolved in 1:1 MeOH/CHCl$_3$ (20 mg/mL) and separated into its constituent enantiomers by chiral HPLC (Column: Chiralcel OD 8×32 cm (20 μM); mobile phase: 60:40 IPA/heptane; flow rate 385 mL/min at UV 290 nm; 0.320 g/injection). Analysis of the second eluting isomer (Column: Chiralcel OD-H 4.6×150 mm; mobile phase: 60:40 IPA/heptane; flow rate 0.6 mL/min at UV 290 nm) gave the title compound, $R_t$=8.2 minutes (2.01 g, 43%, 96.1% ee). ES/MS (m/e): 402.0 (M+H).

Preparation 90

Racemic N-(6-Allyl-7a-thiazol-5-yl-4,4a,5,7-tetrahydropyrrolo[3,4-d][1,3]thiazin-2-yl)benzamide

To a solution of N-[[1-allyl-4-(hydroxymethyl)-3-thiazol-5-yl-pyrrolidin-3-yl]carbamothioyl]benzamide (60 mg, 150 μmoles) in tetrahydrofuran (1 mL) at 0° C. is added triphenylphosphine (80 mg, 30 μmoles) and di-t-butyl azodicarboxylate (88 mg, 30 μmoles). The mixture is stirred for 30 minutes at 0° C., warmed to room temperature and stirred for 1 hour. The mixture is concentrated and purified over silica gel eluting with methanol/dichloromethane (0-5%) to give the title product (26 mg, 70 p moles, 45%). ES/MS (m/e): 385 (M+H).

Preparation 91

Racemic Benzyl 2-benzamido-7a-phenyl-4,4a,5,7-tetrahydropyrrolo[3,4-d][1,3]thiazine-6-carboxylate

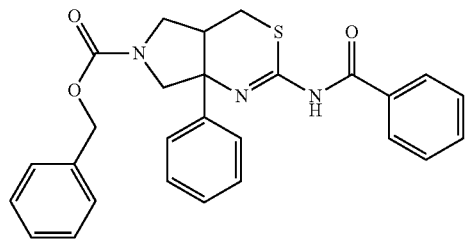 [SMILES: O=C(NC1=NC2(c3ccccc3)CN(C(=O)OCc3ccccc3)CC2CS1)c1ccccc1]

1-Chloro-N,N,2-trimethylpropenylamine (17.9 mL, 135 mmol) is added to a 0° C. solution of racemic benzyl 3-(benzoylcarbamothioylamino)-4-(hydroxymethyl)-3-phenyl-pyrrolidine-1-carboxylate (51 g, 104 mmol) in dichloromethane (459 mL) and stirred at room temperature for 2 hours. A saturated solution of sodium hydrogen carbonate (300 mL) is added and the layers are separated. The organic layer is dried over magnesium sulfate, the solution concentrated. The crude product is purified over silica gel eluting with dichloromethane to 5% ethyl acetate/dichloromethane to give the title compound (31 g, 63%). ES/MS (m/e): 372 (M+H).

Preparation 92

Racemic Benzyl 2-benzamido-7a-(2-thienyl)-4,4a,5,7-tetrahydropyrrolo[3,4-d][1,3]thiazine-6-carboxylate

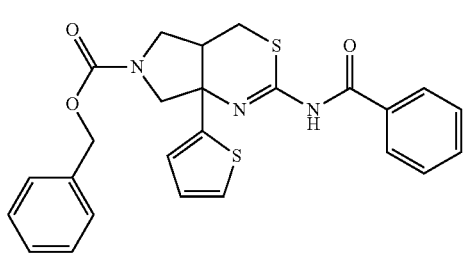 [SMILES: O=C(NC1=NC2(c3cccs3)CN(C(=O)OCc3ccccc3)CC2CS1)c1ccccc1]

To a 0° C. solution of racemic benzyl 3-(benzoylcarbamothioylamino)-4-(hydroxymethyl)-3-(2-thienyl)pyrrolidine-1-carboxylate (30 g, 60.5 mmol) in methylene chloride (300 mL) is added a methylene chloride solution (20 mL) of 1-chloro-N,N,2-trimethylpropenylamine (9.61 mL, 72.6 mmol). The resulting solution is stirred at 0° C. for 30 minutes and then warmed to room temperature. The solution is quenched with saturated sodium bicarbonate solution, the organic layer is isolated, dried over sodium sulfate and concentrated. The crude mixture is purified over silica gel eluting with 5% to 50% ethyl acetate in hexanes gradient to give the title compound (24 g, 83%). ES/MS (m/e): 478 (M+H).
The following compound is prepared essentially by the method of Preparation 92 using the appropriate benzamide.

Preparation 95

Benzyl (4aR,7aR)-2-benzamido-7a-thiazol-5-yl-4,4a,5,7-tetrahydropyrrolo[3,4-d][1,3]thiazine-6-carboxylate, isomer 1

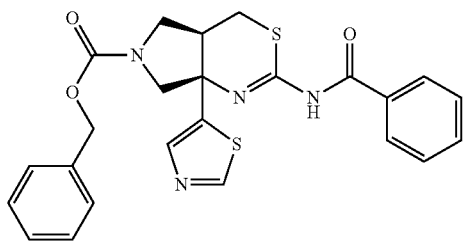

TABLE 19

| Prep No. | Chemical name | Structure | ES/MS (m/e) |
|---|---|---|---|
| 93 | Racemic Benzyl 2-benzamido-7a-(2-trimethylsilylthiazol-5-yl)-4,4a,5,7-tetrahydropyrrolo[3,4-d][1,3]thiazine-6-carboxylate | 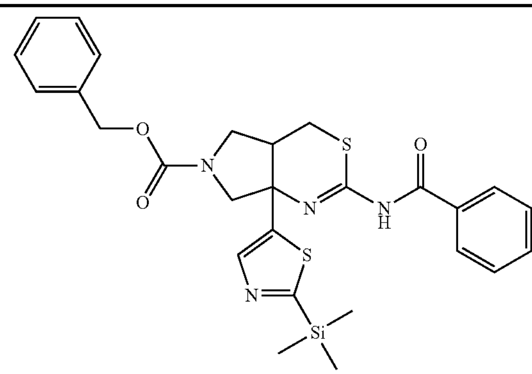 | 551 (M + H) |

Preparation 94

Racemic Benzyl 2-benzamido-7a-thiazol-5-yl-4,4a,5,7-tetrahydropyrrolo[3,4-d][1,3]thiazine-6-carboxylate

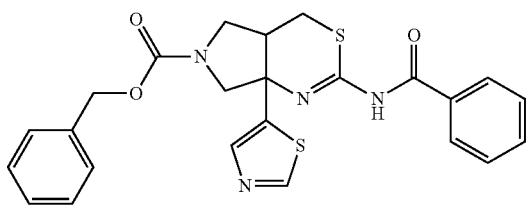 [SMILES: O=C(NC1=NC2(c3cncs3)CN(C(=O)OCc3ccccc3)CC2CS1)c1ccccc1]

To a solution of racemic benzyl 2-benzamido-7a-(2-trimethylsilylthiazol-5-yl)-4,4a,5,7-tetrahydropyrrolo[3,4-d][1,3]thiazine-6-carboxylate (117 mg, 212 µmoles) in tetrahydrofuran (4 mL) is added 1 N tetrabutylammonium fluoride (1 N in tetrahydrofuran) (425 µL, 425 µmoles) and the mixture is stirred under nitrogen for one hour. The solution is diluted with water, extracted with ethyl acetate (3×), dried over sodium sulfate and concentrated. The crude product is purified over silica gel eluting with ethyl acetate/hexanes (5% to 100%) to give the title compound (89 mg, 88%). ES/MS (m/e): 479 (M+H).

Racemic benzyl 2-benzamido-7a-thiazol-5-yl-4,4a,5,7-tetrahydropyrrolo[3,4-d][1,3]thiazine-6-carboxylate (1.173 g, 2.45 mmol) is purified by chiral HPLC: (Column: Chiralpak AS 8×33 cm; eluent: 100% methanol; flow: 400 mL/min at UV 240 nm), to give the title product as the first eluting isomer with $R_t$=3.43 minutes, (422 mg, 36%, >99% ee). Analysis column: Chiralpak AS-H 4.6×150 mm; eluent: 99.8% methanol with 0.2% isopropylamine; flow: 1.0 mL/min at UV 225 nm). ES/MS (m/e): 479 (M+H).

Preparation 96

Benzyl (4aR,7aS)-2-benzamido-7a-phenyl-4,4a,5,7-tetrahydropyrrolo[3,4-d][1,3]thiazine-6-carboxylate

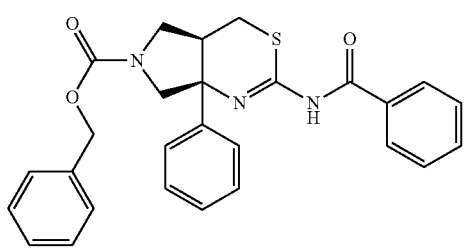 [SMILES: O=C(NC1=N[C@@]2(c3ccccc3)CN(C(=O)OCc3ccccc3)C[C@H]2CS1)c1ccccc1]

Racemic benzyl 2-benzamido-7a-phenyl-4,4a,5,7-tetrahydropyrrolo[3,4-d][1,3]thiazine-6-carboxylate (30 g, 63 mmol) is chirally purified by SFC: (Column: Chiralpak IC 2.1×25 cm; eluent: 40% methanol/acetonitrile (8/2) with 0.2% dimethylethyl amine in CO$_2$; flow: 70 mL/min at UV 284 nm). The second eluting isomer is the title compound (11.1 g, 37%, >98% ee). Chiral analysis of the isolated isomer 2: Chiralpak IC 0.46×10 cm, 5 µm; eluent: 40% methanol/acetonitrile (8/2) with 0.2% dimethyl ethyl amine in CO$_2$; flow: 5 mL/min at UV 215 nm. R$_f$=3.2 minutes. $[\alpha]_D^{20}$=−88 (C=1.0, methanol), ES/MS (m/e) 372 (M+H)

Preparation 97

Benzyl (4aR,7aR)-2-benzamido-7a-(2-thienyl)-4,4a,5,7-tetrahydropyrrolo[3,4-d][1,3]thiazine-6-carboxylate

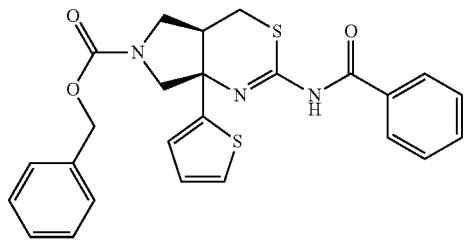 [SMILES: O=C(NC1=N[C@@]2(c3cccs3)CN(C(=O)OCc3ccccc3)C[C@H]2CS1)c1ccccc1]

Racemic benzyl 2-benzamido-7a-(2-thienyl)-4,4a,5,7-tetrahydropyrrolo[3,4-d][1,3]thiazine-6-carboxylate (34 g, 63 mmol) is chirally purified by SFC (Column: Chiralpak IC (5µ), 2×250 mm; eluent: 40% methanol/acetonitrile (8/2) with 0.2% diethylmethyl amine) in CO$_2$; flow: 65 mL/min at UV 260 nm). The second eluting isomer is the title compound (14 g, 42%, >98% ee): $[\alpha]_D^{20}$=−30 (C=1.0, methanol), ES/MS (m/e) 478 (M+H).

Preparation 98

Benzyl (4aR,7aR)-2-(benzoylamino)-7a-(5-bromothiophen-2-yl)-4a,5,7,7a-tetrahydropyrrolo[3,4-d][1,3]thiazine-6(4H)-carboxylate

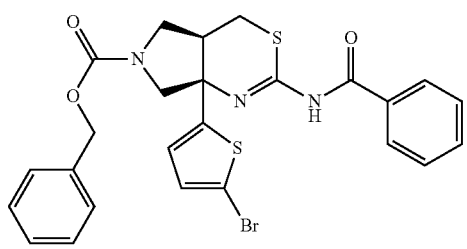 [SMILES: O=C(NC1=N[C@@]2(c3ccc(Br)s3)CN(C(=O)OCc3ccccc3)C[C@H]2CS1)c1ccccc1]

To a stirred clear and colorless solution of benzyl (4aR,7aR)-2-benzamido-7a-(2-thienyl)-4,4a,5,7-tetrahydropyrrolo[3,4-d][1,3]thiazine-6-carboxylate (1.67 g, 3.50 mmol) in dimethylformamide (35 mL) at room temperature, under an atmosphere of nitrogen is added N-bromosuccinimide (747 mg, 4.20 mmol). The resulting pale yellow solution is stirred at room temperature for 50 minutes. The solution is diluted with ethyl acetate (150 mL) and washed with water (3×50 mL) and brine (50 mL). The organic phase is separated, dried over sodium sulfate, filtered, and concentrated under reduced pressure. The residue is purified by silica gel flash chromatography eluting with a hexanes/ethyl acetate, gradient from 80:20 to 0:100, to give the title compound (1.79 g, 92%) as a white solid: ES/MS (m/z): 557.8 (M+H).

Preparation 99

Benzyl (4aR,7aR)-2-(benzoylamino)-7a-(5-cyanothiophen-2-yl)-4a,5,7,7a-tetrahydropyrrolo[3,4-d][1,3]thiazine-6(4H)-carboxylate

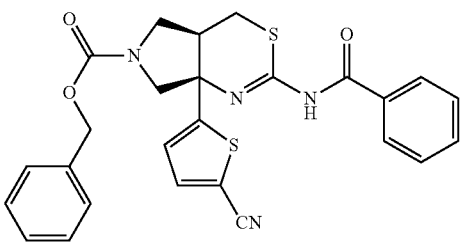 [SMILES: N#Cc1ccc([C@]23CN(C(=O)OCc4ccccc4)C[C@H]2CSC(NC(=O)c2ccccc2)=N3)s1]

Benzyl (4aR,7aR)-2-(benzoylamino)-7a-(5-bromothiophen-2-yl)-4a,5,7,7a-tetrahydropyrrolo[3,4-d][1,3]thiazine-6(4H)-carboxylate (3.88 g, 6.97 mmol), anhydrous potassium hexacyanoferrate (II) (2.57 g, 6.97 mmol) (prepared as cited in Schareina, T.; et al Synthesis, 2008, 20, 3351-3355), copper (I) iodide (398 mg, 2.09 mmol), 1-butylimidazole (2.8 mL, 20.9 mmol), and toluene (23 mL) are added to a 60 mL glass pressure tube fitted with a stirrer bar. A stream of nitrogen is passed over the mixture for a few minutes and the pressure tube is then sealed. The stirred mixture is heated at 145° C. for 18 hours. The resulting dark mixture is cooled to room temperature. The mixture is diluted with ethyl acetate (100 mL) and water (15 mL) and vacuum filtered through a pad of diatomaceous earth while rinsing with ethyl acetate (100 mL) and water (15 mL). The layers of the filtrate are separated and the organic layer is further washed with water (2×30 mL) and brine (30 mL). The organic phase is dried over sodium sulfate, filtered, and concentrated under reduced pressure. The residue is purified by silica gel flash chromatography eluting with a hexanes/ethyl acetate, gradient from 80:20 to 0:100, to give the title compound (2.59 g, 74%) as a white foam: ES/MS (m/z): 503.2 (M+H).

Preparation 100

N-[(4aR,7aS)-7a-Phenyl-4a,5,6,7-tetrahydro-4H-pyrrolo[3,4-d][1,3]thiazin-2-yl]benzamide hydrochloride

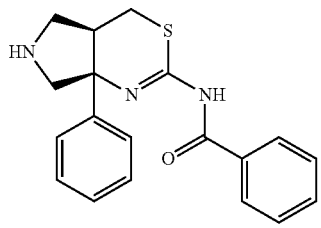

tert-Butyl (4aR,7aS)-2-(benzolyamino)-7a-phenyl-4a,5,7,7a-tetrahydropyrrolo[3,4-d][1,3]thiazine-6(4H)-carboxylate (590 mg, 1.35 mmol) and hydrogen chloride (4 M in 1,4-dioxane, 5 mL) is stirred at ambient temperature for 5 hours. The reaction is concentrated to give the title compound, which is used without further purification (0.505 g, 94%). ES/MS (m/e): 338 (M+H).

Preparation 101

N-[(4aR,7aR)-7a-(2-Thienyl)-4a,5,6,7-tetrahydro-4H-pyrrolo[3,4-d][1,3]thiazin-2-yl]benzamide hydrochloride

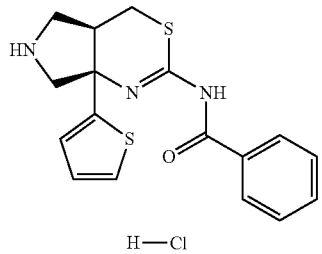 [SMILES: O=C(NC1=N[C@@]2(c3cccs3)CNC[C@H]2CS1)c1ccccc1 ; Cl]

To a solution of tert-butyl (4aR,7aR)-2-benzamido-7a-(2-thienyl)-4,4a,5,7-tetrahydropyrrolo[3,4-d][1,3]thiazine-6-carboxylate (1.3 g, 2.93 mmol) in 1,4 dioxane (60 mL) is added drop wise 4 N hydrogen chloride in 1,4-dioxane (14.6 mL, 58.6 mmol). The reaction is stirred for 4 hours. The solution is concentrated to give the title compound (1.1 g, 99%). ES/MS (m/e): 344 (M+H).

The following compound is prepared essentially by the method of Preparation 101.

To a room temperature solution of tert-butyl (4aR,7aR)-2-benzamido-7a-isothiazol-5-yl-4,4a,5,7-tetrahydropyrrolo[3,4-d][1,3]thiazine-6-carboxylate, isomer 2 (1.26 g, 2.83 mmol) in dichloromethane (25 mL) is added trifluoroacetic acid (4.29 mL, 56.68 mmol) drop wise. The resultant solution is stirred for 18 hours at ambient temperature. The solvent is removed under vacuum. The mixture is diluted with ethyl acetate followed by saturated sodium bicarbonate. The layers are separated and the aqueous phase is re-extracted with ethyl acetate (3×). The combined organic layers are dried over sodium sulfate and the solvent is removed under vacuum to give the title compound (850 mg, 2.46 mmol, 87%). ES/MS (m/e): 345 (M+H).

Prep 103a

N-[(4aR,7aR)-7a-Isothiazol-5-yl-4a,5,6,7-tetrahydro-4H-pyrrolo[3,4-d][1,3]thiazin-2-yl]benzamide hydrochloride

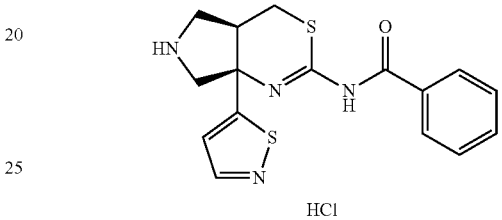

Hydrogen chloride 6 M in 2-propanol (1.65 L, 9.9 mol) is added to tert-butyl (4aR,7aR)-2-benzamido-7a-isothiazol-5-yl-4,4a,5,7-tetrahydropyrrolo[3,4-d][1,3]thiazine-6-carboxylate (200 g, 449.9 mol) in 2-propanol (1.6 L) at 22° C. and stirred for 18 hours. The mixture is concentrated to give a white solid. The solid is diluted with MTBE (1 L), stirred at 22° C. for 1 hour, filtered and dried under vacuum to constant weight to give the title compound (170 g, 98%). ES/MS (m/e): 345.0 (M+H).

TABLE 20

| Prep No. | Chemical name | Structure | ES/MS (m/e) |
|---|---|---|---|
| 102 | Racemic N-[7a-(4-Bromo-2-thienyl)-4a,5,6,7-tetrahydro-4H-pyrrolo[3,4-d][1,3]thiazin-2-yl]benzamide hydrochloride | 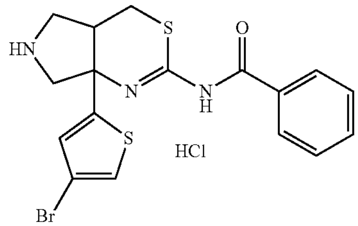 [SMILES: O=C(NC1=NC2(c3cc(Br)cs3)CNCC2CS1)c1ccccc1 ; Cl] | ($^{79}$Br/$^{81}$Br) 422/424 (M + H) |

Preparation 103

N-[(4aR,7aR)-7a-Isothiazol-5-yl-4a,5,6,7-tetrahydro-4H-pyrrolo[3,4-d][1,3]thiazin-2-yl]benzamide

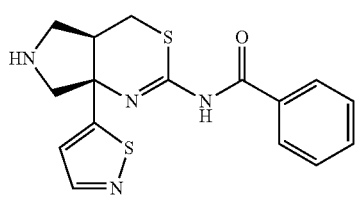 [SMILES: O=C(NC1=N[C@@]2(c3ccns3)CNC[C@H]2CS1)c1ccccc1]

Preparation 104

N-[(4aR,7aR)-7a-(5-Fluorothiophen-2-yl)-4,4a,5,6,7,7a-hexahydropyrrolo[3,4-d][1,3]thiazin-2-yl]benzamide, isomer 2

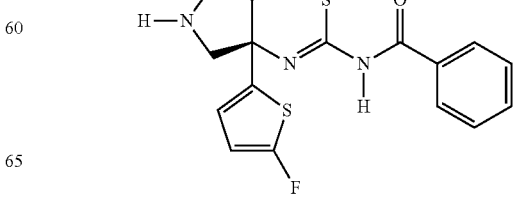

Through a stirred pale yellow solution of N-[(4aR,7aR)-7a-(5-fluorothiophen-2-yl)-6-(prop-2-en-1yl)-4,4a,5,6,7,7a-hexahydropyrrolo[3,4-d][1,3]thiazin-2-yl]benzamide, isomer 2 (1.44 g, 3.59 mmol) in chloroform (36 mL) is passed a stream of nitrogen for 15 minutes. N,N-Dimethylbarbituric acid (3.36 g, 21.5 mmol) is added and degassing is continued for another 5 minutes. Tetrakis(triphenylphosphine)palladium (622 mg, 538 μmol) is added and the mixture is stirred under an atmosphere of nitrogen at ambient temperature for 75 minutes. The mixture is diluted with dichloromethane (~30 mL) and extracted with 1 M hydrochloric acid (2×75 mL). The pH of the combined aqueous acid extracts is adjusted to basic pH with 5 M sodium hydroxide (32 mL). The aqueous solution is extracted with dichloromethane (3×75 mL), and these combined dichloromethane extracts are dried over sodium sulfate, filtered, and concentrated under reduced pressure to give the title compound (1.22 g, 94%) as a pale yellow solid. ES/MS (m/e): 362.0 (M+H).

Preparation 105
Racemic N-[7a-(5-Fluoro-2-thienyl)-4a,5,6,7-tetrahydro-4H-pyrrolo[3,4-d][1,3]thiazin-2-yl]benzamide

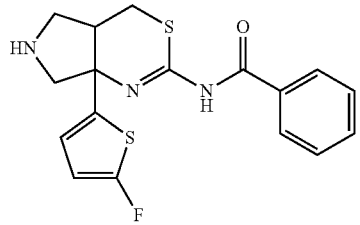 [SMILES: O=C(NC1=NC2(c3ccc(F)s3)CNCC2CS1)c1ccccc1]

Through a stirred solution of racemic N-[6-allyl-7a-(5-fluoro-2-thienyl)-4,4a,5,7-tetrahydropyrrolo[3,4-d][1,3]thiazin-2-yl]benzamide (163 mg, 0.406 mmol) in chloroform (4.1 mL) is passed a stream of nitrogen for 20 minutes. N,N-Dimethylbarbituric acid (380 mg, 2.44 mmol) is added and degassing is continued for a further 5 minutes. Tetrakis(triphenylphosphine)palladium (70 mg, 0.061 mmol) is added and the mixture is stirred under nitrogen at room temperature for 45 minutes. The mixture is diluted with dichloromethane (approximately 15 mL) and extracted twice with 1 M hydrochloric acid (10 mL). The pH of the combined aqueous acid extracts is adjusted with 5 M sodium hydroxide (5 mL). The aqueous solution is extracted three times with dichloromethane (20 mL) and the combined dichloromethane extracts are dried over sodium sulfate, filtered, and concentrated to give the title compound (135 mg, 92%). ES/MS (m/e): 361 (M+H).

The following compounds are prepared essentially by the method of Preparation 105 using the appropriate allyl intermediate.

TABLE 21

| Prep No. | Chemical name | Structure | ES/MS (m/e) |
| --- | --- | --- | --- |
| 106 | N-[(4aR,7aR)-7a-(4-Bromo-2-thienyl)-4a,5,6,7-tetrahydro-4H-pyrrolo[3,4-d][1,3]thiazin-2-yl]benzamide, isomer 2 | 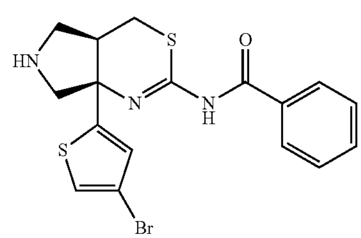 [SMILES: O=C(NC1=N[C@@]2(c3cc(Br)cs3)CNC[C@H]2CS1)c1ccccc1] | ($^{79}$Br/$^{81}$Br) 422/424 (M + H) |
| 107 | Racemic N-(7a-Thiazol-5-yl-4a,5,6,7-tetrahydro-4H-pyrrolo[3,4-d][1,3]thiazin-2-yl)benzamide | 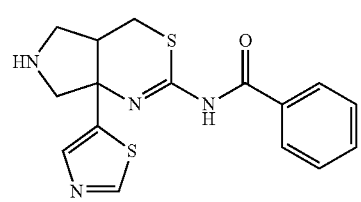 [SMILES: O=C(NC1=NC2(c3cncs3)CNCC2CS1)c1ccccc1] | 345 (M + H) |
| 108 | Racemic N-[7a-(4-Fluorophenyl)-4a,5,6,7-tetrahydro-4H-pyrrolo[3,4-d][1,3]thiazin-2-yl]benzamide | 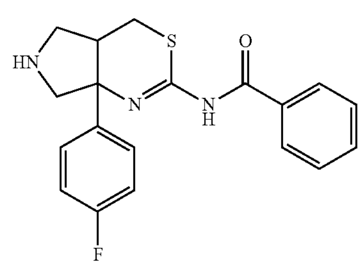 [SMILES: O=C(NC1=NC2(c3ccc(F)cc3)CNCC2CS1)c1ccccc1] | 356 (M + H) |

| Prep No. | Chemical name | Structure | ES/MS (m/e) |
|---|---|---|---|
| 109 | Racemic N-7a-(4-Bromo-2-thienyl)-4a,5,6,7-tetrahydro-4H-pyrrolo[3,4-d][1,3]thiazin-2-yl]benzamide | 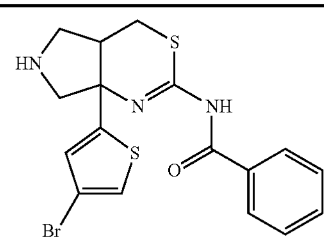 | [79]Br/[81]Br 422/424 (M + H) |

Preparation 110

N-[(4aR,7aS)-7a-Phenyl-4a,5,6,7-tetrahydro-4H-pyrrolo[3,4-d][1,3]thiazin-2-yl]benzamide

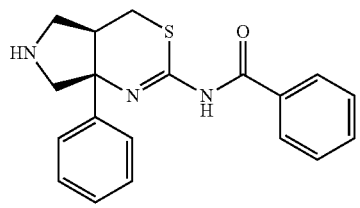 [SMILES: O=C(NC1=N[C@@]2(c3ccccc3)CNC[C@H]2CS1)c1ccccc1]

Iodotrimethylsilane (10 mL, 70 mmol) is added to a solution of benzyl (4aR,7aS)-2-benzamido-7a-phenyl-4,4a,5,7-tetrahydropyrrolo[3,4-d][1,3]thiazine-6-carboxylate (11 g, 23 mmol) in acetonitrile (165 mL), stirred at room temperature for 2 hours and concentrated. The mixture is diluted with water (100 mL) and ethyl acetate (150 mL) and the pH adjusted to 4 with 1 M hydrochloric acid. The aqueous layer is collected. The pH of this aqueous layer is then adjusted to 10 with 2 M sodium hydroxide. The resulting solution is then extracted with ethyl acetate (100 mL), dried over magnesium sulfate and concentrated to give the title compound (31 g, 63%). ES/MS (m/e): 338 (M+H).

Preparation 111

N-[(4aR,7aR)-7a-(5-Cyanothiophen-2-yl)-4,4a,5,6,7,7a-hexahydropyrrolo[3,4-d][1,3]thiazin-2-yl]benzamide

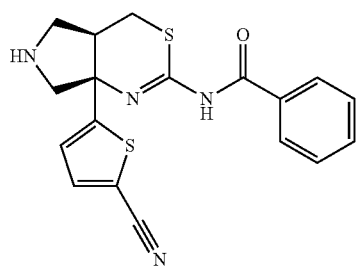 [SMILES: N#Cc1ccc([C@]23CNC[C@H]2CSC(NC(=O)c2ccccc2)=N3)s1]

To a stirred clear and colorless solution of the benzyl (4aR,7aR)-2-(benzoylamino)-7a-(5-cyanothiophen-2-yl)-4a,5,7,7a-tetrahydropyrrolo[3,4-d][1,3]thiazine-6(4H)-carboxylate (405 mg, 0.806 mmol) in acetonitrile (16 mL) under an atmosphere of nitrogen at room temperature is added iodotrimethylsilane (345 µL, 2.42 µmol). The resulting pale yellow solution is stirred at room temperature for 70 minutes. Methanol (391 µL, 9.67 mmol) is added and the pale yellow mixture is stirred for 5 minutes, and then concentrated under reduced pressure. The residue is partially purified by silica gel chromatography, eluting with a dichloromethane/methanol, gradient from 99:1 to 90:10, to give the title compound (349 mg, 118%) as a pale yellow solid (assume quantitative recovery and carry partially purified material into next step). MS/ES (m/z) 369.0 (M+H).

Preparation 112

N-[(4aR,7aR)-7a-(2-Thienyl)-4a,5,6,7-tetrahydro-4H-pyrrolo[3,4-d][1,3]thiazin-2-yl]benzamide

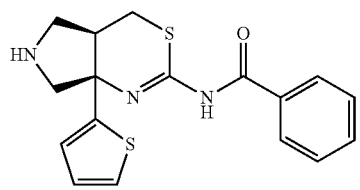 [SMILES: O=C(NC1=N[C@@]2(c3cccs3)CNC[C@H]2CS1)c1ccccc1]

A solution of benzyl (4aR,7aR)-2-benzamido-7a-(2-thienyl)-4,4a,5,7-tetrahydropyrrolo[3,4-d][1,3]thiazine-6-carboxylate (14 g, 29.3 mmol) in acetonitrile (210 mL) is treated with iodotrimethylsilane (7.53 mL, 52.7 mmol) at room temperature. The solution is stirred for 1 hour and the solvent is evaporated. The residue is quenched with 1 M hydrochloric acid and ethyl acetate and the resulting mixture is filtered through diatomaceous earth. The aqueous layer is separated, neutralized with 50% w/w aqueous solution of sodium hydroxide and extracted with ethyl acetate. The organic extracts are dried over sodium sulfate and concentrated to give the title compound (7.9 g, 78%). ES/MS (m/e): 344 (M+H).

The following compound is prepared essentially as described for Preparation 112 using the appropriate carboxybenzyl protected intermediate.

TABLE 22

| Prep. No. | Chemical name | Structure | ES/MS (m/e) |
|---|---|---|---|
| 113 | Racemic N-(7a-Thiazol-5-yl-4a,5,6,7-tetrahydro-4H-pyrrolo[3,4-d][1,3]thiazin-2-yl)benzamide | 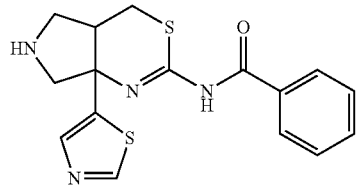 [SMILES: O=C(NC1=NC2(c3cncs3)CNCC2CS1)c1ccccc1] | 345 (M + H) |

Preparation 114

Racemic N-[7a-(3-Bromophenyl)-6-(5-fluoropyrimidin-2-yl)-4,4a,5,7-tetrahydropyrrolo[3,4-d][1,3]thiazin-2-yl]benzamide

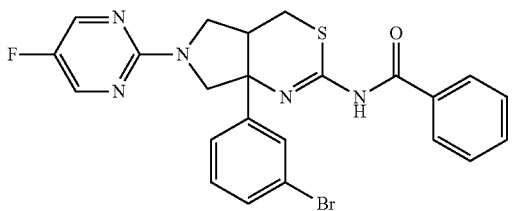 [SMILES: O=C(NC1=NC2(c3cccc(Br)c3)CN(c3ncc(F)cn3)CC2CS1)c1ccccc1]

To a solution of racemic benzyl 2-benzamido-7a-(3-bromophenyl)-4,4a,5,7-tetrahydropyrrolo[3,4-d][1,3]thiazine-6-carboxylate (1.6 g, 2.9 mmol) in acetonitrile (60 mL) is added iodotrimethylsilane (1.3 mL, 9.1 mmol). The resultant solution is stirred at ambient temperature for 3 hours and concentrated to dryness. The residue is purified by ion exchange chromatography (first elute with MeOH/CH$_2$Cl$_2$ (¼, 50 mL), followed by 7 N NH$_3$ in MeOH/CH$_2$Cl$_2$ (¼, 50 mL)) to give after evaporation of the solvent 1.7 g of intermediate, N-[7a-(3-bromophenyl)-4a,5,6,7-tetrahydro-4H-pyrrolo[3,4-d][1,3]thiazin-2-yl]benzamide. This is then dissolved in 1,4-dioxane (30 mL) and diisopropylethylamine (2.0 mL, 11 mmol) and 5-fluoro-2-chloropyrimidine (850 μL, 8.90 mmol) are added sequentially. The resulting solution is heated at 110° C. for 1 hour before additional diisopropylethylamine (1.0 mL, 5.7 mmol) is added and heating is continued for another 17 hours before it is cooled to room temperature and concentrated to dryness. The residue is purified by silica gel flash chromatography, eluting with gradient of ethyl acetate/dichloromethane (0% to 30%) to give the title compound (1.1 g, 73%). ES/MS (m/z): ($^{79}$Br/$^{81}$Br) 512/514 (M+H).

Preparation 115

N-[(4aR,7aS)-6-(5-Fluoropyrimidin-2-yl)-7a-phenyl-4,4a,5,7-tetrahydropyrrolo[3,4-d][1,3]thiazin-2-yl]benzamide

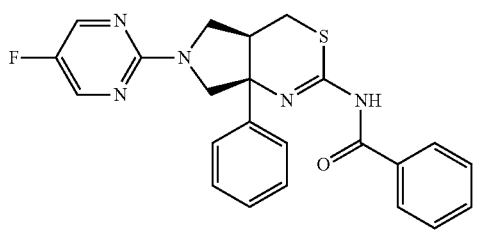 [SMILES: O=C(NC1=N[C@@]2(c3ccccc3)CN(c3ncc(F)cn3)C[C@H]2CS1)c1ccccc1]

A solution of N-[(4aR,7aS)-7a-phenyl-4a,5,6,7-tetrahydro-4H-pyrrolo[3,4-d][1,3]thiazin-2-yl]benzamide (250 mg, 0.629 mmol), 5-fluoro-2-chloropyrimidine (167 mg, 1.26 mmol), 1,4-dioxane (10 mL), and triethylamine (318 mg, 3.14 mmol) is stirred at 110° C. for 4 hours. The reaction is cooled, diluted with water and extracted with dichloromethane. The organic layers are combined, dried, filtered, and concentrated under reduced pressure to give a residue. The residue is purified by silica gel flash chromatography, eluting with hexane/ethyl acetate (1:0) to hexane/ethyl acetate (0:1) to give the title compound (0.217 g, 80%). ES/MS (m/e): 434 (M+H).

Preparation 116

N-[(4aR,7aS)-6-(5-Fluoro-4-isopropyl-pyrimidin-2-yl)-7a-phenyl-4,4a,5,7-tetrahydropyrrolo[3,4-d][1,3]thiazin-2-yl]benzamide

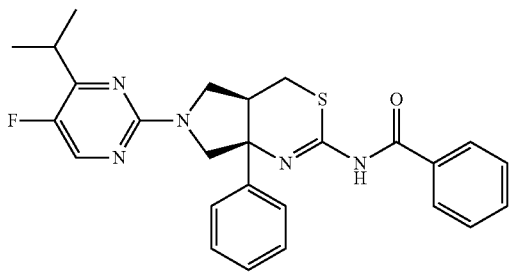 [SMILES: CC(C)c1nc(N2C[C@H]3CSC(NC(=O)c4ccccc4)=N[C@@]3(c3ccccc3)C2)ncc1F]

A solution of N-[(4aR,7aS)-7a-phenyl-4a,5,6,7-tetrahydro-4H-pyrrolo[3,4-d][1,3]thiazin-2-yl]benzamide hydrochloride (285 mg, 7.62 μmol), diisopropylethylamine (798 μL, 4.57 mmol) and 2-chloro-5-fluoro-4-isopropyl-pyrimidine (0.798 g, 4.57 mmol) in 1,4-dioxane (15 mL) is heated to 100° C. for eight hours under nitrogen. The reaction mixture is cooled and diluted with water and aqueous saturated sodium bicarbonate. The mixture is extracted with ethyl acetate (3×). The combined organic layers are dried over sodium sulfate and the solvent is removed under vacuum. The crude product is purified over silica gel eluting with a 5% to 100% ethyl acetate in hexanes gradient, to give the title compound (112 mg, 31%). ES/MS (m/e): 476 (M+H).

Preparation 117

N-[(4aR,7aS)-6-(5-Fluoropyrimidin-2-yl)-7a-phenyl-4,4a,5,7-tetrahydropyrrolo[3,4-d][1,3]thiazin-2-yl]benzamide

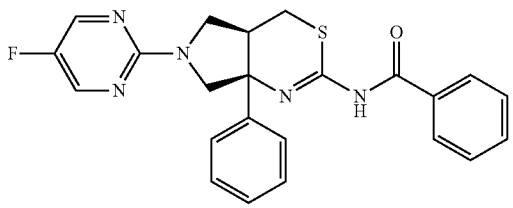 [SMILES: O=C(NC1=N[C@@]2(c3ccccc3)CN(c3ncc(F)cn3)C[C@H]2CS1)c1ccccc1]

N,N,N',N'-tetramethylguanidine (3.4 mL, 27 mmol) is added to a solution of N-[(4aR,7aS)-7a-phenyl-4a,5,6,7-tetrahydro-4H-pyrrolo[3,4-d][1,3]thiazin-2-yl]benzamide (7.5 g, 22 mmol) and 5-fluoro-2-chloropyrimidine (3.5 g, 27 mmol) in dimethylsulfoxide (75 mL). The reaction is stirred at 100° C. for 2 hours, cooled to room temperature and water is added (225 mL). The precipitated product is isolated by filtration and is dried in a vacuum oven at 45° C. to give the title compound (9.5 g, 99%). ES/MS (m/e): 434 (M+H).

Preparation 118

N-[7a-(2-Fluorophenyl)-6-(5-fluoropyrimidin-2-yl)-4,4a,5,7-tetrahydropyrrolo[3,4-d][1,3]thiazin-2-yl]benzamide

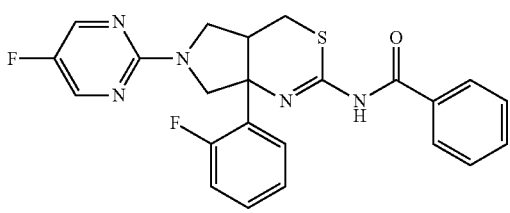 [SMILES: O=C(NC1=NC2(c3ccccc3F)CN(c3ncc(F)cn3)CC2CS1)c1ccccc1]

N,N,N',N'-tetramethylguanidine (0.44 mL, 3.5 mmol) is added to a solution of racemic N-[7a-(2-fluorophenyl)-4a,5,6,7-tetrahydro-4H-pyrrolo[3,4-d][1,3]thiazin-2-yl]benzamide (1.0 g, 2.9 mmol) and 5-fluoro-2-chloropyrimidine (0.46 g, 3.5 mmol) in dimethylsulfoxide (10 mL). The reaction is stirred at 100° C. for 2 hours, and cooled to room temperature. To the crude reaction is added ethyl acetate (7.5 ml) and water (2.5 ml), the mixture is passed through diatomaceous earth (10 g), and the solvent removed under reduced pressure. The residue is purified by silica gel chromatography eluting with a gradient of 40% to 60% ethyl acetate in hexanes to give the title compound (560 mg, 43%). ES/MS (m/e): 452 (M+H).

Preparation 119

N-[(4aR,7aR)-7a-(5-Fluorothiophen-2-yl)-6-(pyrimidin-2-yl)-4,4a,5,6,7,7a-hexahydropyrrolo[3,4-d][1,3]thiazin-2-yl]benzamide, isomer 2

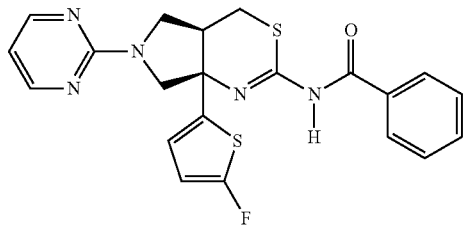 [SMILES: O=C(NC1=N[C@@]2(c3ccc(F)s3)CN(c3ncccn3)C[C@H]2CS1)c1ccccc1]

To a stirred mixture of the N-[(4aR,7aR)-7a-(5-fluorothiophen-2-yl)-4,4a,5,6,7,7a-hexahydropyrrolo[3,4-d][1,3]thiazin-2-yl]benzamide, isomer 2 (411 mg, 1.14 mmol) in 1,4-dioxane (23 mL) is added diisopropylethylamine (595 µL, 3.41 mmol) and 2-chloropyrimidine (1.30 g, 11.4 mmol). The mixture is heated at reflux for 2.5 hours. The solution is allowed to cool, diluted with ethyl acetate (120 mL) and washed with dilute aqueous sodium bicarbonate (100 mL, prepared from 50 mL saturated aqueous sodium bicarbonate and 50 mL water), water (50 mL), and brine (50 mL). The organic phase is dried over sodium sulfate, filtered, and concentrated under reduced pressure. The residue is purified by silica gel chromatography eluting with hexanes/ethyl acetate, gradient from 60:40 to 0:100, to give the title compound (465 mg, 93%) as a white foam. ES/MS (m/e): 440.2 (M+H).

Preparation 120

N-[(4aR,7aR)-6-(5-Fluoropyrimidin-2-yl)7a-(5-fluorothiophen-2-yl)-4,4a,5,6,7,7a-hexahydropyrrolo[3,4-d][1,3]thiazin-2-yl]benzamide

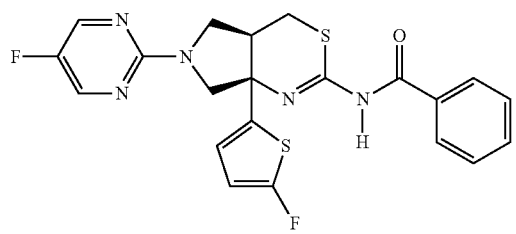 [SMILES: O=C(NC1=N[C@@]2(c3ccc(F)s3)CN(c3ncc(F)cn3)C[C@H]2CS1)c1ccccc1]

To a stirred mixture of the N-[(4aR,7aR)-7a-(5-fluorothiophen-2-yl)-4,4a,5,6,7,7a-hexahydropyrrolo[3,4-d][1,3]thiazin-2-yl]benzamide (415 mg, 1.15 mmol) in 1,4-dioxane (23 mL) is added diisopropylethylamine (601 µL, 3.44 mmol) and 2-chloro-5-fluoropyrimidine (1.10 mL, 11.5 mmol). The solution is heated to reflux for 3 hours. The pale yellow solution is allowed to cool, diluted with ethyl acetate, (120 mL) and washed with dilute aqueous sodium bicarbonate (100 mL, prepared from 50 mL saturated sodium bicarbonate and 50 mL water), water (50 mL), and brine (50 mL). The organic phase is dried over sodium sulfate, filtered, and concentrated under reduced pressure. The residue is purified by silica gel chromatography eluting with hexanes/ethyl acetate, gradient from 60:40 to 30:70, to give the title compound (435 mg, 83%) as a white foam. ES/MS (m/e): 458.0 (M+H).

Preparation 121

N-[7a-(5-Fluoro-2-thienyl)-6-pyrimidin-2-yl-4,4a,5,7-tetrahydropyrrolo[3,4-d][1,3]thiazin-2-yl]benzamide

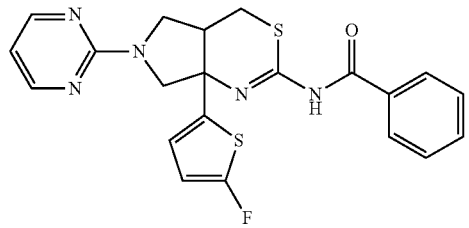 [SMILES: O=C(NC1=NC2(c3ccc(F)s3)CN(c3ncccn3)CC2CS1)c1ccccc1]

To a stirred mixture of N-[7a-(5-fluoro-2-thienyl)-4a,5,6,7-tetrahydro-4H-pyrrolo[3,4-d][1,3]thiazin-2-yl]benzamide (127 mg, 0.351 mmol) in 1,4-dioxane (7.0 mL) is added diisopropylethylamine (0.184 mL, 1.05 mmol) and 2-chloropyrimidine (402 mg, 3.51 mmol). The solution is heated to reflux for 2 hours then is cooled, diluted with ethyl acetate, (60 mL) and washed with dilute sodium bicarbonate (30 mL, prepared from saturated sodium bicarbonate (15 mL) and water (15 mL), water (30 mL) and brine (30 mL). The organic phase is dried over sodium sulfate, filtered, and concentrated. The residue is purified by silica gel chromatography eluting with dichloromethane/methanol (gradient from 99:1 to 96:4) to give after concentration a residue which is further purified by silica gel chromatography eluting with hexanes/ethyl acetate (gradient from 60:40 to 30:70) to give the title compound (107 mg, 69%). ES/MS (m/e): 440 (M+H).

Preparation 122

N-{(4aR,7aR)-7a-(5-Cyanothiophen-2-yl)-6-[5-fluoro-4-(2-hydroxypropan-2-yl)pyrimidin-2-yl]-4,4a,5,6,7,7a-hexahydropyrrolo[3,4-d][1,3]thiazin-2-yl}benzamide

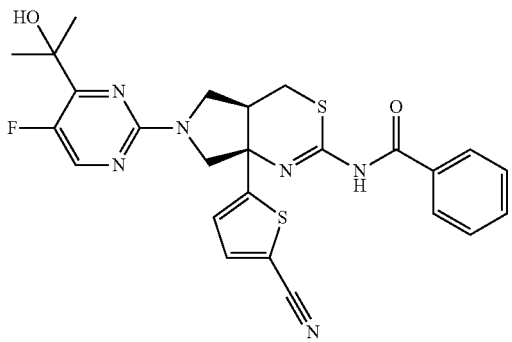 [SMILES: CC(C)(O)c1nc(N2C[C@H]3CSC(NC(=O)c4ccccc4)=N[C@@]3(c3ccc(C#N)s3)C2)ncc1F]

To a stirred clear and colorless solution of N-[(4aR,7aR)-7a-(5-cyanothiophen-2-yl)-4,4a,5,6,7,7a-hexahydropyrrolo[3,4-d][1,3]thiazin-2-yl]benzamide (0.806 mmol) in 1,4-dioxane (16 mL) is added diisopropylethylamine (422 µL, 2.42 mmol) and 2-(2-chloro-5-fluoropyrimidin-4-yl)propan-2-ol (1.54 g, 8.06 mmol). The solution is heated to reflux for 14 hours. The pale yellow solution is allowed to cool, diluted with ethyl acetate (80 mL) and hexanes (20 mL), and washed with dilute aqueous sodium bicarbonate (30 mL, prepared from saturated aqueous sodium bicarbonate (15 mL) and water (15 mL), water (2×20 mL), and brine (20 mL). The organic phase is dried over sodium sulfate, filtered, and concentrated under reduced pressure. The residue is purified by silica gel chromatography, eluting with a hexanes/diethyl ether, gradient from 80:20 to 0:100, to give the title compound (374 mg, 89% over two steps) as a pale yellow glass. MS/ES (m/z) 523.2 (M+H).

Preparation 123

N-[(4aR,7aR)-6-(5-Fluoropyrimidin-2-yl)-7a-(2-thienyl)-4,4a,5,7-tetrahydropyrrolo[3,4-d][1,3]thiazin-2-yl]benzamide

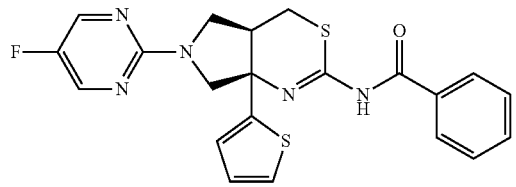 [SMILES: O=C(NC1=N[C@@]2(c3cccs3)CN(c3ncc(F)cn3)C[C@H]2CS1)c1ccccc1]

A solution of N-[(4aR,7aR)-7a-(2-thienyl)-4a,5,6,7-tetrahydro-4H-pyrrolo[3,4-d][1,3]thiazin-2-yl]benzamide (7.7 g, 22.4) and N,N,N',N'-tetramethylguanidine (3.39 mL, 26.9 mmol) in dimethyl sulfoxide (61 mL) is treated with 5-fluoro-2-chloropyrimidine (2.25 mL, 23.54 mmol) and the resulting solution is heated at 50° C. for 4 hours. The solution is cooled to room temperature and added to water (500 mL). The crude product is purified over silica gel using a 5 to 50% gradient of ethyl acetate/hexanes to give the title compound (7 g, 71%). ES/MS (m/e): 440 (M+H).

Alternate Preparation 123

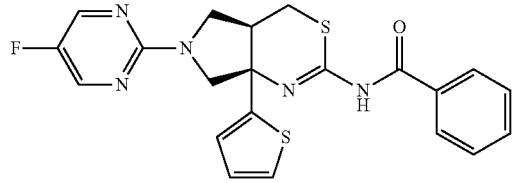 [SMILES: O=C(NC1=N[C@@]2(c3cccs3)CN(c3ncc(F)cn3)C[C@H]2CS1)c1ccccc1]

A solution of N-[(4aR,7aR)-7a-(2-thienyl)-4a,5,6,7-tetrahydro-4H-pyrrolo[3,4-d][1,3]thiazin-2-yl]benzamide hydrochloride (600 mg, 1.58 mmol), 5-fluoro-2-chloropyrimidine (418 mg, 3.16 mmol), 1,4-dioxane (30 mL), and triethylamine (799 mg, 7.90 mmol) is stirred at 110° C. for 4 hours. The reaction is cooled, diluted with water, and extracted with dichloromethane. The organic layers are combined, dried, filtered, and concentrated to give a residue. The residue is purified by silica gel flash chromatography, eluting with hexane/ethyl acetate (1:0) to hexane/ethyl acetate (0:1) to give the title compound (0.65 g, 98%). ES/MS (m/e): 440 (M+H).

The following compounds are prepared essentially by the Alternate method of Preparation 123 using 2-10 equivalents of the appropriate substituted-2-chloropyrimidines with triethylamine or diisopropylethylamine as the base. Heating varies from 3-24 hrs.

TABLE 23

| Prep. No. | Chemical name | Structure | ES/MS (m/e) (M + H) |
|---|---|---|---|
| 124 | N-[(4aR,7aS)-7a-Phenyl-6-pyrimidin-2-yl-4,4a,5,7-tetrahydropyrrolo[3,4-d][1,3]thiazin-2-yl]benzamide | 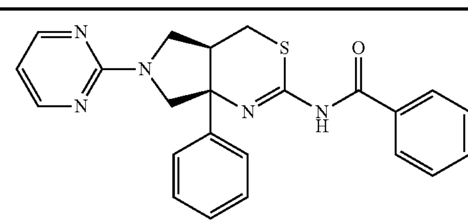 | 416 |

TABLE 23-continued

| Prep. No. | Chemical name | Structure | ES/MS (m/e) (M + H) |
|---|---|---|---|
| 125 | Racemic N-[7a-(4-Fluorophenyl)-6-(5-fluoropyrimidin-2-yl)-4,4a,5,7-tetrahydropyrrolo[3,4-d][1,3]thiazin-2-yl]benzamide | 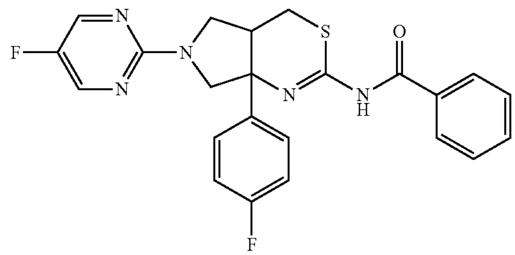 [SMILES: O=C(NC1=NC2(c3ccc(F)cc3)CN(c3ncc(F)cn3)CC2CS1)c1ccccc1] | 452 |
| 126 | N-[(4aR,7aR)-6-(4-Isopropylpyrimidin-2-yl)-7a-(2-thienyl)-4,4a,5,7-tetrahydropyrrolo[3,4-d][1,3]thiazin-2-yl]benzamide | 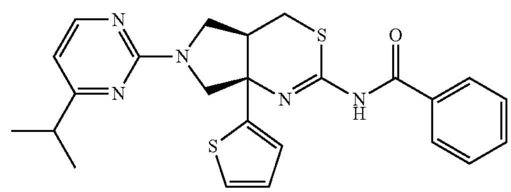 [SMILES: CC(C)c1ccnc(N2C[C@H]3CSC(NC(=O)c4ccccc4)=N[C@@]3(c3cccs3)C2)n1] | 464 |
| 127 | N-[(4aR,7aR)-6-(4-Cyclopropylpyrimidin-2-yl)-7a-(2-thienyl)-4,4a,5,7-tetrahydropyrrolo[3,4-d][1,3]thiazin-2-yl]benzamide-isomer 1 | 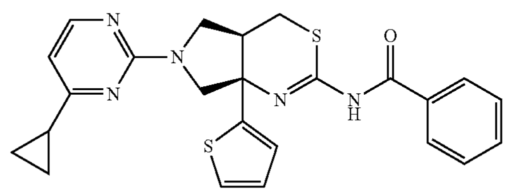 [SMILES: O=C(NC1=N[C@@]2(c3cccs3)CN(c3nccc(C4CC4)n3)C[C@H]2CS1)c1ccccc1] | 462 |
| 128 | N-[(4aR,7aR)-7a-(4-Bromo-2-thienyl)-6-pyrimidin-2-yl-4,4a,5,7-tetrahydropyrrolo[3,4-d][1,3]thiazin-2-yl]benzamide, isomer 2 | 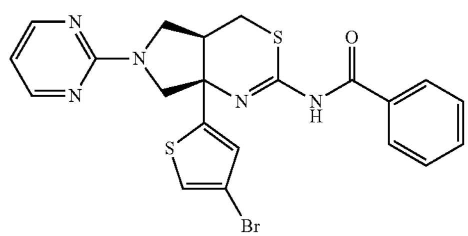 [SMILES: O=C(NC1=N[C@@]2(c3cc(Br)cs3)CN(c3ncccn3)C[C@H]2CS1)c1ccccc1] | ($^{79}$Br/$^{81}$Br) 500/502 |
| 129 | Racemic N-[6-(4-Cyclopropylpyrimidin-2-yl)-7a-thiazol-5-yl-4,4a,5,7-tetrahydropyrrolo[3,4-d][1,3]thiazin-2-yl]benzamide | 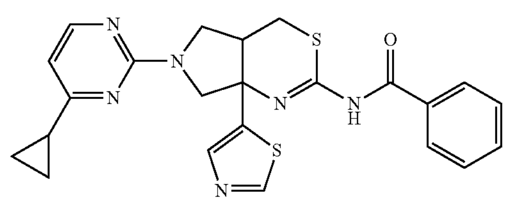 [SMILES: O=C(NC1=NC2(c3cncs3)CN(c3nccc(C4CC4)n3)CC2CS1)c1ccccc1] | 463 |
| 130 | Racemic N-[6-(5-Fluoropyrimidin-2-yl)-7a-thiazol-5-yl-4,4a,5,7-tetrahydropyrrolo[3,4-d][1,3]thiazin-2-yl]benzamide | 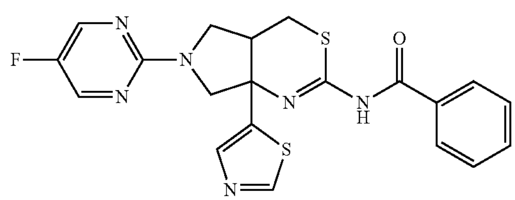 [SMILES: O=C(NC1=NC2(c3cncs3)CN(c3ncc(F)cn3)CC2CS1)c1ccccc1] | 441 |
| 131 | Racemic N-(6-Pyrimidin-2-yl-7a-thiazol-5-yl-4,4a,5,7-tetrahydropyrrolo[3,4-d][1,3]thiazin-2-yl)benzamide | 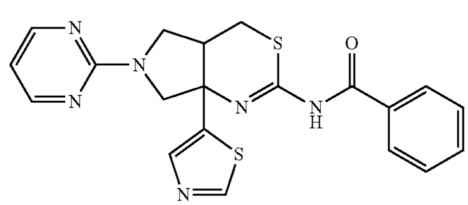 [SMILES: O=C(NC1=NC2(c3cncs3)CN(c3ncccn3)CC2CS1)c1ccccc1] | 423 |

TABLE 23-continued

| Prep. No. | Chemical name | Structure | ES/MS (m/e) (M + H) |
|---|---|---|---|
| 132 | Racemic N-[6-(4-Isopropylpyrimidin-2-yl)-7a-thiazol-5-yl-4,4a,5,7-tetrahydropyrrolo[3,4-d][1,3]thiazin-2-yl]benzamide | 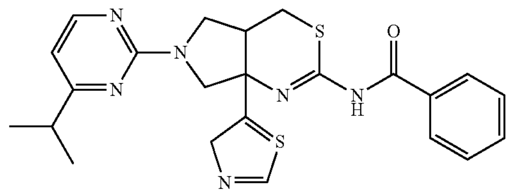 | 465 |
| 133 | N-[(4aR,7aR)-6-(5-Fluoro-4-isopropyl-pyrimidin-2-yl)-7a-thiazol-5-yl-4,4a,5,7-tetrahydropyrrolo[3,4-d][1,3]thiazin-2-yl]benzamide- | 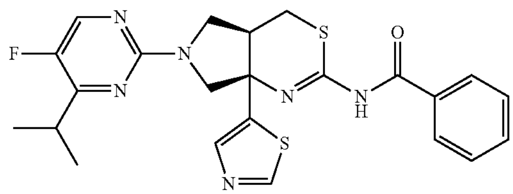 [SMILES: CC(C)c1nc(N2C[C@H]3CSC(NC(=O)c4ccccc4)=N[C@@]3(c3cncs3)C2)ncc1F] | 483 |
| 134 | Racemic N-7a-(4-Bromo-2-thienyl)-6-pyrimidin-2-yl-4,4a,5,7-tetrahydropyrrolo[3,4-d][1,3]thiazin-2-yl]benzamide[a] | 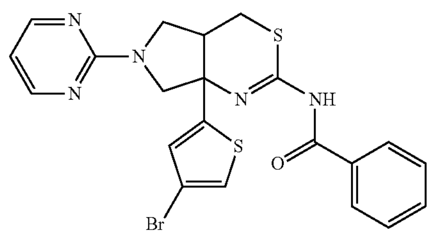 [SMILES: O=C(NC1=NC2(c3cc(Br)cs3)CN(c3ncccn3)CC2CS1)c1ccccc1] | ($^{79}$Br/$^{81}$Br) 500/502 |
| 135 | N-[(4aR,7aR)-6-(5-Fluoropyrimidin-2-yl)-7a-isothiazol-5-yl-4,4a,5,7-tetrahydropyrrolo[3,4-d][1,3]thiazin-2-yl]benzamide | 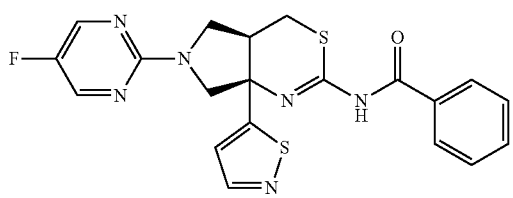 [SMILES: O=C(NC1=N[C@@]2(c3ccns3)CN(c3ncc(F)cn3)C[C@H]2CS1)c1ccccc1] | 441 |
| 136 | N-[(4aR,7aR)-6-[5-Fluoro-4-(1-fluoro-1-methyl-ethyl)pyrimidin-2-yl]-7a-isothiazol-5-yl-4,4a,5,7-tetrahydropyrrolo[3,4-d][1,3]thiazin-2-yl]benzamide, isomer 2 | 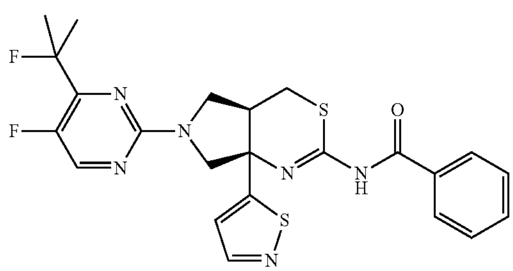 [SMILES: CC(C)(F)c1nc(N2C[C@H]3CSC(NC(=O)c4ccccc4)=N[C@@]3(c3ccns3)C2)ncc1F] | 501 |
| 137 | N-[(4aR,7aR)-6-[5-Fluoro-4-(1-hydroxy-1-methyl-ethyl)pyrimidin-2-yl]-7a-isothiazol-5-yl-4,4a,5,7-tetrahydropyrrolo[3,4-d][1,3]thiazin-2-yl]benzamide, isomer 2 | 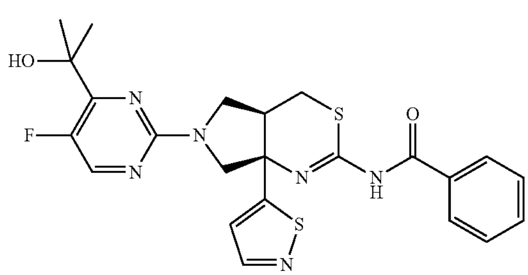 [SMILES: CC(C)(O)c1nc(N2C[C@H]3CSC(NC(=O)c4ccccc4)=N[C@@]3(c3ccns3)C2)ncc1F] | 499 |

TABLE 23-continued

| Prep. No. | Chemical name | ES/MS (m/e) (M + H) |
|---|---|---|
| 138 | N-[(4aR,7aR)-6-[5-Fluoro-4-(1-fluoro-1-methyl-ethyl)pyrimidin-2-yl]-7a-thiazol-5-yl-4,4a,5,7-tetrahydropyrrolo[3,4-d][1,3]thiazin-2-yl]benzamide | 501 |
| 139 | N-[(4aR,7aS)-6-[5-Fluoro-4-(1-fluoro-1-methyl-ethyl)pyrimidin-2-yl]-7a-phenyl-4,4a,5,7-tetrahydropyrrolo[3,4-d][1,3]thiazin-2-yl]benzamide | 494 |
| 140 | N-[(4aR,7aR)-6-[5-Fluoro-4-(1-hydroxy-1-methyl-ethyl)pyrimidin-2-yl]-7a-thiazol-5-yl-4,4a,5,7-tetrahydropyrrolo[3,4-d][1,3]thiazin-2-yl]benzamide | 499 |
| 141 | N-[(4aR,7aS)-6-(4-Ethyl-5-fluoro-pyrimidin-2-yl)-7a-phenyl-4,4a,5,7-tetrahydropyrrolo[3,4-d][1,3]thiazin-2-yl]benzamide | 462 |
| 142 | N-[(4aR,7aS)-6-[5-Fluoro-4-(hydroxymethyl)pyrimidin-2-yl]-7a-phenyl-4,4a,5,7-tetrahydropyrrolo[3,4-d][1,3]thiazin-2-yl]benzamide | 464 |

TABLE 23-continued

| Prep. No. | Chemical name | Structure | ES/MS (m/e) (M + H) |
|---|---|---|---|
| 143 | N-[(4aR,7aS)-6-[5-Fluoro-4-(1-hydroxy-1-methyl-ethyl)pyrimidin-2-yl]-7a-phenyl-4,4a,5,7-tetrahydropyrrolo[3,4-d][1,3]thiazin-2-yl]benzamide | 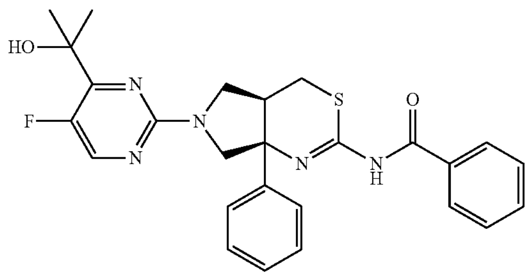 [SMILES: CC(C)(O)c1nc(N2C[C@H]3CSC(NC(=O)c4ccccc4)=N[C@@]3(c3ccccc3)C2)ncc1F] | 492 |
| 144 | N-[(4aR,7aR)-7a-(5-Cyanothiophen-2-yl)-6-(5-fluoropyrimidin-2-yl)-4,4a,5,6,7,7a-hexahydropyrrolo[3,4-d][1,3]thiazin-2-yl]benzamide | 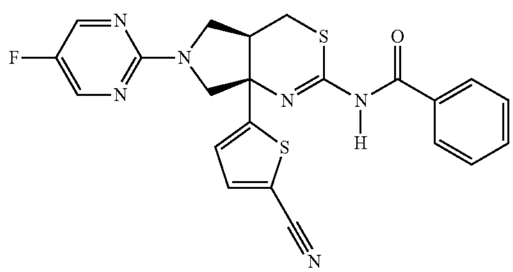 [SMILES: N#Cc1ccc([C@]23CN(c4ncc(F)cn4)C[C@H]2CSC(NC(=O)c2ccccc2)=N3)s1] | 465.2 |
| 145 | N-[(4aR,7aS)-6-(5-Fluoro-4-methoxy-6-methyl-pyrimidin-2-yl)-7a-phenyl-4,4a,5,7-tetrahydropyrrolo[3,4-d][1,3]thiazin-2-yl]benzamide | 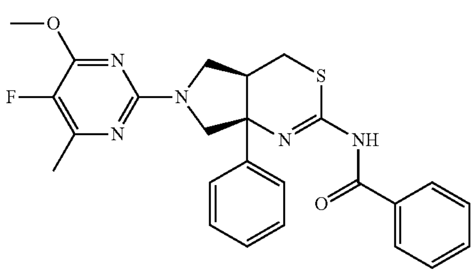 [SMILES: COc1nc(N2C[C@H]3CSC(NC(=O)c4ccccc4)=N[C@@]3(c3ccccc3)C2)nc(C)c1F] | 478 |
| 146 | Racemic N-[7a-(4-Bromo-2-thienyl)-6-(5-fluoropyrimidin-2-yl)-4,4a,5,7-tetrahydropyrrolo[3,4-d][1,3]thiazin-2-yl]benzamide | 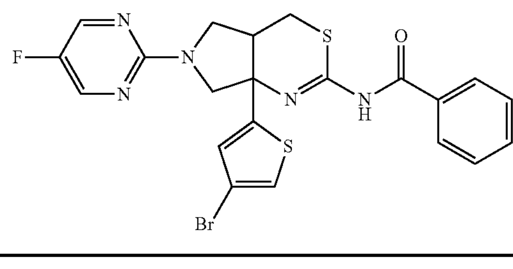 | ($^{79}$Br/$^{81}$Br) 462/464 |

$^a$The reaction mixture is extracted with 3:1 chloroform:isopropyl alcohol instead of DCM.

Preparation 147

N-[(4aR,7aR)-6-(Pyrimidin-2-yl-7a-(2-thienphen-2-yl)-4,4a,5,6,7,7a-hexahydropyrrolo[3,4-d][1,3]thiazin-2-yl]benzamide

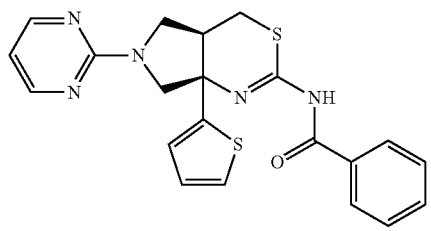 [SMILES: O=C(NC1=N[C@@]2(c3cccs3)CN(c3ncccn3)C[C@H]2CS1)c1ccccc1]

A slurry of N-[(4aR,7aR)-7a-(4-bromo-2-thienyl)-6-pyrimidin-2-yl-4,4a,5,7-tetrahydropyrrolo[3,4-d][1,3]thiazin-2-yl]benzamide (775 mg, 1.55 mmol), 10% Pd/C (1.65 g, 1.6 mmol), ammonium formate (0.977 g, 15.5 mmol), and ethanol (31 ml) in a sealed screw cap vial is stirred at 40° C. for 1 hour. To the reaction is added diatomaceous earth, saturated sodium bicarbonate (1 mL), and ethyl acetate. The biphasic slurry is filtered through diatomaceous earth, and the pad is washed with ethyl acetate. The filtrate is extracted with ethyl acetate. The organic layers are combined, dried, filtered, and concentrated to give the title compound (0.57 g, 87%). ES/MS (m/e): 422 (M+H).

Preparation 148

Racemic N-[6-Pyrimidin-2-yl-7a-(2-thienyl)-4,4a,5,7-tetrahydropyrrolo[3,4-d][1,3]thiazin-2-yl]benzamide

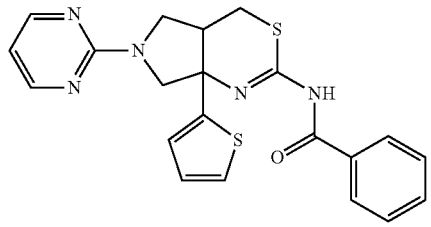 [SMILES: O=C(NC1=NC2(c3cccs3)CN(c3ncccn3)CC2CS1)c1ccccc1]

A slurry of racemic N-7a-(4-bromo-2-thienyl)-6-pyrimidin-2-yl-4,4a,5,7-tetrahydropyrrolo[3,4-d][1,3]thiazin-2-yl]benzamide (40 mg, 0.0799 mmol), 10% Pd/C (85.06 mg, 0.0799 mmol), ammonium acetate (61.61 mg, 0.799 mmol), and ethanol (2 ml) in a sealed vessel is stirred at room temperature overnight. The reaction is diluted with ethanol, filtered through diatomaceous earth, and washed with 2 N ammonia in methanol (80 mL). The solution is concentrated, diluted with saturated sodium bicarbonate, and extracted with ethyl acetate (3×). The organic layers are combined, dried over sodium sulfate, filtered, and concentrated to give the title compound (20 mg, 59%). ES/MS (m/e): 422 (M+H).

Preparation 149

Racemic N-[7a-(3-Cyanophenyl)-6-(5-fluoropyrimidin-2-yl)-4,4a,5,7-tetrahydropyrrolo[3,4-d][1,3]thiazin-2-yl]benzamide

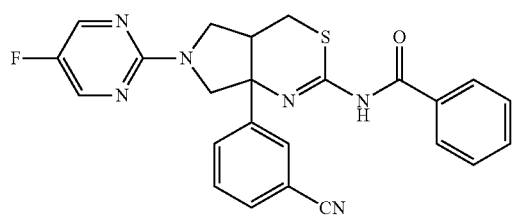 [SMILES: N#Cc1cccc(C23CN(c4ncc(F)cn4)CC2CSC(NC(=O)c2ccccc2)=N3)c1]

To a solution of racemic N-[7a-(3-bromophenyl)-6-(5-fluoropyrimidin-2-yl)-4,4a,5,7-tetrahydropyrrolo[3,4-d][1,3]thiazin-2-yl]benzamide (310 mg, 605 μmol) and zinc cyanide (170 mg, 1.42 mmol) in dimethylformamide (6.0 mL) is added tetrakis (triphenylphosphine) palladium (200 mg, 171 μmol). The resulting mixture is heated at 100° C. under $N_2$ for 16.5 hours before being cooled to room temperature, filtered through diatomaceous earth, and washed with ethyl acetate (30 mL). The combined filtrate is washed with semi-saturated sodium bicarbonate solution (50 mL), extracted with ethyl acetate (30 mL), and chloroform (30 mL). The combined organic layers are dried over magnesium sulfate, filtered, and concentrated to dryness. The residue is purified by silica gel flash chromatography, eluting with a gradient of ethyl acetate/dichloromethane (0 to 30%) to give the title compound (187 mg, 67%). EI/MS (m/e): 459.0 (M+H).

The following compound is prepared essentially by the method of Preparation 149.

TABLE 24

| Prep. No. | Chemical name | Structure | ES/MS (m/e) (M + H) |
|---|---|---|---|
| 150 | Racemic N-[7a-(4-Cyano-2-thienyl)-6-(5-fluoropyrimidin-2-yl)-4,4a,5,7-tetrahydropyrrolo[3,4-d][1,3]thiazin-2-yl]benzamide | 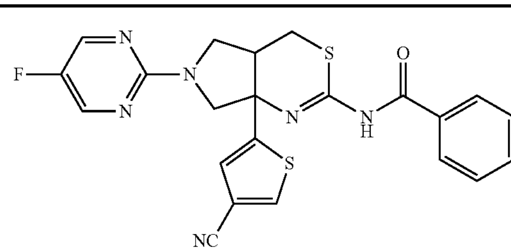 | 465 |

Preparation 151

N-[(4aR,7aR)-6-[5-Fluoro-4-(1-hydroxy-1-methyl-ethyl)-6-methyl-pyrimidin-2-yl]-7a-isothiazol-5-yl-4,4a,5,7-tetrahydropyrrolo[3,4-d][1,3]thiazin-2-yl]benzamide

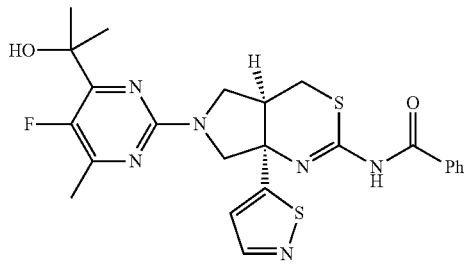 [SMILES: Cc1nc(N2C[C@H]3CSC(NC(=O)c4ccccc4)=N[C@@]3(c3ccns3)C2)nc(C(C)(C)O)c1F]

2-(2-Chloro-5-fluoro-6-methyl-pyrimidin-4-yl)propan-2-ol (104 mg, 0.51 mmol) is dissolved in 1,4-dioxane (3 mL). N-[(4aR,7aR)-7a-Isothiazol-5-yl-4a,5,6,7-tetrahydro-4H-pyrrolo[3,4-d][1,3]thiazin-2-yl]benzamide (125 mg, 0.36 mmol) is added followed by diisopropylethylamine (158 µL, 0.91 mmol). The reaction is heated via microwave irradiation in a sealed microwave vessel to 110° C. for 1 hr. The reaction is concentrated to give the crude product. The crude product is purified via HPLC using a Waters XBridge 5 µm C18 OBD 30×75 mm column and eluted with a gradient of: 36% B isocratic for 3 min followed by 36-51% B over 5 min where solvent A is 10 mM ammonium bicarbonate in water with 5% MeOH and solvent B is acetonitrile. The desired fractions are combined and diluted with saturated NaHCO$_3$ (aq, 100 mL). The mixture is extracted with 4:1 CHCl$_3$:isopropanol (3×100 mL). The organic layers are combined, washed with brine (1×50 mL), dried over MgSO$_4$, filtered and concentrated to give the title compound (33 mg, 0.064 mmol): EZ/MS (m/z): 513 (M+H).

Preparation 152

N-[(4aR,7aR)-6-(5-Fluoropyrimidin-2-yl)-7a-isothiazol-5-yl-4,4a,5,7-tetrahydropyrrolo[3,4-d][1,3]thiazin-2-yl]benzamide

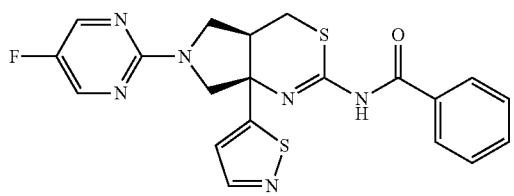 [SMILES: O=C(NC1=N[C@@]2(c3ccns3)CN(c3ncc(F)cn3)C[C@H]2CS1)c1ccccc1]

5-Fluoro-2-chloropyrimidine (58 mL, 608.3 mol), and diisopropylethylamine (227 mL 1.30 mol, 227.3 mL) is added to N-[(4aR,7aR)-7a-isothiazol-5-yl-4a,5,6,7-tetrahydro-4H-pyrrolo[3,4-d][1,3]thiazin-6-ium-2-yl]benzamide chloride (174.2 g, 434.5 mol), in N-methylpyrrolidone (1.4 L) at 22° C. and stirred. The reaction is heated at 100° C. for 4 hours and then cooled to room temperature. The crude mixture is added to water (14 L) and then stirred 1 hour. A white solid is collected by filtration and dried under vacuum to constant weight. The crude product is purified by silica gel chromatography, eluting with ethyl acetate: methylene chloride (3/1) to give the title compound (139 g, 72%). ES/MS (m/e): 441.0 (M+H).

Example A (4aR,7aS)-6-(5-Fluoropyrimidin-2-yl)-7a-phenyl-4,4a,5,7-tetrahydropyrrolo[3,4-d][1,3]thiazin-2-amine

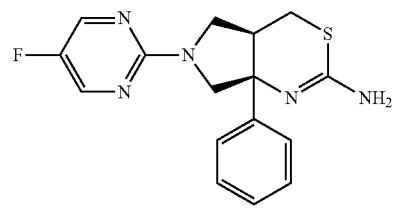 [SMILES: NC1=N[C@@]2(c3ccccc3)CN(c3ncc(F)cn3)C[C@H]2CS1]

Pyridine (20 mL, 197 mmol) is added to a mixture of N-[(4aR,7aS)-6-(5-fluoropyrimidin-2-yl)-7a-phenyl-4,4a,5,7-tetrahydropyrrolo[3,4-d][1,3]thiazin-2-yl]benzamide (9.5 g, 22 mmol), O-methylhydroxylamine hydrochloride (15 g, 175 mmol) in ethanol (85 mL) and the mixture is stirred at 60° C. for 2 hours. The mixture is cooled to ambient temperature and concentrated. The mixture is diluted with water (100 mL) and ethyl acetate (100 mL) and the pH to 2 using 1 M hydrochloric acid. The aqueous layer is separated and the pH is adjusted to 10 using 2 M sodium hydroxide. The resulting aqueous solution is extracted with ethyl acetate (2×100 mL). The organic layers are combined, dried over magnesium sulfate, filtered, and concentrated. The crude product is purified over silica gel using a 5% solution of dichloromethane/2 M ammonia in methanol. Chiral Analysis of the product; column: Chiralpak AD 0.46×15 cm, 5 µm; eluent: 100% (methanol with 0.2% dimethylethylamine); flow: 0.75 mL/min at UV 254 nm; R$_t$=6.9 minutes. (4.6 g, 64%, >98% ee). ES/MS (m/e): 330 (M+H).

Example B (4aR,7aR)-6-(5-Fluoropyrimidin-2-yl)-7a-(2-thienyl)-4,4a,5,7-tetrahydropyrrolo[3,4-d][1,3]thiazin-2-amine

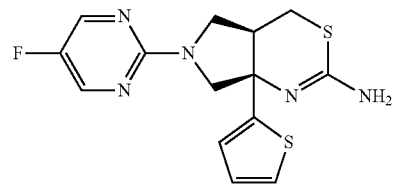 [SMILES: NC1=N[C@@]2(c3cccs3)CN(c3ncc(F)cn3)C[C@H]2CS1]

In a glass pressure vessel, a solution of N-[(4aR,7aR)-6-(5-fluoropyrimidin-2-yl)-7a-(2-thienyl)-4,4a,5,7-tetrahydropyrrolo[3,4-d][1,3]thiazin-2-yl]benzamide (6 g, 13.6 mmol) in ethanol (240 mL) is treated with pyridine (11 mL). O-methylhydroxylamine hydrochloride (11.4 g, 136.5 mmol) is added and the mixture is heated at 50° C. for 4 hours. The solution is concentrated and diluted with 1 M hydrochloric acid and ethyl acetate. The aqueous layer is separated and neutralized with 50% w/w aqueous solution of sodium hydroxide to adjust the pH to 9. The white precipitate is filtered and dried under vacuum. The crude product is crystallized in hot methyl-t-butyl ether until a complete solution is formed then the solution is cooled to room temperature. The solid precipitate is filtered and dried under vacuum to give the title compound (3.5 g, 76%). ES/MS (m/e): 336 (M+H).

The following compounds are prepared essentially by the method of Example B.

TABLE 25

| Ex. No. | Chemical name | Structure | ES/MS (m/e) (M + H) |
|---|---|---|---|
| C | Racemic 7a-(4-Fluorophenyl)-6-(5-fluoropyrimidin-2-yl)-4,4a,5,7-tetrahydropyrrolo[3,4-d][1,3]thiazin-2-amine[a] | 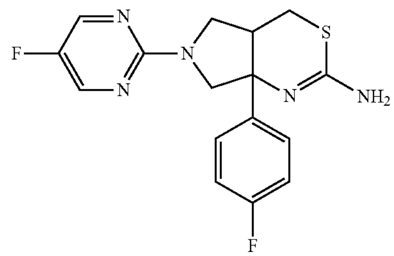 [SMILES: NC1=NC2(c3ccc(F)cc3)CN(c3ncc(F)cn3)CC2CS1] | 348 |
| D | Racemic 6-(5-Fluoropyrimidin-2-yl)-7a-thiazol-5-yl-4,4a,5,7-tetrahydropyrrolo[3,4-d][1,3]thiazin-2-amine[b] | 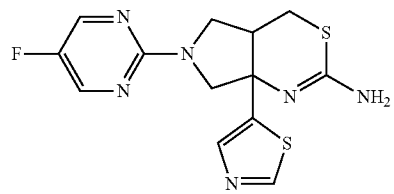 [SMILES: NC1=NC2(c3cncs3)CN(c3ncc(F)cn3)CC2CS1] | 337 |

[a] The reaction is concentrated and purified by silica gel chromatography eluting with a gradient of 0-100% ethyl acetate (10% isopropyl amine)/hexanes followed by a second purification with an SCX column and elution with MeOH, 1:1 MeOH:DCM, MeOH, and 2N $NH_3$ in MeOH to give the title product.
[b] The reaction is heated at 50° C. overnight and concentrated. The residue is purified by silica gel chromatography eluting with a 0.5% to 10% gradient of 7N $NH_3$ in MeOH:$CH_2Cl_2$.

X-Ray Powder Diffraction

Example B

The XRD patterns of crystalline solids are obtained on a Bruker D4 Endeavor X-ray powder diffractometer, equipped with a CuKα source (λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on National Bureau of Standards (NBS) 675 standard peaks at 8.853 and 26.774 degrees 2-theta.

Crystalline Example B (4aR,7aR)-6-(5-Fluoropyrimidin-2-yl)-7a-(2-thienyl)-4,4a,5,7-tetrahydropyrrolo[3,4-d][1,3]thiazin-2-amine (76 mg) is added to a 20 mL vial, and is dissolved in acetone (88%, 1.9 mL). Aliquots of water (1 mL) containing crystalline free base seeds are added as antisolvent. After 2 mL of antisolvent addition the solution is opaque white, and after the addition of 4 mL of the antisolvent, the sample is a thick slurry of bright white solid. The white solid is isolated by vacuum filtration and dried under air stream and vacuum on the filter for 10 minutes. The resulting cake of white solid (73 mg, 96%) is characterized by X-ray powder diffraction.

A prepared sample of the crystalline Example B is characterized by an X-ray powder diffraction pattern using CuKα radiation as having diffraction peaks (2-theta values) as described in Table 26 below, and in particular having peaks at 17.64 in combination with one or more of the peaks selected from the group consisting of 20.37, 21.89, and 5.84; with a tolerance for the diffraction angles of 0.2 degrees.

X-Ray Powder Diffraction Peaks of Crystalline Example B

TABLE 26

| Peak | Angle (°2-Theta) +/−0.2° | Relative Intensity (% of most intense peak) |
|---|---|---|
| 1 | 5.84 | 75.8 |
| 2 | 11.65 | 67.6 |
| 3 | 15.10 | 36.9 |
| 4 | 16.62 | 36.3 |
| 5 | 17.64 | 100 |
| 6 | 17.98 | 33.9 |
| 7 | 20.37 | 99.4 |
| 8 | 21.32 | 45.3 |
| 9 | 21.89 | 97.3 |
| 10 | 22.60 | 33.7 |

TABLE 26-continued

| Peak | Angle (°2-Theta) +/−0.2° | Relative Intensity (% of most intense peak) |
|---|---|---|
| 11 | 25.55 | 36.1 |
| 12 | 26.23 | 43.8 |

Example E

5-[(4aR,7aR)-2-Amino-6-(5-fluoropyrimidin-2-yl)-4a,5,6,7-tetrahydropyrrolo[3,4-d][1,3]thiazin-7a(4H)-yl]thiophene-2-carbonitrile

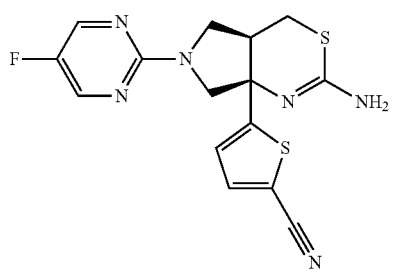 [SMILES: N#Cc1ccc([C@]23CN(c4ncc(F)cn4)C[C@H]2CSC(N)=N3)s1]

To N-[(4aR,7aR)-7a-(5-cyanothiophen-2-yl)-6-(5-fluoropyrimidin-2-yl)-4,4a,5,6,7,7a-hexahydropyrrolo[3,4-d][1,3]thiazin-2-yl]benzamide (442 mg, 0.951 mmol) in ethanol (19 mL) is added pyridine (752.6 mg, 9.5 mmol) and O-methylhydroxylamine HCl (794.6 mg, 9.5 mmol). The mixture is heated to 55° C. under an atmosphere of nitrogen for 12 hours. The mixture is concentrated, dissolved in dichloromethane and concentrated again. The residue is dissolved in ethyl acetate and water and washed with saturated aqueous NaHCO₃. The phases are separated and the aqueous phase extracted with ethyl acetate (30 mL). The organic phases are combined, dried over Na₂SO₄, filtered, and concentrated. The residue is purified with silica gel chromatography eluting with a 70:30 to 0:100 hexane/ethyl acetate gradient. The isolated product is repurified with silica gel chromatography eluting with 70:30 dichloromethane/ethyl acetate for 20 minutes and then a gradient to 0:100 to give the title product (294 mg, 86%). ES/MS (m/e): 361 (M+H).

Example F

[(4aR,7aR)-7a-(5-Fluorothiophen-2-yl)-6-(pyrimidin-2-yl)-4,4a,5,6,7,7a-hexahydropyrrolo[3,4-d][1,3]thiazin-2-amine

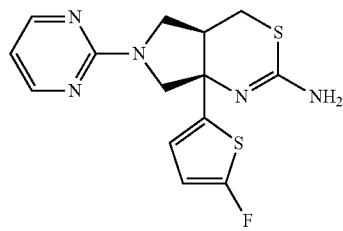 [SMILES: NC1=N[C@@]2(c3ccc(F)s3)CN(c3ncccn3)C[C@H]2CS1]

To N-[(4aR,7aR)-7a-(5-fluorothiophen-2-yl)-6-(pyrimidin-2-yl)-4,4a,5,6,7,7a-hexahydropyrrolo[3,4-d][1,3]thiazin-2-yl]benzamide (456 mg, 1.04 mmol) is added methanol (10.4 mL) and lithium hydroxide (218 mg, 5.19 mmol). The solution is heated to reflux for 2.5 hours under an atmosphere of nitrogen. The resulting solution is allowed to cool for a few minutes then concentrated under reduced pressure. The residue is extracted with dichloromethane (30 mL) and water (30 mL). The phases are partitioned and the aqueous phase further extracted with dichloromethane (1×30 mL). The combined dichloromethane extracts are dried over sodium sulfate, filtered, and concentrated under reduced pressure. The residue is purified by silica gel chromatography eluting with dichloromethane/methanol, gradient from 99:1 to 90:10, to give the title compound (330 mg, 95%) as an amorphous white solid. ES/MS (m/e): 335.8 (M+H).

Example G

[(4aR,7aR)-6-(5-Fluoropyrimidin-2-yl)-7a-(5-fluorothiophen-2-yl)-4,4a,5,6,7,7a-hexahydropyrrolo[3,4-d][1,3]thiazin-2-amine

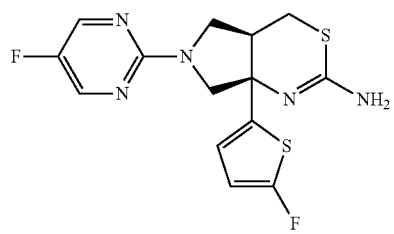 [SMILES: NC1=N[C@@]2(c3ccc(F)s3)CN(c3ncc(F)cn3)C[C@H]2CS1]

To N-[(4aR,7aR)-6-(5-fluoropyrimidin-2-yl)7a-(5-fluorothiophen-2-yl)-4,4a,5,6,7,7a-hexahydropyrrolo[3,4-d][1,3]thiazin-2-yl]benzamide (391 mg, 855 mmol) is added methanol (8.5 mL) and lithium hydroxide (179 mg, 4.27 mmol). The solution is heated to reflux for 2.5 hours under an atmosphere of nitrogen. The resulting solution is allowed to cool for a few minutes then concentrated under reduced pressure. The residue is extracted with dichloromethane (30 mL) and water (30 mL). The phases are partitioned and the aqueous phase further extracted with dichloromethane (1×30 mL). The combined dichloromethane extracts are dried over sodium sulfate, filtered, and concentrated under reduced pressure. The residue is purified by silica gel chromatography eluting with dichloromethane/methanol, gradient from 99:1 to 90:10, to give the title compound (263 mg, 87%) as an amorphous white foam. ES/MS (m/e): 354.0 (M+H).

Example H

Racemic 7a-(2-Fluorophenyl)-6-(5-fluoropyrimidin-2-yl)-4,4a,5,7-tetrahydropyrrolo[3,4-d][1,3]thiazin-2-amine

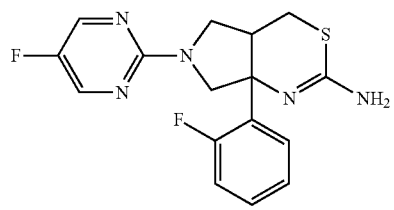 [SMILES: NC1=NC2(c3ccccc3F)CN(c3ncc(F)cn3)CC2CS1]

Racemic N-[7a-(2-fluorophenyl)-6-(5-fluoropyrimidin-2-yl)-4,4a,5,7-tetrahydropyrrolo[3,4-d][1,3]thiazin-2-yl]benzamide (560 mg, 1.24 mmol), methanol (12 ml), and lithium hydroxide (208 mg, 4.95 mmol) is heated to 50° C. for 18 hours under an atmosphere of nitrogen. The methanol is removed to near dryness with a stream of nitrogen. To the reaction is added ethyl acetate (7.5 ml), and water (2.5 ml). The mixture is passed through 10 g diatomaceous earth and the solvent removed under reduced pressure. The filtrate is passed through a 8 g XL-C solid phase extraction column (SPE), the basic methanol wash collected, and the solvent removed under reduced pressure to provide the crude title compound (370 mg, 86%). ES/MS (m/e): 348 (M+H).

Example I (4aR,7aS)-7a-(2-Fluorophenyl)-6-(5-fluoropyrimidin-2-yl)-4,4a,5,7-tetrahydropyrrolo[3,4-d][1,3]thiazin-2-amine, isomer 2

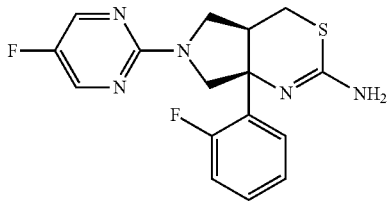 [SMILES: NC1=N[C@@]2(c3ccccc3F)CN(c3ncc(F)cn3)C[C@H]2CS1]

Racemic 7a-(2-fluorophenyl)-6-(5-fluoropyrimidin-2-yl)-4,4a,5,7-tetrahydropyrrolo[3,4-d][1,3]thiazin-2-amine (361 mg, 1.04 mmol) is purified by chiral HPLC (Column: Chiralpak AD-H (5 u), 3×25 cm; eluent: 100% methanol (0.2% isopropylamine); flow 30 mL/min at UV 225 nm. The second eluting isomer is the title compound (114 mg, 32%, 99% ee). $R_t$=4.887 minutes; column: Chiralpak AD-H 0.46×15 cm; eluent: 100% methanol (0.2% isopropylamine) in $CO_2$; flow: 1 mL/min at UV 225 nm.

Example J

6(4aR,7aR)-6-(5-Fluoropyrimidin-2-yl)-7a-thiazol-5-yl-4,4a,5,7-tetrahydropyrrolo[3,4-d][1,3]thiazin-2-amine, isomer 1

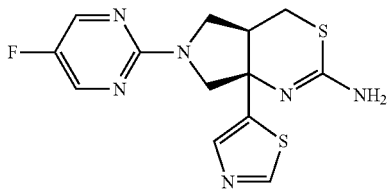 [SMILES: NC1=N[C@@]2(c3cncs3)CN(c3ncc(F)cn3)C[C@H]2CS1]

Racemic 6-(5-Fluoropyrimidin-2-yl)-7a-thiazol-5-yl-4, 4a,5,7 tetrahydropyrrolo[3,4-d][1,3]thiazin-2-amine (122 mg, 285 µmol) is chirally purified by SFC (Column: Chiralpak AD-H 2.1×15 cm; eluent: 40% methanol (0.2% isopropylamine) in $CO_2$; flow: 70 mL/min at UV 225 nm). The first eluting isomer is the title compound (40 mg, 33%, 99% ee). $R_t$=1.51 minutes; column: Chiralpak AD-H 0.46×15 cm; eluent: 40% methanol (0.2% isopropylamine) in $CO_2$; flow: 5 mL/min at UV 225 nm.

Example K

5-[(4aR,7aR)-2-Amino-6-[5-fluoro-4-(2-hydroxypropan-2-yl)pyrimidin-2-yl]-4a,5,6,7-tetrahydropyrrolo[3,4-d][1,3]thiazin-7a(4H)-yl]thiophene-2-carbonitrile

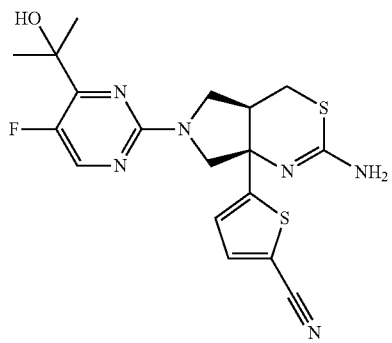 [SMILES: CC(C)(O)c1nc(N2C[C@H]3CSC(N)=N[C@@]3(c3ccc(C#N)s3)C2)ncc1F]

To a stirred solution of N-{(4aR,7aR)-7a-(5-cyanothiophen-2-yl)-6-[5-fluoro-4-(2-hydroxypropan-2-yl)pyrimidin-2-yl]-4,4a,5,6,7,7a-hexahydropyrrolo[3,4-d][1,3]thiazin-2-yl}benzamide (364 mg, 0.697 mmol) in ethanol (14 mL) is added pyridine (563 µL, 6.96 mmol) and O-methylhydroxylamine hydrochloride (582 mg, 6.96 mmol). The solution is heated to 55° C. under an atmosphere of nitrogen for 21 hours. The resulting solution is allowed to cool for a few minutes then concentrated under reduced pressure. Dichloromethane (30 mL) is added and again the solution is concentrated under reduced pressure. The residue is diluted with ethyl acetate (50 mL), water (25 mL), and saturated aqueous sodium bicarbonate (10 mL). The phases are separated and the ethyl acetate phase is dried over sodium sulfate, filtered, and concentrated under reduced pressure. The residue is purified by silica gel chromatography, eluting with dichloromethane/ethyl acetate, 70:30 for 20 minutes, and then a gradient to 0:100 to give the title compound (261 mg, 90%) as a white foam. MS/ES (m/z) 419.0 (M+H).

Example L (4aR,7aR)-6-(5-Fluoropyrimidin-2-yl)-7a-isothiazol-5-yl-4,4a,5,7-tetrahydropyrrolo[3,4-d][1,3]thiazin-2-amine

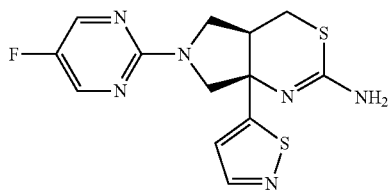 [SMILES: NC1=N[C@@]2(c3ccns3)CN(c3ncc(F)cn3)C[C@H]2CS1]

N-[(4aR,7aR)-6-(5-Fluoropyrimidin-2-yl)-7a-isothiazol-5-yl-4,4a,5,7-tetrahydropyrrolo[3,4-d][1,3]thiazin-2-yl]benzamide (5 g, 11.5 mmol) is added to lithium hydroxide (530 mg, 12.6 mmol) in methanol (50 mL) at 22° C. The reaction mixture is refluxed for 3 hours and then cooled to 22° C. Hydrogen chloride, 2 M in water (20.3 mL) is added and then solvent is evaporated. The solution is washed with MTBE (50 mL). The aqueous solution is treated with charcoal (500 mg) and stirred 30 minutes at 22° C. The mixture is filtered over diatomaceous earth and the pH of the filtrate is adjusted to pH=9 with sodium hydroxide (2M aqueous solution). A white solid precipitates and is collected. The solid is dried under vacuum to a constant weight to give the title compound (1 g, 30%). ES/MS (m/e): 337 (M+H).

Example 1

(4aR,7aS)-6-(5-Fluoropyrimidin-2-yl)-7a-phenyl-4,4a,5,7-tetrahydropyrrolo[3,4-d][1,3]thiazin-2-amine hydrochloride

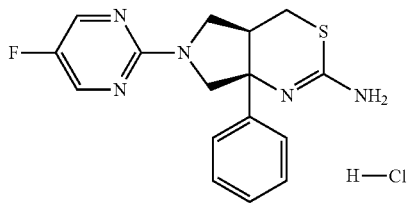 [SMILES: NC1=N[C@@]2(c3ccccc3)CN(c3ncc(F)cn3)C[C@H]2CS1 ; Cl]

A solution of N-[(4aR,7aS)-6-(5-fluoropyrimidin-2-yl)-7a-phenyl-4,4a,5,7-tetrahydropyrrolo[3,4-d][1,3]thiazin-2-yl]benzamide (215 mg, 0.496 mmol), O-methylhydroxylamine hydrochloride (207 mg, 2.48 mmol), and pyridine (392 mg, 4.96 mmol) in ethanol (5 ml) is stirred at 55° C. for 4 hours. The mixture is quenched with a solution of saturated sodium bicarbonate in water, and extracted with ethyl acetate. The organic layers are combined, dried, filtered, and concentrated under reduced pressure to give a residue. The residue is purified by silica gel flash chromatography, eluting with hexane/ethyl acetate (1:0) to hexane/ethyl acetate (0:1) to give a residue as the free base of the title compound. The residue is dissolved in 1 N hydrochloric acid (4 ml), and the solvent removed by a stream of nitrogen. The resulting solid is further purified by dissolving in 1/1 acetonitrile/methanol (4 ml) and precipitating with ethyl ether (2-3 ml). The solid is collected and dried under reduced pressure at 50° C. to give the title compound (0.10 g, 55%). ES/MS (m/e): 330 (M+H).

The following Examples are prepared essentially by the method of Example 1 except when a free base is shown there is no treatment with hydrogen chloride.

TABLE 27

| Ex. No. | Chemical name | Structure | ES/MS (m/e) |
|---|---|---|---|
| 2 | (4aR,7aS)-7a-Phenyl-6-pyrimidin-2-yl-4,4a,5,7-tetrahydropyrrolo[3,4-d][1,3]thiazin-2-amine dihydrochloride | 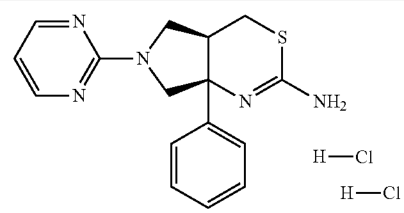 | 312 (M + H) |
| 3 | (4aR,7aR)-6-(4-Isopropylpyrimidin-2-yl)-7a-(2-thienyl)-4,4a,5,7-tetrahydropyrrolo[3,4-d][1,3]thiazin-2-amine dihydrochloride, isomer 1 | 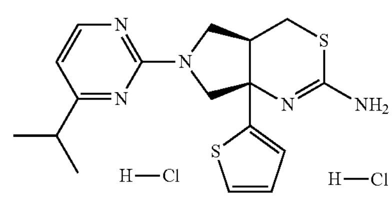 | 360 (M + H) |
| 4 | (4aR,7aR)-6-Pyrimidin-2-yl-7a-(2-thienyl)-4,4a,5,7-tetrahydropyrrolo[3,4-d][1,3]thiazin-2-amine dihydrochloride, | 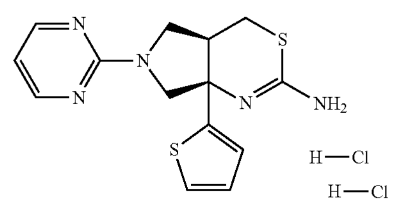 | 318 (M + H) |
| 5 | (4aR,7aR)-6-(4-Cyclopropylpyrimidin-2-yl)-7a-(2-thienyl)-4,4a,5,7-tetrahydropyrrolo[3,4-d][1,3]thiazin-2-amine dihydrochloride, isomer 1 | 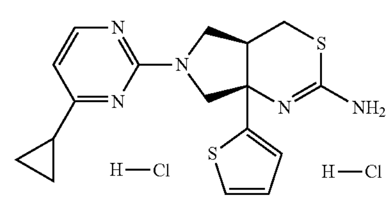 | 358 (M + H) |
| 6 | Racemic 6-Pyrimidin-2-yl-7a-thiazol-5-yl-4,4a,5,7-tetrahydropyrrolo[3,4-d][1,3]thiazin-2-amine dihydrochloride | 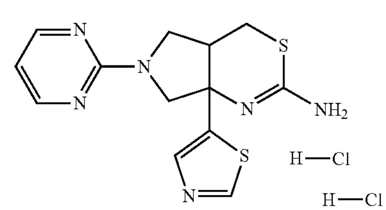 | 319 (M + H) |

TABLE 27-continued

| Ex. No. | Chemical name | Structure | ES/MS (m/e) |
|---|---|---|---|
| 7 | (4aR,7aR)-6-(4-Isopropylpyrimidin-2-yl)-7a-thiazol-5-yl-4,4a,5,7-tetrahydropyrrolo[3,4-d][1,3]thiazin-2-amine dihydrochloride, isomer 1 | 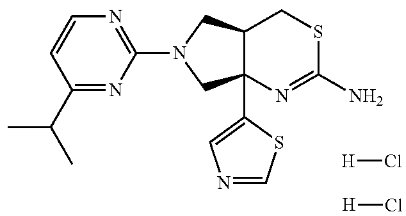 | 361 (M + H) |
| 8 | (4aR,7aR)-6-(5-Fluoro-4-isopropyl-pyrimidin-2-yl)-7a-thiazol-5-yl-4,4a,5,7-tetrahydropyrrolo[3,4-d][1,3]thiazin-2-amine dihydrochloride | 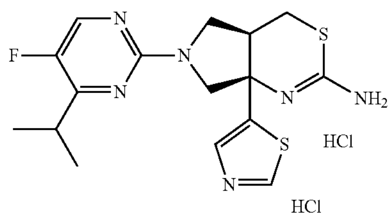 [SMILES: CC(C)c1nc(N2C[C@H]3CSC(N)=N[C@@]3(c3cncs3)C2)ncc1F ; Cl ; Cl] | 379 (M + H) |
| 9 | Racemic 6-(4-Cyclopropylpyrimidin-2-yl)-7a-thiazol-5-yl-4,4a,5,7-tetrahydropyrrolo[3,4-d][1,3]thiazin-2-amine | 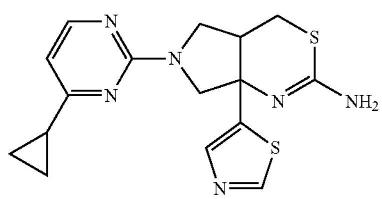 [SMILES: NC1=NC2(c3cncs3)CN(c3nccc(C4CC4)n3)CC2CS1] | 359 (M + H) |
| 10 | (4aR,7aR)-6-Pyrimidin-2-yl-7a-(2-thienyl)-4,4a,5,7-tetrahydropyrrolo[3,4-d][1,3]thiazin-2-amine | 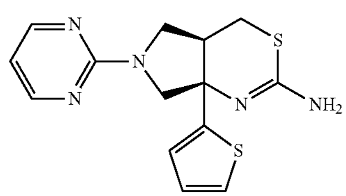 [SMILES: NC1=N[C@@]2(c3cccs3)CN(c3ncccn3)C[C@H]2CS1] | 318 (M + H) |
| 11 | Racemic 6-Pyrimidin-2-yl-7a-(2-thienyl)-4,4a,5,7-tetrahydropyrrolo[3,4-d][1,3]thiazin-2-amine | 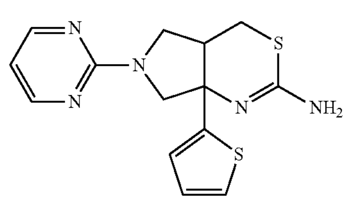 [SMILES: NC1=NC2(c3cccs3)CN(c3ncccn3)CC2CS1] | 318 (M + H) |

Example 1

Alternate Procedure (4aR,7aS)-6-(5-Fluoropyrimidin-2-yl)-7a-phenyl-4,4a,5,7-tetrahydropyrrolo[3,4-d][1,3]thiazin-2-amine hydrochloride

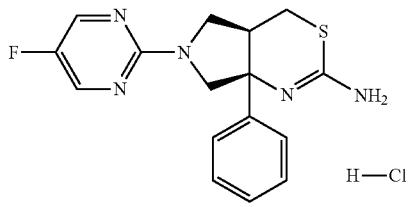 [SMILES: NC1=N[C@@]2(c3ccccc3)CN(c3ncc(F)cn3)C[C@H]2CS1 ; Cl]

A solution of hydrogen chloride (1 M in diethyl ether) (17 mL, 17 mmol) is added to a solution of (4aR,7aS)-6-(5-fluoropyrimidin-2-yl)-7a-phenyl-4,4a,5,7-tetrahydropyrrolo[3,4-d][1,3]thiazin-2-amine (4.6 g, 14 mmol) in ethyl acetate (46 mL) and stirred for one hour. The solvent is removed under vacuum to give the title compound (5 g, 98%). ES/MS (m/e): 330 (M+H).

The following Example is prepared essentially by the method of Example 1, alternate procedure except dichloromethane is used as the reaction solvent.

TABLE 28

| Ex. No. | Chemical name | Structure | ES/MS (m/e) |
|---|---|---|---|
| 12 | (4aR,7aR)-6-(5-Fluoropyrimidin-2-yl)-7a-thiazol-5-yl-4,4a,5,7-tetrahydropyrrolo[3,4-d][1,3]thiazin-2-amine dihydrochloride, isomer 2 | 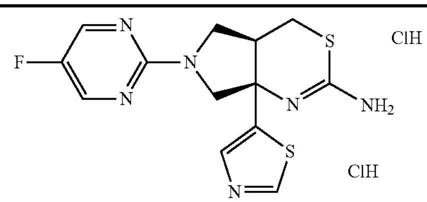 | 337 (M + H) |

Example 13

Racemic 7a-(5-Fluoro-2-thienyl)-6-pyrimidin-2-yl-4,4a,5,7-tetrahydropyrrolo[3,4-d][1,3]thiazin-2-amine

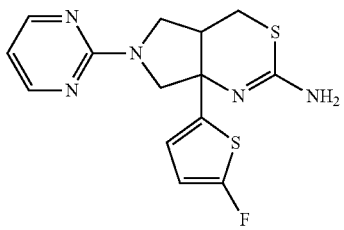 [SMILES: NC1=NC2(c3ccc(F)s3)CN(c3ncccn3)CC2CS1]

To a stirred solution of the N-[7a-(5-fluoro-2-thienyl)-6-pyrimidin-2-yl-4,4a,5,7-tetrahydropyrrolo[3,4-d][1,3]thiazin-2-yl]benzamide (100 mg, 0.228 mmol) in ethanol (4.6 mL) is added pyridine (0.184 mL, 2.28 mmol) and O-methylhydroxylamine hydrochloride (190 mg, 2.28 mmol). The resulting mixture is heated at 58° C. for 15 hours. The solution is allowed to cool to room temperature, diluted with ethyl acetate (25 mL), and washed with dilute sodium bicarbonate ((20 mL) prepared from water (10 mL) and saturated sodium bicarbonate (10 mL)). The aqueous phase is extracted with ethyl acetate (25 mL). The combined organic extracts are dried over sodium sulfate, filtered, and concentrated. The residue is purified by silica gel flash chromatography eluting with dichloromethane/7 M ammonia in methanol, gradient from 99:1 to 95:5, to give the title compound (65 mg, 0.194 mmol, 85%) as a white solid. ES/MS (m/e): 336 (M+H).

Example 14

(4aR,7aS)-6-(5-Fluoro-4-methoxy-6-methyl-pyrimidin-2-yl)-7a-phenyl-4,4a,5,7-tetrahydropyrrolo[3,4-d][1,3]thiazin-2-amine hydrochloride

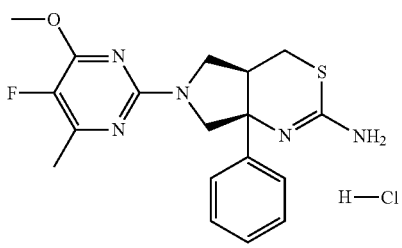 [SMILES: COc1nc(N2C[C@H]3CSC(N)=N[C@@]3(c3ccccc3)C2)nc(C)c1F ; Cl]

To a solution of N-[(4aR,7aS)-6-(5-fluoro-4-methoxy-6-methyl-pyrimidin-2-yl)-7a-phenyl-4,4a,5,7-tetrahydropyrrolo[3,4-d][1,3]thiazin-2-yl]benzamide (68 mg, 0.14 mmol) in ethanol (5.0 mL) is added pyridine (0.115 mL, 1.42 mmol) and O-methylhydroxylamine hydrochloride (118 mg, 1.42 mmol). The mixture is heated to 55° C. for 16 hours, cooled to ambient temperature, and concentrated to dryness. The residue is purified by silica gel flash chromatography, eluting with a gradient of 0 to 100% of hexane/ethyl acetate:10% isopropyl amine to give the free base form of the title compound as a colorless oil. Dissolve this residue in dichloromethane (3 mL) and add 4 N HCl in dioxane (2 mL) and stir for 5 minutes. The solution is then concentrated to give the title compound as an off white solid (50 mg, 86%). ES/MS (m/e) 374.0 (M+H).

Example 15

5-[(4aR,7aR)-2-Amino-6-(5-fluoropyrimidin-2-yl)-4,4a,5,7-tetrahydropyrrolo[3,4-d][1,3]thiazin-7a-yl]thiophene-3-carbonitrile, isomer 1

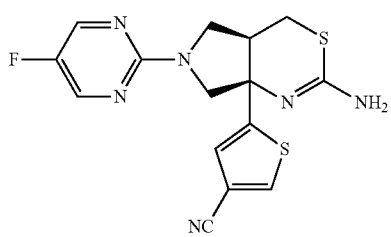 [SMILES: N#Cc1csc([C@]23CN(c4ncc(F)cn4)C[C@H]2CSC(N)=N3)c1]

Racemic N-[7a-(4-cyano-2-thienyl)-6-(5-fluoropyrimidin-2-yl)-4,4a,5,7-tetrahydropyrrolo[3,4-d][1,3]thiazin-2-yl]benzamide (1.01 g, 2.17 mmol), pyridine (2.64 mL, 32.6 mmol), and O-methylhydroxylamine hydrochloride (1.82 g, 21.7 mmol) in ethanol (250 mL) are stirred at 60° C. for 24 hours. The mixture is cooled to ambient temperature and concentrated. The mixture is diluted with water and extracted with DCM followed by 3:1 chloroform:isopropyl alcohol. The organic layers are combined, dried over sodium sulfate, filtered, and concentrated. The crude product is purified over silica gel using a gradient of hexane:ethyl acetate (1:0 to 0:1, over 30 min) The product is chirally separated by SFC (Column: Chiralpak AS-H 2.1×15 cm; 5µ; eluent: 30% methyl alcohol with 0.2% isopropylamine) in $CO_2$; flow: 70 mL/minute at 225 nm). The first eluting isomer is the title compound (99% ee). Analysis column: Chiralpak AS-H 4.6× 150 mm; eluent: 30% methyl alcohol with 0.2% isopropylamine) in $CO_2$; flow: 5.0 mL/min at UV 225 nm, RT=1.08 minutes). ES/MS (m/e): 361 (M+H).

Example 16

(4aR,7aR)-6-(5-Fluoropyrimidin-2-yl)-7a-(2-thienyl)-4,4a,5,7-tetrahydropyrrolo[3,4-d][1,3]thiazin-2-amine hydrochloride

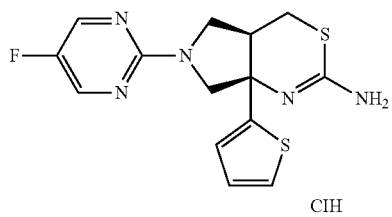

A solution of N-[(4aR,7aR)-6-(5-fluoropyrimidin-2-yl)-7a-(2-thienyl)-4,4a,5,7-tetrahydropyrrolo[3,4-d][1,3]thiazin-2-yl]benzamide (645 mg, 1.47 mmol), O-methylhydroxylamine hydrochloride (613 mg, 7.34 mmol), and pyridine (1.16 g, 14.7 mmol) in ethanol (10 mL) is stirred at 55° C. for 4 hours. The mixture is quenched with a solution of saturated sodium bicarbonate in water and extracted with ethyl acetate. The organic layers are combined, dried, filtered, and concentrated under reduced pressure to give a residue. The residue is purified by silica gel flash chromatography, eluting with hexane/ethyl acetate (1:1) to hexane/ethyl acetate (0:1). The residue is further purified by portioning between ethyl acetate and 1 N hydrochloric acid. The acidic aqueous phase is collected and the pH is adjusted to >8 with 5 N sodium hydroxide. The basic aqueous phase is extracted with dichloromethane, dried and concentrated to give the title compound as the free base. The free base is dissolved in dichloromethane. To the solution is added a saturated solution of hydrogen chloride in dichloromethane, followed by diethyl ether (10 mL). The resulting white solid is collected by filtration to give the title compound (0.40 g, 74%). ES/MS (m/e): 336 (M+H).

The following Examples are prepared essentially by the method of Example 16.

TABLE 29

| Ex. No. | Chemical name | Structure | ES/MS (m/e) |
|---|---|---|---|
| 17[a] | (4aR,7aR)-6-[5-Fluoro-4-(1-Fluoro-1-methyl-ethyl)pyrimidin-2-yl]-7a-isothiazol-5-yl-4,4a,5,7-tetrahydropyrrolo[3,4-d][1,3]thiazin-2-amine hydrochloride, isomer 2 | 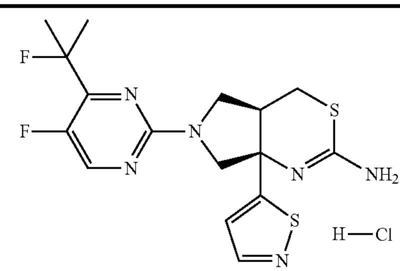 | 397 (M + H) |
| 18[b] | (4aR,7aS)-6-(4-Ethyl-5-Fluoro-pyrimidin-2-yl)-7a-phenyl-4,4a,5,7-tetrahydropyrrolo[3,4-d][1,3]thiazin-2-amine hydrochloride | 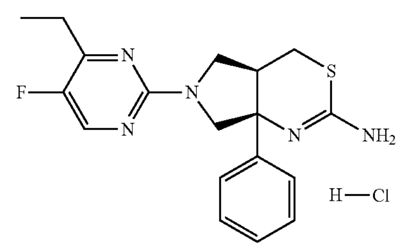 | 358 (M + H) |
| 19[b] | [2-[(4aR,7aS)-2-Amino-7a-phenyl-4,4a,5,7-tetrahydropyrrolo[3,4-d][1,3]thiazin-6-yl]-5-fluoro-pyrimidin-4-yl]methanol hydrochloride | 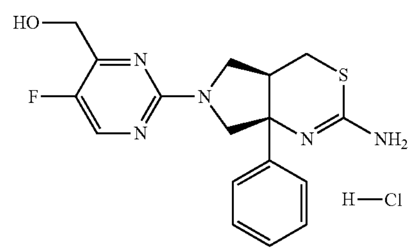 | 360 (M + H) |

[a]Reaction is stirred for 18 hours at 60° C.;
[b]Reaction is stirred for 2.5 days at room temperature.

Crystalline Example 16

(4aR,7aR)-6-(5-Fluoropyrimidin-2-yl)-7a-(2-thienyl)-4,4a,5,7-tetrahydropyrrolo[3,4-d][1,3]thiazin-2-amine (177 mg) is placed in a vial. The solid is mixed with acetone (3 mL) while stirring at 1000 rpm giving a clear colorless solution. HCl (1 M in EtOAc, 600 μL) is added drop wise and a white precipitate forms in a slurry. The white solid in is isolated by vacuum filtration and dried under air stream and vacuum on the filter for 10 minutes to give a white solid (186 mg, 94.8%).

A prepared sample of Example 16 is characterized by an X-ray powder diffraction pattern using CuKα radiation as having diffraction peaks (2-theta values) as described in Table 30 below, and in particular having peaks at 21.00 in combination with one or more of the peaks selected from the group consisting of 18.11, 22.76, and 19.96; with a tolerance for the diffraction angles of 0.2 degrees.

X-Ray Powder Diffraction Peaks of Example 16

TABLE 30

| Peak | Angle (°2-Theta) +/−0.2° | Relative Intensity (% of most intense peak) |
|---|---|---|
| 1 | 9.89 | 52.2 |
| 2 | 10.43 | 53.3 |
| 3 | 11.32 | 53.5 |
| 4 | 12.35 | 53.8 |
| 5 | 18.11 | 77.6 |
| 6 | 18.54 | 55.4 |
| 7 | 19.96 | 59.6 |
| 8 | 21.00 | 100.0 |
| 9 | 22.76 | 61.6 |
| 10 | 23.49 | 51.6 |

Example 16

Alternate Procedure (4aR,7aR)-6-(5-Fluoropyrimidin-2-yl)-7a-(2-thienyl)-4,4a,5,7-tetrahydropyrrolo[3,4-d][1,3]thiazin-2-amine hydrochloride

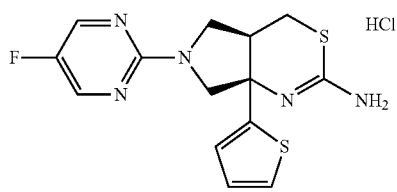 [SMILES: NC1=N[C@@]2(c3cccs3)CN(c3ncc(F)cn3)C[C@H]2CS1 ; Cl]

A solution of (4aR,7aR)-6-(5-fluoropyrimidin-2-yl)-7a-(2-thienyl)-4,4a,5,7-tetrahydropyrrolo[3,4-d][1,3]thiazin-2-amine (3.8 g, 11.33 mmol) in a solution of methyl-t-butyl ether (50 mL) and ethyl acetate (10 mL) is treated with hydrogen chloride (1 M in diethyl ether) (13.6 mL, 13.6 mmol). The mixture is stirred for 10 minutes, concentrated and the product is dried under vacuum to give the title compound (4.1 g, 97%). ES/MS (m/e): 336 (M+H). Chiral analysis: (Column: Chiralpak AS (5 u), C18 4.6×100 mm; eluent: 25% methanol with 0.2% dimethylethylamine) in CO₂; flow 2.5 mL/min at UV 220 nm) to confirm the title compound, (>99% ee, $R_t$=1.44 min).

Example 20

(4aR,7aS)-7a-(4-Fluorophenyl)-6-(5-fluoropyrimidin-2-yl)-4,4a,5,6-tetrahydropyrrolo[3,4-d][1,3]thiazin-2-amine hydrochloride

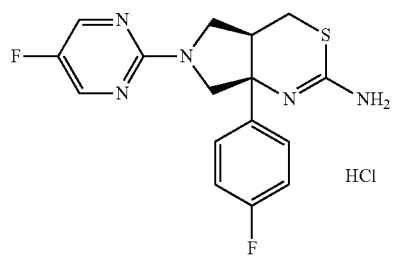 [SMILES: NC1=N[C@@]2(c3ccc(F)cc3)CN(c3ncc(F)cn3)C[C@H]2CS1 ; Cl]

Racemic 7a-(4-fluorophenyl)-6-(5-fluoropyrimidin-2-yl)-4,4a,5,7-tetrahydropyrrolo[3,4-d][1,3]thiazin-2-amine (437 mg, 1.26 mmol) is chirally purified by SFC (Column: Chiralpak AD-H (5 u), 2.1×15 cm; eluent: 40% isopropyl alcohol (0.2% isopropylamine) in CO₂; flow 70 mL/min at UV 225 nm). The second eluting isomer is dissolved in 15 mL dichloromethane and hydrogen chloride gas is bubbled through the solution for approximately 15 seconds and concentrated to give the title compound as a white solid (194 mg, 40%, >99% ee). ES/MS (m/e) 348 (M+H).

Example 21

3-[(4aR,7aS)-2-Amino-6-(5-fluoropyrimidin-2-yl)-4,4a,5,7-tetrahydropyrrolo[3,4-d][1,3]thiazin-7a-yl]benzonitrile hydrochloride

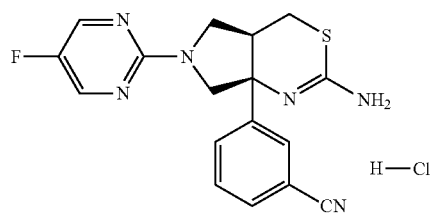 [SMILES: N#Cc1cccc([C@]23CN(c4ncc(F)cn4)C[C@H]2CSC(N)=N3)c1 ; Cl]

To a solution of racemic N-[7a-(3-bromophenyl)-6-(5-fluoropyrimidin-2-yl)-4,4a,5,7-tetrahydropyrrolo[3,4-d][1,3]thiazin-2-yl]benzamide (180 mg, 393 μmol) in ethanol (8.0 mL) is added sequentially pyridine (0.5 mL, 6.2 mmol) and O-methylhydroxylamine hydrochloride (350 mg, 4.19 mmol). The mixture is heated at 60° C. for 16 hours, cooled to ambient temperature, and concentrated to dryness. The residue is purified by silica gel flash chromatography, eluting with a gradient of 0 to 10% of dichloromethane/2 M ammonia in methanol to give the free base form of the title compound as a colorless oil. The racemic material is separated chirally by SFC (Column: Chiralpak AS-H, 5 p; eluent: 35% isopropyl alcohol with 0.2% isopropylamine) in CO₂; flow: 70 mL/minute at 225 nm). The first eluting isomer is the free base of the title compound, (R$_t$=0.92 minutes). EI/MS (m/e): 355 (M+H). This isomer is dissolved in dichloromethane (1 mL) and hydrogen chloride gas is bubbled through this solution for approximately 10 seconds. The solution is then concentrated to give the title compound as a white solid (55 mg, 36%, >99% ee).

Example 22

N-[(4aR,7aS)-6-[5-Fluoro-4-(1-hydroxy-1-methyl-ethyl)-6-methyl-pyrimidin-2-yl]-7a-phenyl-4,4a,5,7-tetrahydropyrrolo[3,4-d][1,3]thiazin-2-yl]benzamide hydrochloride

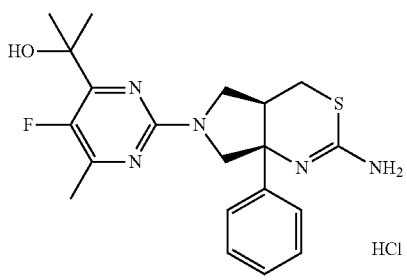 [SMILES: Cc1nc(N2C[C@H]3CSC(N)=N[C@@]3(c3ccccc3)C2)nc(C(C)(C)O)c1F ; Cl]

To a solution of N-[(4aR,7aS)-7a-phenyl-4a,5,6,7-tetrahydro-4H-pyrrolo[3,4-d][1,3]thiazin-2-yl]benzamide hydrochloride (95 mg, 0.25 mmol) and 2-(2-chloro-5-fluoro-pyrimidin-4-yl)propan-2-ol (195 mg, 0.57 mmol) in 1,4-dioxane (5.0 mL) is added diisopropylethylamine (150 µL, 0.86 mmol). The resulting solution is heated at 100° C. for 23 hours, cooled to room temperature, and concentrated. The residue is dissolved in methanol (5.0 mL), followed by the addition of lithium hydroxide (100 mg, 4.11 mmol). The resulting solution is heated at 55° C. for 16 hrs and then cooled to room temperature and concentrated. The residue is purified with a 5 g SCX column, eluting first with MeOH/DCM (¼, 50 mL), followed by elution with ammonia in MeOH (7.0 N)/DCM (¼, 50 mL). The basic filtrate is concentrated, and further purified by silica gel flash chromatography, eluting with a gradient of ammonia in MeOH (2.0 M) in dichloromethane (0% to 10%) to give the free base form of the title compound as a colorless oil. EI/MS (m/e): 402.00 (M+H). ¹⁹F-NMR (CDCl₃): δ (ppm) −154.62. ¹H-NMR (CDCl₃): δ (ppm) 7.38 (m, 5H), 4.11 (d, 1H), 4.01 (d, 1H), 3.83 (m, 2H), 3.05 (dd, 1H), 2.92 (dd, 1H), 2.81 (m, 1H), 2.37 (s, 3H), 1.53 (s, 6H). The purified material is dissolved in dichloromethane (2 mL), followed by the addition of HCl (1.0 M in diethyl ether, 60 µL, 0.06 mmol) and then concentrated to give the title compound as a white solid (22 mg, 20%).

Example 23

(4aR,7aR)-6-(5-Fluoropyrimidin-2-yl)-7a-isothiazol-5-yl-4,4a,5,7-tetrahydropyrrolo[3,4-d][1,3]thiazin-2-amine hydrochloride

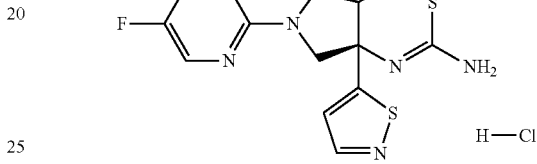

Lithium hydroxide (91.45 mg, 2.18 mmol) is added to a solution of N-[(4aR,7aR)-6-(5-fluoropyrimidin-2-yl)-7a-isothiazol-5-yl-4,4a,5,7-tetrahydropyrrolo[3,4-d][1,3]thiazin-2-yl]benzamide, isomer 2 (190 mg, 0.44 mmol) in methanol (8 mL) and is heated at reflux for 3 hours. The reaction is cooled to room temperature, diluted with water, and extracted with ethyl acetate. The aqueous layer is re-extracted twice with ethyl acetate. The organic layers are combined, dried over sodium sulfate, and the solvent is removed under vacuum. The crude product is purified by silica gel column chromatography eluting with 0% to 3% 7 N ammonia-methanol in dichloromethane gradient, to give the title compound as the free base (118 mg, 82%). The free base is dissolved in a small volume of dichloromethane and is treated with a solution of 1 N hydrogen chloride in diethyl ether (390 µL, 390 µmol) for 5 minutes. The solvents are removed under vacuum to give the title product as a hydrogen chloride salt (130 mg, 0.34 mmol, 79%). ES/MS (m/e): 337 (M+H), [α]$_D^{20}$=−23.1 (C=1.0, EtOH).

The following Examples are prepared essentially as described for Example 23

TABLE 31

| Ex. No. | Chemical name | Structure | ES/MS (m/e) (M + H) |
|---|---|---|---|
| 24 | 2-[2-[(4aR,7aR)-2-Amino-7a-isothiazol-5-yl-4,4a,5,7-tetrahydropyrrolo[3,4-d][1,3]thiazin-6-yl]-5-fluoro-pyrimidin-4-yl]propan-2-ol hydrochloride, isomer 2 | 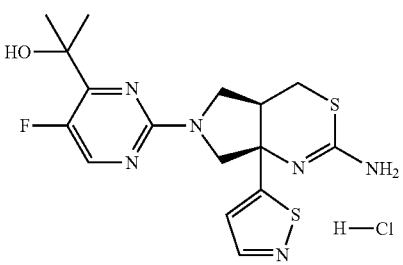 | 395 |

TABLE 31-continued

| Ex. No. | Chemical name | Structure | ES/MS (m/e) (M + H) |
|---|---|---|---|
| 25 | (4aR,7aR)-6-[5-Fluoro-4-(1-fluoro-1-methyl-ethyl)pyrimidin-2-yl]-7a-thiazol-5-yl-4,4a,5,7-tetrahydropyrrolo[3,4-d][1,3]thiazin-2-amine hydrochloride | 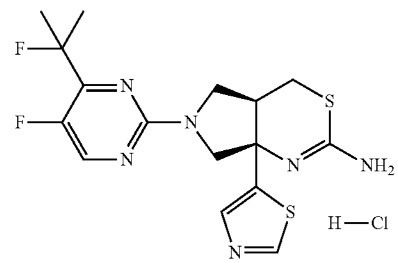 | 397 |
| 26 | (4aR,7aS)-6-[5-Fluoro-4-(1-fluoro-1-methyl-ethyl)pyrimidin-2-yl]-7a-phenyl-4,4a,5,7-tetrahydropyrrolo[3,4-d][1,3]thiazin-2-amine hydrochloride | 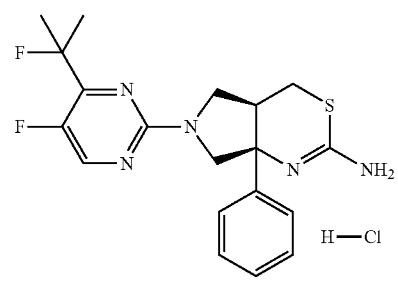 | 390 |
| 27 | 2-[2-[(4aR,7aR)-2-Amino-7a-thiazol-5-yl-4,4a,5,7-tetrahydropyrrolo[3,4-d][1,3]thiazin-6-yl]-5-fluoro-pyrimidin-4-yl]propan-2-ol hydrochloride | 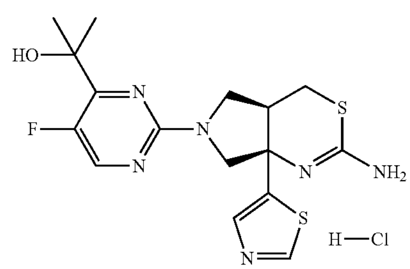 | 395 |
| 28 | 2-[2-[(4aR,7aS)-2-Amino-7a-phenyl-4,4a,5,7-tetrahydropyrrolo[3,4-d][1,3]thiazin-6-yl]-5-fluoro-pyrimidin-4-yl]propan-2-ol hydrochloride | 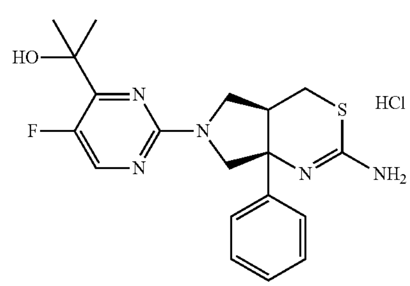 [SMILES: CC(C)(O)c1nc(N2C[C@H]3CSC(N)=N[C@@]3(c3ccccc3)C2)ncc1F ; Cl] | 388 |

TABLE 31-continued

| Ex. No. | Chemical name | Structure | ES/MS (m/e) (M + H) |
|---|---|---|---|
| 29 | (4aR,7aS)-6-(5-Fluoro-4-isopropyl-pyrimidin-2-yl)-7a-phenyl-4,4a,5,7-tetrahydropyrrolo[3,4-d][1,3]thiazin-2-amine hydrochloride[a] | 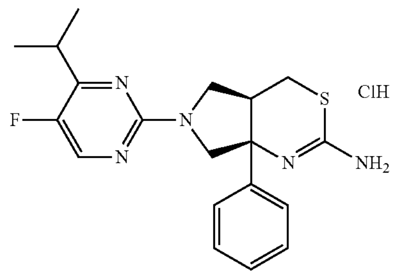 [SMILES: CC(C)c1nc(N2C[C@H]3CSC(N)=N[C@@]3(c3ccccc3)C2)ncc1F ; Cl] | 372 |

[a] The reaction is heated 4 hours and purified with a gradient of 0.5% to 10% 7N ammonia/methanol in dichloromethane.

Example 30

[(4aR,7aR)-7a-(5-Fluorothiophen-2-yl)-6-(pyrimidin-2-yl)-4,4a,5,6,7,7a-hexahydropyrrolo[3,4-d][1,3]thiazin-2-amine hydrochloride

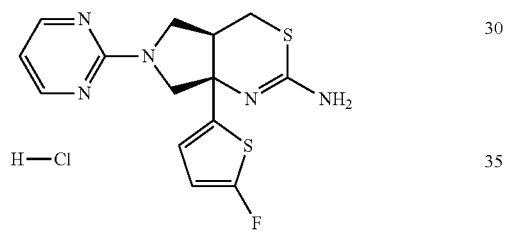

To a stirred clear colorless solution of the [(4aR,7aR)-7a-(5-fluorothiophen-2-yl)-6-(pyrimidin-2-yl)-4,4a,5,6,7,7a-hexahydropyrrolo[3,4-d][1,3]thiazin-2-amine (318 mg, 948 μmol) in diethyl ether (10 mL) and dichloromethane (10 mL) is added a solution of 1 M HCl in diethyl ether (1.05 mL, 1.05 mmol). The resulting white mixture is stirred for a few minutes, then the solid is collected and washed with diethyl ether (15 mL), to give the title compound (325 mg, 92%) as a white solid. ES/MS (m/e): 336.0 (M+H).

The following Example is prepared essentially by the method of Example 30

TABLE 32

| Ex. No. | Chemical name | Structure | ES/MS (m/e) |
|---|---|---|---|
| 31[a] | 5-[(4aR,7aR)-2-Amino-6-(5-fluoropyrimidin-2-yl)-4a,5,6,7-tetrahydropyrrolo[3,4-d][1,3]thiazin-7a(4H)-yl]thiophene-2-carbonitrile hydrochloride | 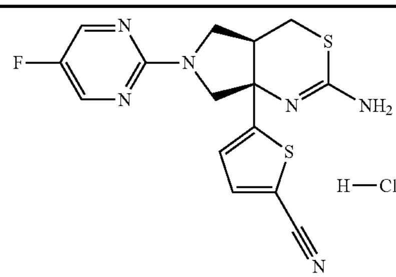 | 361.2 (M + H) |

[a] $[\alpha]_D^{20}$ = −4.4° (C = 1.0, EtOH)

Example 32

[(4aR,7aR)-6-(5-Fluoropyrimidin-2-yl)-7a-(5-fluorothiophen-2-yl)-4,4a,5,6,7,7a-hexahydropyrrolo[3,4-d][1,3]thiazin-2-amine hydrochloride

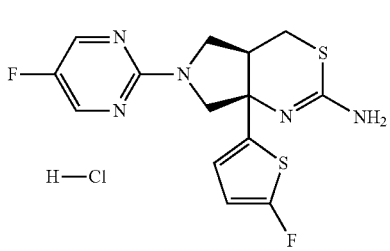 [SMILES: NC1=N[C@@]2(c3ccc(F)s3)CN(c3ncc(F)cn3)C[C@H]2CS1 ; Cl]

To a stirred clear colorless solution of [(4aR,7aR)-6-(5-fluoropyrimidin-2-yl)-7a-(5-fluorothiophen-2-yl)-4,4a,5,6,7,7a-hexahydropyrrolo[3,4-d][1,3]thiazin-2-amine (255 mg, 722 μmol) and diethyl ether (10 mL) is added a solution of 1 M HCl in diethyl ether (794 μL, 794 μmol). The resulting white mixture is stirred for a few minutes and the resulting solid collected and rinsed with diethyl ether (10 mL), to give the title compound (274 mg, 97%) as a white solid. ES/MS (m/e): 354.0 (M+H).

Example 33

5-[(4aR,7aR)-2-Amino-6-[5-fluoro-4-(2-hydroxypropan-2-yl)pyrimidin-2-yl]-4a,5,6,7-tetrahydropyrrolo[3,4-d][1,3]thiazin-7a(4H)-yl]thiophene-2-carbonitrile hydrochloride

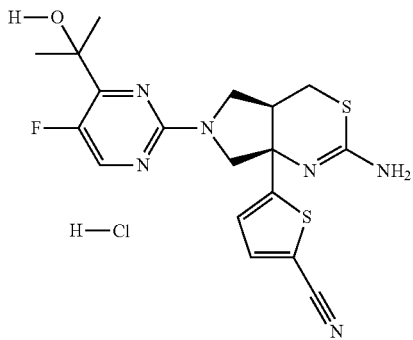 [SMILES: CC(C)(O)c1nc(N2C[C@H]3CSC(N)=N[C@@]3(c3ccc(C#N)s3)C2)ncc1F ; Cl]

To a stirred solution of the 5-[(4aR,7aR)-2-amino-6-[5-fluoro-4-(2-hydroxypropan-2-yl)pyrimidin-2-yl]-4a,5,6,7-tetrahydropyrrolo[3,4-d][1,3]thiazin-7a(4H)-yl]thiophene-2-carbonitrile (256 mg, 612 μmol) in diethyl ether (20 mL) is added a solution of 1 M HCl in diethyl ether (673 μL, 0.673 mmol). The resulting white mixture is stirred for a few minutes, and then the solid is collected by vacuum filtration, and is rinsed with diethyl ether, to give the title compound (201 mg, 72%) as a white solid. MS/ES (m/z) 419.2 (M+H).

Example 34

(4aR,7aS)-7a-(2-Fluorophenyl)-6-(5-fluoropyrimidin-2-yl)-4,4a,5,7-tetrahydropyrrolo[3,4-d][1,3]thiazin-2-amine hydrochloride, isomer 2

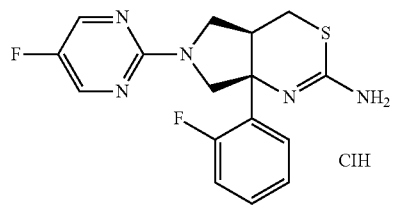

(4aR,7aS)-7a-(2-Fluorophenyl)-6-(5-fluoropyrimidin-2-yl)-4,4a,5,7-tetrahydropyrrolo[3,4-d][1,3]thiazin-2-amine, isomer 2 (100 mg, 0.29 mmol) is dissolved in 1 N HCl (2 mL). The solvent is removed under a stream of nitrogen and dried under vacuum at 50° C. to give the title compound (81 mg, 73%). ES/MS (m/e) 384 (M+H).

Example 35

2-[2-[(4aR,7aR)-2-Amino-7a-isothiazol-5-yl-4,4a,5,7-tetrahydropyrrolo[3,4-d][1,3]thiazin-6-yl]-5-fluoro-6-methyl-pyrimidin-4-yl]propan-2-ol hydrochloride

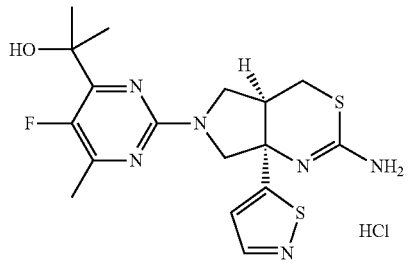 [SMILES: Cc1nc(N2C[C@H]3CSC(N)=N[C@@]3(c3ccns3)C2)nc(C(C)(C)O)c1F ; Cl]

N-[(4aR,7aR)-6-[5-Fluoro-4-(1-hydroxy-1-methylethyl)-6-methyl-pyrimidin-2-yl]-7a-isothiazol-5-yl-4,4a,5,7-tetrahydropyrrolo[3,4-d][1,3]thiazin-2-yl]benzamide (33 mg, 0.064 mmol) is dissolved in ethanol (2 mL). To this solution is added pyridine (0.052 mL, 0.6 mmol) and O-methylhydroxylamine hydrochloride (55 mg, 0.6 mmol). The reaction is warmed to 70° C. for 4 hours. The reaction is cooled to room temperature and stirred overnight (~16 hrs). The mixture is concentrated to give the crude product which is purified via silica gel chromatography using a 0-10% (7 N NH$_3$ in MeOH)/DCM to give the pure freebase. The freebase is dissolved in DCM (2 mL) and treated with 4 M HCl in dioxane (0.3 mL, 1.2 mmol). The mixture is concentrated to give the title compound as a white solid (18 mg, 0.04 mmol). ES/MS (m/z): 409 (M+H). $[\alpha]_D^{20}$=−6.0° (C=1.0, MeOH).

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 1 nM in a 96-well round-bottom plate before conducting the in vitro enzymatic and whole cell assays.

In Vitro Protease Inhibition Assays

BACE1 FRET Assay

Serial dilutions of test compounds are prepared as described above. Compounds are further diluted 20× in $KH_2PO_4$ buffer. Ten μL of each dilution is added to each well on row A to H of a corresponding low protein binding black plate containing the reaction mixture (25 μL of 50 mM $KH_2PO_4$, pH 4.6, 1 mM TRITON® X-100, 1 mg/mL Bovine Serum Albumin, and 15 μM of FRET substrate) (See Yang, et. al., *J. Neurochemistry*, 91(6) 1249-59 (2004)). The content is mixed well on a plate shaker for 10 minutes. Fifteen μL of two hundred μM human BACE1 (1-460):Fc (See Vasser, et al., *Science*, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $EC_{50}$ and $IC_{50}$ values. (See Sinha, et al., *Nature*, 402, 537-540 (2000)).

The compounds of Examples 1-35 herein were tested essentially as described above and exhibited an $IC_{50}$ value for BACE1 of lower than about 1 μM. The following exemplified compounds were tested essentially as described above and exhibited the following activity for BACE1:

TABLE 33

| Example # | BACE1 $IC_{50}$ (nM) |
|---|---|
| 1 | 64.4 (±6.88, n = 6) |
| 16 | 77.3 (±5.51, n = 4) |
| 23 | 172 (±14.5, n = 6) |
| 30 | 166 (±8.62, n = 2) |
| 31 | 110 ±20.6, n = 7) |
| 32 | 91.2 (±10.2, n = 5) |

Mean ± SEM; SEM = standard error of the mean

These data demonstrate that the compounds of Table 33 potently inhibit purified recombinant BACE1 enzyme activity in vitro.

Expression of Human BACE1

Human BACE1 (accession number: AF190725) is cloned from total brain cDNA by room temperature-PCR. The nucleotide sequences corresponding to amino acid sequences #1 to 460 are inserted into the cDNA encoding human $IgG_1$(Fc) polypeptide (Vassar et al. 1999). This fusion protein of BACE1(1-460) and human Fc, named huBACE1:Fc, is constructed into the pJB02 vector. Human BACE1(1-460):Fc (huBACE1:Fc) is transiently expressed in HEK293 cells. 250 μg cDNA of each construct is mixed with Fugene 6 and added to 1 liter HEK293 cells. Four days after the transfection, conditioned media are harvested for purification.

Purification of huBACE1:Fc huBACE1:Fc is purified by Protein A chromatography. The enzyme is stored at −80° C. in small aliquots.

Whole cell assays for measuring the Inhibition of Beta-Secretase Activity

HEK293Swe Whole Cell Assay

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met652 to Asn651Leu652, commonly called the Swedish mutation (noted HEK293/APP751sw) and shown to overproduce Abeta (Citron, et al., *Nature*, 360, 672-674 (1992)). In vitro Abeta reduction assays have been described in the literature (See Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997)).

Cells (HEK293/APP751sw at $3.5 \times 10^4$ cells/well, containing 200 μL culture media, DMEM containing 10% FBS) are incubated at 37° C. for 4 to 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 34

| Example | HEK 293 Swe A-beta (1-40) ELISA $IC_{50}$ (nM) | HEK 293 Swe A-beta (1-42) ELISA $IC_{50}$ (nM) |
|---|---|---|
| 1 | 233 (±29.9, n = 4) | 244 (±113, n = 3) |
| 16 | 262 (±188, n = 5) | 256 (±137, n = 4) |
| 23 | 1550 (±76.8, n = 2) | 1910 (±107, n = 2) |
| 31 | 874 | 1330 |
| 32 | 345 | 356 |

Mean ± SEM; SEM = standard error of the mean

These data demonstrate that the compounds of Table 34 inhibit native endogenous human BACE1 in cells in vitro.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 2 days in vitro, culture media is replaced with serum free DMEM/F12 (1:1) containing B27 supplement and 2 μM (final) of Ara-C (Sigma, C1768). At day 5 in vitro, neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 35

| Example | PDAPP Neuron A-beta (1-40) ELISA $IC_{50}$ (nM) | PDAPP Neuron A-beta (1-42) ELISA $IC_{50}$ (nM) |
|---|---|---|
| 1 | 116 | 103 |
| 16 | 379 | 203 |
| 23 | 2240 (±1020, n = 4) | 2870 (±1150, n = 4) |
| 31 | 1210 (±190, n = 3) | 1700 (±383, n = 3) |
| 32 | 378 | 245 |

Mean ± SEM; SEM = standard error of the mean

These data demonstrate that the compounds of Table 35 inhibit native, endogenous murine BACE1 in cells in vitro.

In Vivo Inhibition of Beta-Secretase

Several animal models, including mouse, guinea pig, dog, and monkey, may be used to screen for inhibition of beta-secretase activity in vivo following compound treatment Animals used in this invention can be wild type, transgenic, or gene knockout animals. For example, the PDAPP mouse model, prepared as described in Games et al., Nature 373, 523-527 (1995), and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, PHARMASOLVE®, or other suitable vehicles. One to twenty-four hours following the administration of compound, animals are sacrificed, and brains as well as cerebrospinal fluid and plasma are removed for analysis of Abetas, C99, and sAPP fragments. (See Dovey, et al., Journal of Neurochemistry, 76, 173-181 (2001); and Johnson-Wood, et al., Proc. Natl. Acad. Sci. USA, 94, 1550-1555 (1997)).

For standard in vivo pharmacology studies, animals are dosed with various concentrations of compound and compared to a vehicle-treated control group dosed at the same time. For some time course studies, brain tissue, plasma, or cerebrospinal fluid is obtained from selected animals, beginning at time 0 to establish a baseline. Compound or appropriate vehicle is administered to other groups and sacrificed at various times after dosing. Brain tissue, plasma, or cerebrospinal fluid is obtained from selected animals and analyzed for the presence of APP cleavage products, including Abeta peptides, sAPPbeta, and other APP fragments, for example, by specific sandwich ELISA assays. At the end of the test period, animals are sacrificed and brain tissues, plasma, or cerebrospinal fluid are analyzed for the presence of Abeta peptides, C99, and sAPPbeta, as appropriate. Brain tissues of APP transgenic animals may also be analyzed for the amount of beta-amyloid plaques following compound treatment. "Abeta 1-x peptide" as used herein refers to the sum of Abeta species that begin with residue 1 and ending with a C-terminus greater than residue 28. This detects the majority of Abeta species and is often called "total Abeta".

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls or time zero controls. For example, 3 hours after administration of 10 mg/kg oral dose of the compound of Example 1 to young female PDAPP mice, Abeta 1-x peptide, C99 and sAPPb levels are reduced approximately 51%, 58%, and 37% in brain hippocampus, and approximately 62%, 63% and 34% in brain cortex, respectively, compared to vehicle-treated mice. Consistent with changes in brain parenchyma, CSF Abeta 1-x levels are reduced by approximately 80% 3 hours after oral administration of a 10 mg/kg dose of the compound of Example 1. Reduction of CSF sAPPbeta by 22% 3 hours after oral administration of a 10 mg/kg dose of the compound of Example 1 is consistent with a mechanism of BACE inhibition in vivo.

For Example 23, 3 hours after administration of 30 mg/kg oral dose of the compound of Example 23, Abeta 1-x peptide levels are reduced approximately 45% in brain hippocampus, and approximately 52% in brain cortex compared to vehicle-treated mice.

For Example 31, three hours after administration of 10 or 30 mg/kg oral dose of the compound of Example 31, Abeta 1-x peptide levels are reduced approximately 18% and 51% in brain hippocampus, and approximately 23% and 63% in brain cortex, respectively, compared to vehicle-treated mice. Given the activity of Examples 23 and 31 against BACE enzyme in vitro, these Abeta lowering effects are consistent with BACE inhibition in vivo.

These studies show that compounds of the present invention inhibit BACE and are, therefore, useful in reducing Abeta levels. As such, compounds of the present invention are efficacious inhibitors of BACE.

We claim:

1. A pharmaceutical composition comprising a compound of the formula:

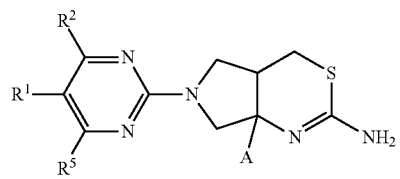

wherein A is selected from the group consisting of;

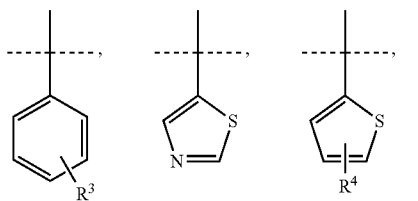

-continued

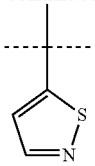

R¹ is H or F;
R² is H, —CH$_2$OH, C1-C3 alkyl,

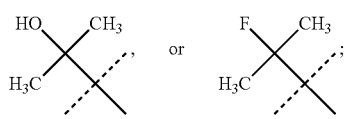

R³ is H, F, or CN;
R⁴ is H, F; or CN; and
R⁵ is H, —CH$_3$, or —OCH$_3$;
 or a pharmaceutically acceptable salt thereof, in combination with one or more pharmaceutically acceptable carriers, diluents, or excipients.

2. A pharmaceutical composition according to claim 1 wherein A is selected from the group consisting of:

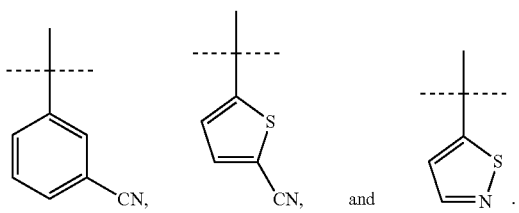

3. A pharmaceutical composition according to claim 2 wherein A is selected from the group consisting of:

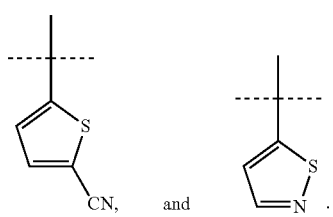

4. A pharmaceutical composition according to claim 1 wherein R¹ is F.

5. A pharmaceutical composition according to claim 4 wherein R² is H.

6. A pharmaceutical composition according to claim 4 wherein R² is

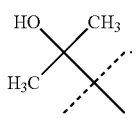

7. A pharmaceutical composition according to claim 5 wherein R⁵ is H.

8. A pharmaceutical composition according to claim 6 wherein R⁵ is H.

9. A pharmaceutical composition according to claim 7 wherein A is selected from the group consisting of:

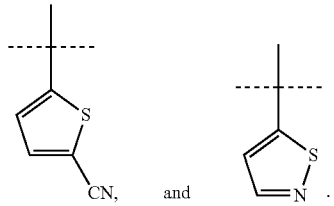

10. A pharmaceutical composition according to claim 8 wherein A is selected from the group consisting of:

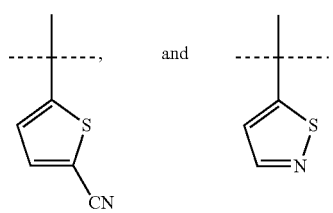

11. A pharmaceutical composition comprising a compound which is (4aR,7aR)-6-(5-fluoropyrimidin-2-yl)-7a-isothiazol-5-yl-4,4a,5,7-tetrahydropyrrolo[3,4-d][1,3]thiazin-2-amine:

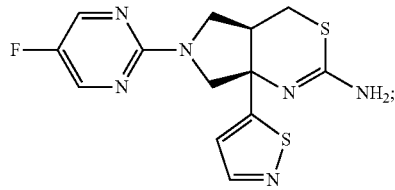 [SMILES: NC1=N[C@@]2(c3ccns3)CN(c3ncc(F)cn3)C[C@H]2CS1]

or a pharmaceutically acceptable salt thereof in combination with one or more pharmaceutically acceptable carriers, diluents, or excipients.

12. A pharmaceutical composition comprising a compound according to claim 11 which is (4aR,7aR)-6-(5-fluoropyrimidin-2-yl)-7a-isothiazol-5-yl-4,4a,5,7-tetrahydropyrrolo[3,4-d][1,3]thiazin-2-amine:

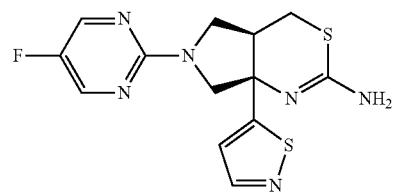 [SMILES: NC1=N[C@@]2(c3ccns3)CN(c3ncc(F)cn3)C[C@H]2CS1]

in combination with one or more pharmaceutically acceptable carriers, diluents, or excipients.

* * * * *